(12) United States Patent
Davila

(10) Patent No.: US 10,975,137 B2
(45) Date of Patent: Apr. 13, 2021

(54) CD8A AND T CELL RECEPTOR VARIANTS AND METHODS OF USING SAME IN MODULATING IMMUNE CELL RESPONSES

(71) Applicant: Eduardo Davila, Cockeysville, MD (US)

(72) Inventor: Eduardo Davila, Cockeysville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 373 days.

(21) Appl. No.: 15/524,887

(22) PCT Filed: Nov. 6, 2015

(86) PCT No.: PCT/US2015/059510
§ 371 (c)(1),
(2) Date: May 5, 2017

(87) PCT Pub. No.: WO2016/073875
PCT Pub. Date: May 12, 2016

(65) Prior Publication Data
US 2018/0282391 A1 Oct. 4, 2018

Related U.S. Application Data

(60) Provisional application No. 62/130,092, filed on Mar. 9, 2015, provisional application No. 62/076,120, filed on Nov. 6, 2014.

(51) Int. Cl.
| | | |
|---|---|---|
| *C07K 14/70* | (2006.01) | |
| *C07K 14/705* | (2006.01) | |
| *C07K 14/725* | (2006.01) | |
| *C07K 14/73* | (2006.01) | |
| *A61P 35/00* | (2006.01) | |
| *A61K 35/17* | (2015.01) | |
| *C07K 14/47* | (2006.01) | |
| *A61K 38/00* | (2006.01) | |

(52) U.S. Cl.
CPC ........ *C07K 14/70517* (2013.01); *A61K 35/17* (2013.01); *A61P 35/00* (2018.01); *C07K 14/47* (2013.01); *C07K 14/7051* (2013.01); *C07K 14/70514* (2013.01); *A61K 38/00* (2013.01); *C07K 2319/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 5,712,149 A | 1/1998 | Roberts |
| 2011/0287038 A1* | 11/2011 | Slawin ................. A61K 31/711 424/184.1 |

FOREIGN PATENT DOCUMENTS

| | | |
|---|---|---|
| WO | 2013/142034 | 9/2013 |
| WO | 2014/011987 | 1/2014 |
| WO | 2014/039961 | 3/2014 |
| WO | 2014/099671 | 6/2014 |

OTHER PUBLICATIONS

Extended European Search Report dated Jun. 14, 2018 in European Application No. 15857640.5.
Geng et al., "Amplifying TLR-MyD88 Signals within Tumor-Specific T Cells Enhances Antitumor Activity to Suboptimal Levels of Weakly Immunogenic Tumor Antigens", Cancer Research, 70(19):7442-7454 (2010).
Kfoury et al., "Dual function of MyD88 in inflammation and oncogenesis: implications for therapeutic intervention", Current Opinion in Oncology, 26(1):86-91 (2014).
Zhao et al., "The Adaptor Molecule MyD88 Directly Promotes CD8 T Cell Responses to Vaccinia Virus", The Journal of Immunology, 182(10):6278-6286 (2009).
Zhong et al., "Chimeric Antigen Receptors Combining 4-1BB and CD28 Signaling Domains Augment $PI_3$kinase/AKT/Bcl-$X_L$ Activation and $CD8^+$T Cell-mediated Tumor Eradication", Molecular Therapy, 18(2): 413-420 (2010).
Xu et al., "Tumor-specific dendritic cells generated by genetic redirection of Toll-like receptor signaling against the tumor-associated antigen, erbB2", Cancer Gene Therapy, 14: 773-780 (2007).
Norment et al., "Alternatively spliced mRNA encodes a secreted form of human CD8 alpha. Characterization of the human CD8 alpha gene", J Immunol, 142(9): 3312-3319 (1989)—Abstract only as provided with ISR.
UniProtKB/Swiss-Prot: P01732.1, CD8A_HUMAN, Oct. 1, 2014.
Shore et al., "The crystal structure of CD8αβ in complex with YTS156.7.7 Fab and interaction with other CD8 antibodies define the binding mode of CD8αβ to MHC class I", J Mol Biol, 384(5): 1190-1202 (2008).

(Continued)

*Primary Examiner* — Nelson B Moseley, II
(74) *Attorney, Agent, or Firm* — Wenderoth, Lind & Ponack, L.L.P.

(57) ABSTRACT

Novel costimulatory fusion proteins and DNA sequences that enhance T cell responses to weakly immunogenic and/or lowly expressed antigens and that confer T cell resistance against MDSC-mediated suppression are disclosed. The fusion proteins comprise portions of CD4, CD8α or the T cell receptor linked to a specific region of MyD88 or other signaling molecules. These fusion proteins and sequence variants thereof improve T cell activation and responsiveness. Also disclosed is the use of these molecules in host cells as a means to enhance and costimulate responses of immune cells including cytotoxic $CD8^+$ T cells and the use of these cells to treat cancer, infectious agents and other diseases.

19 Claims, 15 Drawing Sheets
Specification includes a Sequence Listing.

(56) References Cited

OTHER PUBLICATIONS

UniProtKB/Swiss-Prot: P01731.1, CD8A_Mouse, Oct. 1, 2014.
International Search Report, dated Mar. 30, 2016 in corresponding International Application No. PCT/US15/59510.

* cited by examiner

CD8A AND T CELL RECEPTOR VARIANTS AND METHODS OF USING SAME IN MODULATING IMMUNE CELL RESPONSES

STATEMENT OF FEDERALLY SPONSORED RESEARCH AND DEVELOPMENT

This invention was made with government support under Grant Number CA140917 awarded by the National Institutes of Health. The government has certain rights in the invention.

BACKGROUND

Recent research has shown that altering CD8+ T cell responses in a subject can have a number of benefits. For example, ongoing clinical trials using infusions of tumor infiltrating lymphocytes or T cells engineered to express tumor-reactive T cell receptors (TCR) to destroy cancer have shown promise. However, these studies have also revealed subsets of patients in whom the T cell therapy is ineffective. Additional applications for augmented CD8+ T cell responses are exemplified by the observation that many elderly and pediatric patients exhibit weak or no responses to vaccines such as the influenza vaccine, resulting in 50,000 deaths in the U.S. from influenza virus. Furthermore, the up-regulation of CD8+ T cell responses can enhance vaccine efficacy and enhance the efficacy of T cell-based immunotherapies.

The type and intensity of CD8+ T cell responses to any given antigen is governed by various molecular interactions that occur between T cells and antigen presenting cells. Such responses are largely the result of contact between TCRs on T cells and major histocompatibility complex (MHC) molecules on antigen presenting cells. Signaling by TCRs is modulated by the affinity of the TCR to the antigenic peptide presented on MHC I as well as the duration of the interaction between the TCR and the MHC-antigen (MHC/Ag). Thus, much attention has been focused on attempts to define high affinity peptides or to develop higher affinity TCRs.

The CD8α molecule serves as a TCR coreceptor and interacts with the α3 and α2 domain of the MHC I molecule and with HLA β$_2$ microglobulin. CD8α helps maintain TCR:MHC/Ag stability and keeps the TCR bound closely to the target cell during antigen-specific activation. Although CD8α interacts with CD8β, only the CD8α interacts with MHC I. Interaction between CD8α and MHC I contributes to cellular avidity in part by reducing the off rate of the TCR and promoting TCR clustering. The cytoplasmic domain of CD8α contains a p56$^{lck}$ binding domain that is important for TCR signal transduction.

Studies from various groups have demonstrated that stimulating Toll-like receptors (TLR) on T cells enhances a variety of T cell responses. For example, TLR2 engagement has been shown to decrease the TCR activation threshold and enhance T cell responses to suboptimal levels of Ags. TLR-stimulated T cells also exhibit increased IL-2 production, enhanced proliferation and survival, increased cytolytic activity, and enhanced antitumor activity in mice. However, it has been found that one limitation to stimulating TLRs on T cells is that the costimulatory effects require simultaneous TCR activation and that antitumor efficacy is limited in part by several factors, including low and transient TLR expression on T cells and the inability to localize sufficient TLR ligands at the tumor sites to costimulate T cells. Additionally, cancer cells, including melanoma, can express TLRs, and TLR engagement on cancer cells can induce the expression of various tumor growth factors.

Another limitation to achieving effective and durable T cell response includes the presence of myeloid derived suppressor cells (MDSCs). MDSCs represent a heterogeneous population of cells comprised of myeloid-cell progenitors and precursors of monocytic and granulocytic myeloid cells. MDSCs suppress T cell responses via: L-arginine depletion through arginase-1, inducible nitric oxide synthase (iNOS) activity, increased generation of reactive oxygen species (ROS), and production of TGF-β. A recent report emphasized a critical role of the cellular stress sensor C/EBP-homologous protein (Chop) in the inhibitory activity of MDSCs. In patients with advanced melanoma, circulating MDSCs correlate directly with low patient survival and inversely with functional TAg—specific T cells. In addition to blunting T cell activity, MDSCs play a critical role in inducing and maintaining Tregs in melanoma. Furthermore, factors produced by MDSCs (i.e. IL-6, TNF and IL-1β) promote tumor growth, therefore developing strategies to block their multi-factorial pro-tumor function has the potential to increase antitumor T cell activity.

BRIEF SUMMARY

As described in detail below, the inventors of the present application have found that MyD88 signaling directly within CD8+ T cells reduces the T cell receptor (TCR) activation threshold to poorly immunogenic antigens and also augments responses to sub-optimal levels of antigen presentation. Concomitant activation of TCR and MyD88 signaling enhances T cell proliferation, increases cytolytic activity, confers resistance to MDSC-mediated T cell suppression, reduces tumor growth kinetics and prolongs survival of tumor-bearing mice.

Based on these findings, the inventors prepared fusion proteins comprising molecules involved in T cell activation. In particular, the fusion proteins comprising portions of CD4, CD8α or the T cell receptor linked to a region of MyD88 or other signaling molecules were prepared. These fusion proteins, and sequence variants thereof (collectively, these fusion proteins and sequence variants are referred to herein as the "variants" of the invention), improve T cell activation and responsiveness. The expression of these variants is shown to have profound effects on T cell activation and responsiveness resulting in enhanced antitumor activity.

CD8α-MyD88

In a first embodiment, the invention is directed to CD8α fusion proteins, and polynucleotides encoding the same, comprising extracellular and transmembrane regions of CD8α linked to a region of MyD88 lacking the TIR domain. In one aspect of this embodiment, these regions are linked as: N-extracellular region of CD8α-transmembrane region of CD8α-region of MyD88 lacking the TIR domain-C. The CD8α portion of these fusion proteins may be from any mammalian CD8α, including mouse and human. The MyD88 portion of these fusion proteins may also be from any mammalian source, including mouse and human.

In one aspect of this embodiment, the extracellular and transmembrane regions of mouse CD8α correspond to amino acids 1-217 of mouse CD8α (SEQ ID NO:16). In one aspect of this embodiment, the extracellular and transmembrane regions of human CD8α correspond to amino acids 1-203 of human CD8α (SEQ ID NO:12). In one aspect of this embodiment, the region of human MyD88 lacking the TIR domain corresponds to amino acids 1-155 of human MyD88 (SEQ ID NO:24). In specific aspects of this embodiment, the invention includes the CD8α fusion proteins mCD8α-hMyD88, set forth in SEQ ID NO:17, and hCD8α-hMyD88, set forth in SEQ ID NO:14. In other specific aspects of this embodiment, the invention includes polynucleotides encoding mCD8α-hMyD88, set forth in SEQ ID NO:6, and hCD8α-hMyD88, set forth in SEQ ID NO:3.

CD8αTM-MyD88

In a second embodiment, the invention is directed to CD8α fusion proteins, and polynucleotides encoding the same, comprising the transmembrane region of CD8α linked to a region of MyD88 lacking the TIR domain. In one aspect of this embodiment, these regions are linked as: N-transmembrane region of CD8α-region of MyD88 lacking the TIR domain-C. The CD8α portion of these fusion proteins may be from any mammalian CD8α, including mouse and human. The MyD88 portion of these fusion proteins may also be from any mammalian source, including mouse and human.

In one aspect of this embodiment, the transmembrane region of human CD8α corresponds to amino acids 128-210 of human CD8α (amino acids 1-83 of SEQ ID NO:18). In one aspect of this embodiment, the region of human MyD88 lacking the TIR domain corresponds to amino acids 1-155 of human MyD88 (SEQ ID NO:24). In specific aspects of this embodiment, the invention includes the CD8α fusion protein hCD8αTM-hMyD88, set forth in SEQ ID NO:18. In other specific aspects of this embodiment, the invention includes the polynucleotide encoding hCD8αTM-hMyD88, set forth in SEQ ID NO:7.

CD8α-28-137-3

In a third embodiment, the invention is directed to CD8α fusion proteins, and polynucleotides encoding the same, comprising the extracellular and transmembrane regions of CD8α linked to the intracellular signaling domains of CD28, CD137 (4-1BB), and CD3ξ. The CD8α portion of these fusion proteins may be from any mammalian CD8α, including mouse and human. The CD28, CD137 (4-1BB), and CD3ξ intracellular signaling domains may also be from any mammalian source, including mouse and human.

In one aspect of this embodiment, the extracellular and transmembrane regions of mouse CD8α correspond to amino acids 1-217 of mouse CD8α (SEQ ID NO:16). In one aspect of this embodiment, the extracellular and transmembrane regions of human CD8α correspond to amino acids 1-203 of human CD8α (SEQ ID NO:12). In one aspect of this embodiment, the CD28, CD137 (4-1BB), and CD3ξ domains correspond to amino acids 218-417 of SEQ ID NO:19, where CD28 corresponds to amino acids 218-256; CD137 (4-1BB) corresponds to amino acids 259-305; CD3ξ corresponds to amino acids 308-417. In specific aspects of this embodiment, the invention includes the CD8α fusion protein mCD8α-28-137-3, set forth in SEQ ID NO:19. In other specific aspects of this embodiment, the invention includes the polynucleotide encoding mCD8α-28-137-3, set forth in SEQ ID NO:8.

CD4-MyD88

In a fourth embodiment, the invention is directed to CD8α fusion proteins, and polynucleotides encoding the same, comprising extracellular and transmembrane regions of CD4 linked to a region of MyD88 lacking the TIR domain. In one aspect of this embodiment, these regions are linked as: N-extracellular region of CD4-transmembrane region of CD4-MyD88 lacking the TIR domain-C. The CD4 portion of these fusion proteins may be from any mammalian CD4, including mouse and human. The MyD88 portion of these fusion proteins may also be from any mammalian source, including mouse and human.

In one aspect of this embodiment, the extracellular and transmembrane regions of mouse CD4 correspond to amino acids 1-417 of mouse CD4 (amino acids 1-417 of SEQ ID NO:21). In one aspect of this embodiment, the extracellular and transmembrane regions of human CD4 correspond to amino acids 1-418 of human CD4 (amino acids 1-418 of SEQ ID NO:20). In one aspect of this embodiment, the region of human MyD88 lacking the TIR domain corresponds to amino acids 1-155 of human MyD88 (SEQ ID NO:24). In specific aspects of this embodiment, the invention includes the CD4 fusion proteins mCD4-hMyD88, set forth in SEQ ID NO:21, and hCD4-hMyD88, set forth in SEQ ID NO:20. In other specific aspects of this embodiment, the invention includes polynucleotides encoding mCD4-hMyD88, set forth in SEQ ID NO:10, and hCD4-hMyD88, set forth in SEQ ID NO:9.

TCR-MyD88

In a fifth embodiment, the invention is directed to TCR fusion proteins, and polynucleotides encoding the same, comprising a TCR linked to a region of MyD88 lacking the TIR domain. In one aspect of this embodiment, these elements are linked as: N-TCR-MyD88 lacking the TIR domain-C. The TCR portion of these fusion proteins may be from any mammalian TCR, including mouse and human. The MyD88 portion of these fusion proteins may also be from any mammalian source, including mouse and human.

In one aspect of this embodiment, the TCR is the DMF5 TCR having the amino acid sequence of residues 1-603 of SEQ ID NO:22. In one aspect of this embodiment, the region of human MyD88 lacking the TIR domain corresponds to amino acids 1-155 of human MyD88 (SEQ ID NO:24). In specific aspects of this embodiment, the invention includes the TCR fusion protein hTCR-hMyD88, set forth in SEQ ID NO:22. In other specific aspects of this embodiment, the invention includes the polynucleotide encoding hTCR-hMyD88, set forth in SEQ ID NO:11.

Sequence Variants

Each of the embodiments and aspects of the invention includes sequence variants of the fusion proteins and the polynucleotides encoding the fusion proteins wherein the length of each peptide region or domain comprising a fusion protein individually varies on the amino terminus, carboxy terminus, or both ends, by up to 10 amino acids based on the native sequence of the polypeptide from which the peptide region or domain is obtained. In certain aspects, sequence variants have at least 75% of the activity of the specific fusion protein upon which they are based.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

Each of the embodiments and aspects of the invention also includes sequence variants of the fusion proteins, and polynucleotides encoding the same, having at least 80% sequence identity with a specific fusion protein defined herein, over the entire length of that specific fusion protein. In certain aspects, these sequence variants will have at least 75% of the activity of the specific fusion protein upon which they are based.

Cells

In a sixth embodiment, the invention is directed to isolated populations of cells expressing at least one variant of the invention. In one aspect of this embodiment, the at least one variant is selected from the group consisting of mCD8α- hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect of this embodiment, the at least one variant is encoded by a polynucleotide sequence selected from the group consisting of the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

In one aspect of this embodiment, the sequence variant has at least 80% sequence identity with a specific fusion protein defined herein, over the entire length of that specific fusion protein.

In one aspect of this embodiment, the cells are selected from the group consisting of CD4$^+$ T cells, CD8$^+$ T cells, natural killer T cells (NKT cells), natural killer cells (NK), neutrophils, macrophages, dendritic cells, mast cells, basophils, B cells and other peripheral blood mononuclear cells (PBMC) or other primary or established cell lines including the so-called universal donor cells.

In one aspect of this embodiment, the cells are engineered to express the fusion proteins and sequence variants via viral-mediated gene integration. However, other means of gene integration or protein expression such as nucleofection or transient expression of DNA, RNA or proteins are also suitable.

Methods of Treatment

In a seventh embodiment, the invention is directed to methods of treating a subject having cancer, comprising administering to a subject having cancer a therapeutically-effective amount of a population of cells expressing at least one variant of the present invention.

In one aspect of this embodiment, the at least one variant is selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect of this embodiment, the at least one variant is encoded by a polynucleotide sequence selected from the group consisting of the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

In one aspect of this embodiment, the sequence variant has at least 80% sequence identity with a specific fusion protein defined herein, over the entire length of that specific fusion protein.

In one aspect of this embodiment, the cells are selected from the group consisting of CD4$^+$ T cells, CD8$^+$ T cells, natural killer T cells (NKT cells), natural killer cells (NK), neutrophils, macrophages, dendritic cells, mast cells, basophils, B cells and other peripheral blood mononuclear cells (PBMC), tumor infiltrating lymphocytes or other primary or established cell lines including the so-called universal donor cells.

In an eighth embodiment, the invention is directed to methods of treating a subject having an infectious disease, comprising administering to a subject having an infectious disease a therapeutically-effective amount of a population of cells expressing at least one variant of the present invention.

In one aspect of this embodiment, the at least one variant is selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect of this embodiment, the at least one variant is encoded by a polynucleotide sequence selected from the group consisting of the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

In one aspect of this embodiment, the sequence variant has at least 80% sequence identity with a specific fusion protein defined herein, over the entire length of that specific fusion protein.

In one aspect of this embodiment, the cells are selected from the group consisting of CD4$^+$ T cells, CD8$^+$ T cells, natural killer T cells (NKT cells), natural killer cells (NK), neutrophils, macrophages, dendritic cells, mast cells, basophils, B cells and other peripheral blood mononuclear cells (PBMC), tumor infiltrating lymphocytes or other primary or established cell lines including the so-called universal donor cells.

In one aspect of this embodiment, the infectious disease is caused by a bacterium, a virus or a fungus.

In an ninth embodiment, the invention is directed to methods of treating a subject having an autoimmune disorder, comprising administering to a subject having an autoimmune disorder a therapeutically-effective amount of a population of cells expressing at least one variant of the present invention.

In one aspect of this embodiment, the at least one variant is selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect of this embodiment, the at least one variant is encoded by a polynucleotide sequence selected from the group consisting of the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

In one aspect of this embodiment, the sequence variant has at least 80% sequence identity with a specific fusion protein defined herein, over the entire length of that specific fusion protein.

In one aspect of this embodiment, the cells are selected from the group consisting of CD4+ T cells, CD8+ T cells, natural killer T cells (NKT cells), natural killer cells (NK), neutrophils, macrophages, dendritic cells, mast cells, basophils, B cells and other peripheral blood mononuclear cells (PBMC), tumor infiltrating lymphocytes or other primary or established cell lines including the so-called universal donor cells.

In one aspect of this embodiment, the autoimmune disorder is selected from the group consisting of lupus, arthritis, Type I diabetes, multiple sclerosis, Alopecia areata, and Celiac disease.

Methods of Enhancing Antigen Recognition

In a tenth embodiment, the invention is directed to methods of conferring T cell resistance against MDSC-mediated suppression. These methods comprise expressing at least one variant of the present invention in a T cells.

In one aspect of this embodiment, the at least one variant is selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect of this embodiment, the at least one variant is encoded by a polynucleotide sequence selected from the group consisting of the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

In one aspect of this embodiment, the sequence variant has at least 80% sequence identity with a specific fusion protein defined herein, over the entire length of that specific fusion protein.

In an eleventh embodiment, the invention is directed to methods of enhancing immune cell recognition of an antigen. These methods comprise expressing at least one variant of the present invention in an immune cell.

In one aspect of this embodiment, the at least one variant is selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect of this embodiment, the at least one variant is encoded by a polynucleotide sequence selected from the group consisting of the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In one aspect of this embodiment, the sequence variant is a sequence variant wherein the length of at least one peptide region or domain comprising the fusion protein individually varies on the amino terminus, carboxy terminus, or both ends, by up to 10 amino acids based on the native sequence of the polypeptide from which the peptide region or domain is obtained.

In one aspect of this embodiment, the sequence variant has at least 80% sequence identity with a specific fusion protein defined herein, over the entire length of that specific fusion protein.

In one aspect of this embodiment, the immune cells are selected from the group consisting of CD4+ T cells, CD8+ T cells, natural killer T cells (NKT cells), natural killer cells (NK), neutrophils, macrophages, dendritic cells, mast cells, basophils, B cells and other peripheral blood mononuclear cells (PBMC), tumor infiltrating lymphocytes or other primary or established cell lines including the so-called universal donor cells.

In certain aspects of this embodiment, the antigen is present at a low concentration in vitro or in vivo, or the antigen is a weakly antigenic antigen, or both.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other formulations for carrying out the same purposes of the present invention. It should also be realized by those skilled in the art that such equivalent formulations do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 4A—HEK cells remained untransfected or were transfected with mCD8α-hMyD88. FIG. 4B—mouse CD8+ pmel T cells were transduced with mCD8α-hMyD88 and transfection efficiency, based on % of GFP+ T cells, was determined 48 hours after transduction.

DETAILED DESCRIPTION OF THE INVENTION

I. Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Figure 1:
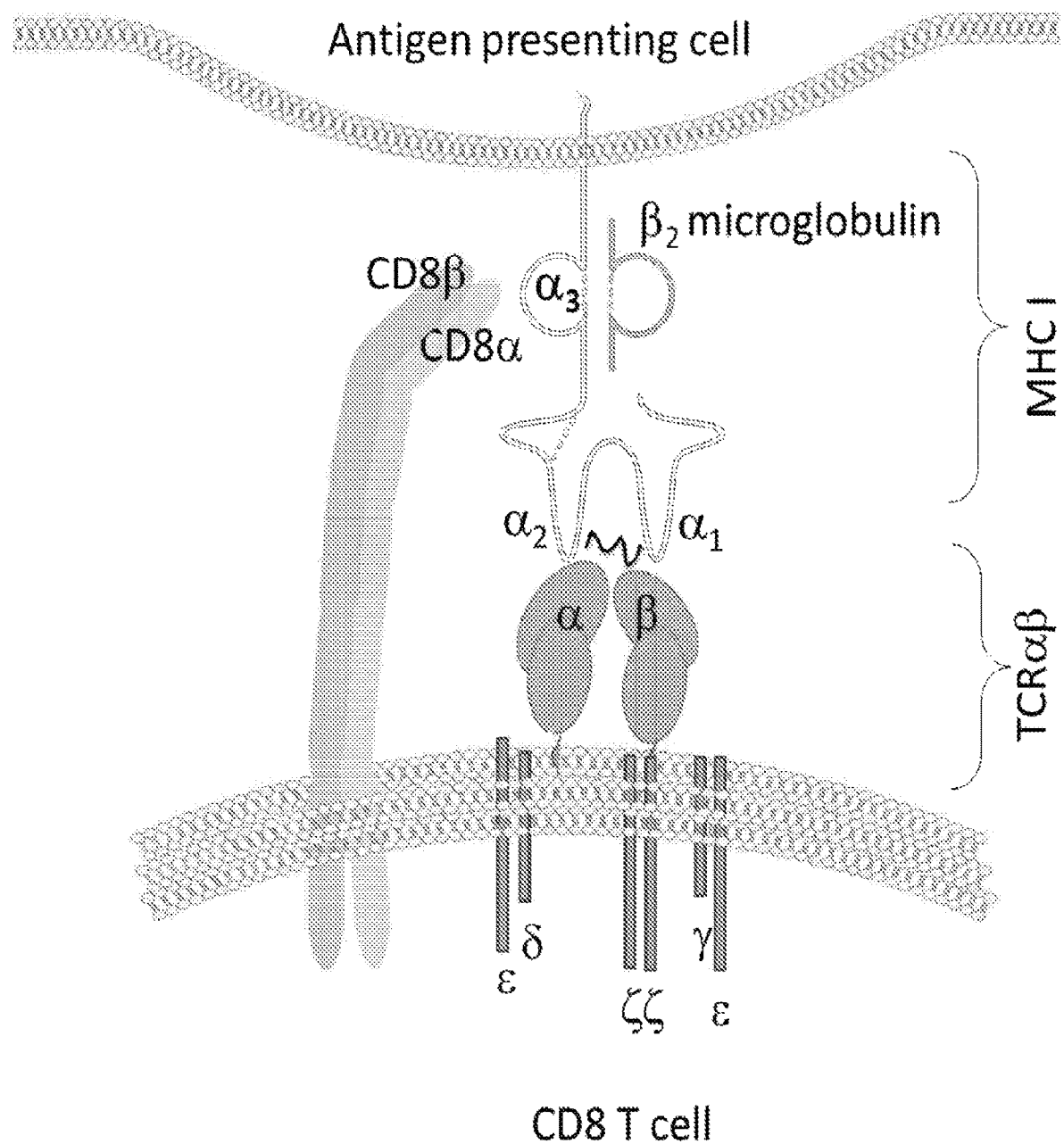
FIG. 1 is an illustration of the physical interaction between T cell receptors and MHC molecules.

The intensity of CD8+ T cell responses to any given antigen is governed by various molecular interactions that occur between T cells and antigen presenting cells. Such interactions include the interaction between T cell receptors (TCRs) expressed by T cells and MHC molecules expressed by antigen presenting cells, as shown in FIG. 1.

Signaling generated by the TCR is modulated in large part by the interaction between the CD8 co-receptor on CD8+ T cells and the MHC protein on the antigen-presenting cells. As can been seen in FIG. 1, the CD8 co-receptor is composed of two subunits: CD8α and the CD8β, with only the CD8α subunit interacting directly with MHC I, via the α3 domain of the protein.

Data presented herein and published reports have also demonstrated that stimulating Toll-like receptor (TLR)-MyD88 signaling directly within CD8+ and CD4+ T cells reduces the T cell receptor (TCR) activation threshold to poorly immunogenic antigens and also augments responses to sub-optimal levels of immunodominant antigen presentation. Concomitant activation of TCR and TLR signaling enhances T cell proliferation, increases cytolytic activity, and prolongs survival of effector T cells in tumor-bearing mice. Intriguingly, immune cells from elderly individuals exhibit reduced expression levels of TLRs and are generally hyporesponsive to TLR stimulation.

Together with extensive studies conducted by the inventor, these observations have led to the development of the CD4, CD8 and TCR variants described herein, polypeptides involved in T cell activation that have improved T cell activation and responsiveness.

In particular, it has been found that altering the amino acid sequence of the CD8α subunit and the T cell receptor to include a specified region of human MyD88 protein can have profound effects on T cell activation and responsiveness. This was accomplished by creating synthetic genes that fuse the extracellular and transmembrane regions of CD8α or the TCR to a specific a region of MyD88. CD8+ T cells were then engineered to express these genes and the CD8α-MyD88 fusion proteins were found to exhibit significantly improved responses over other CD8α vectors as measured by IFN-γ production, T cell proliferation and enhanced cytotoxicity. Thus, changes to the amino acid sequence of the CD8α subunit were found modulate the affinity of CD8 for MHC I and in turn, the nature of the CD8+ T cell response to a selected antigen. Some of these same results were found when TCR-MyD88 fusion proteins were prepared and tested. This surprising discovery serves as a basis for the novel polypeptides, cells lines, and methods reported and claimed herein.

Some novel features and useful applications of the present invention include:
- CD8α variants of the invention can be linked together with the soluble TCR (sTCR) or membrane-bound TCR to enhance the TCR affinity to peptide MHC.
- CD8α variants of the invention can be expressed on T cells to enhance endogenous TCR signals to any given antigen.
- CD8α variants of the invention can be co-expressed along with transgenic tumor-reactive TCRs (or TCRs specific against other antigens such viral or other intracellular pathogenic antigens). In addition to augmenting T cell activity, the CD8α variants could be used to reduce PD1 and CTLA4-mediated immune suppression by overriding those negative signals (by virtue of the ability of MyD88 to enhance TCR signaling).
- Mutations in the CD8α or CD8β subunits that alter affinity to MHC I can serve as biomarkers to predict patient T cell responses to vaccines or responses by gene modified T cells. Because mutations can either reduce or enhance CD8 affinity, specific mutations could predict both strong and weak responses. For example, patients with K273A and S53N mutations would be expected to show stronger responses.
- Current strategies to enhance T cell responses include:
- antibody-based approaches to prevent T cells from becoming deactivated or prevent their death;
- T cells engineered to express high-affinity TCRs; and
- T cells engineered to expressed chimeric antigen receptors (CAR) that endow T cells with an ability to recognize tumor antigens expressed on the tumor cells surface.

The last two approaches are expensive, time- and labor-intensive processes. The use of high-affinity TCRs could result in the killing of non-cancerous tissues and CAR T cells can only target one antigen. Thus, there is a need for new strategies to enhance T cell responses. The approach described herein avoids the need to identify high-affinity TCRs. Moreover, the CD8α variants of the invention offer the possibility of enhancing the response of T cells carrying low-affinity TCRs, by exploiting the ability of CD8α to amplify TCR signals. Although CAR T cells can only target one antigen, the CD8α variants of the invention could be used as a single platform to enhance the TCR or CAR response against any antigen.

- Vaccine based approaches, such as with dendritic cells, modified tumor cells, tumor lysates, peptide or protein-based vaccines, bacterial or viral vaccines modified to express tumor antigens and other forms of vaccines intended to elicit T cell response.
- Tumor infiltrating lymphocytes for immunotherapy The last two approaches could all benefit from enhancing T cell responses with MyD88 with the invention described herein.

Thus, provided herein are CD8α variants, including but not limited to CD8α-MyD88 fusion proteins and sequence variants thereof, that when introduced into T cells, can serve as TCR co-receptors that augment T cell responses to antigen stimulation. Also provided herein are TCR variants, including but not limited to TCR-MyD88 fusion proteins and sequence variants thereof. These TCR variants can be introduced into T cells to augment T cell responses to weakly immunogenic antigens and/or to further potentiate T cell responses to antigen stimulation.

The present invention is also directed to cells lines expressing the variants and to methods for using the variants and cell lines in vitro and in vivo.

Fusion Proteins

In initial studies it was found that fusing CD8α to the full-length MyD88 protein (or overexpressing MyD88 without CD8α) led to the death of T cells. Without wishing to be bound by theory, it is speculated that this killing occurred in response to chronic and enhanced MyD88 signaling. Because the MyD88 protein contains a region called the TIR domain (Toll/IL-1 receptor domain), which interacts with toll-like receptors (TLR) and IL-1 receptors (IL-1R), it was speculated that removing the TIR domain from MyD88 could prevent clustering to TLRs and IL-1Rs, and thus result in MyD88 activation only upon TCR signaling (or encounter with MHC antigen).

It was further considered that due to the fact that physical interactions between CD8 and MHC I occur through the extracellular domains of CD8, the intracellular portion of the molecule may be less important could potentially be replaced by MyD88 lacking the TIR domain.

As reported below, fusion proteins comprising the extracellular and transmembrane regions of CD8α linked to MyD88 lacking the TIR domain demonstrated excellent properties with respect to increasing T cell proliferation, T cell cytokine and chemokine production, and T cell cytotoxic activity in T cells in which they were expressed. The present invention is directed, in part, to these molecules.

CD8α-MyD88

The present invention thus includes murine and human CD8α variants. In a first aspect the CD8α variants include CD8α-MyD88 fusion proteins comprising extracellular and transmembrane regions of CD8α linked to a region of MyD88 lacking the TIR domain. In a preferred embodiment, these regions are linked as: N-extracellular region of CD8α-transmembrane region of CD8α-MyD88 lacking the TIR domain-C. The CD8α portion of these fusion proteins may be from any mammalian CD8α, including mouse and human. The MyD88 portion of these fusion proteins may also be from any mammalian source, including mouse and human. The extracellular and transmembrane regions of mouse CD8α generally correspond to amino acids 1-217 of mouse CD8α (SEQ ID NO:16; mCD8αΔIC). The extracellular and transmembrane regions of human CD8α generally correspond to amino acids 1-203 of human CD8α (SEQ ID NO:12; hCD8αΔIC). The region of human MyD88 lacking the TIR domain generally corresponds to amino acids 1-155 of human MyD88 (SEQ ID NO:24). Non-limiting examples of these CD8α variants include mCD8α-hMyD88 (SEQ ID NO:17) and hCD8α-hMyD88 (SEQ ID NO:14).

The invention also includes CD8α variants comprising native, full-length CD8α linked to a region of MyD88 lacking the TIR domain. In a preferred embodiment, these regions are linked as: N-CD8α-MyD88 lacking the TIR domain-C. The CD8α portion of these fusion proteins may be any mammalian CD8α, including mouse (SEQ ID NO:15) and human (SEQ ID NO:12). The MyD88 portion of these fusion proteins may also be from any mammalian source, including mouse and human. The region of human MyD88 lacking the TIR domain generally corresponds to amino acids 1-155 of human MyD88 (SEQ ID NO:24).

Each of these CD8α variants may also include more than one of the MyD88 regions lacking the TIR domain linked in tandem, and these MyD88 regions can appear on the N-terminus, the C-terminus, or both the N- and C-termini of the CD8α portion of the fusion proteins.

CD8αTM-MyD88

In a second aspect, the CD8α variants include CD8α-MyD88 fusion proteins comprising only the transmembrane region of CD8α linked to a region of MyD88 lacking the TIR domain. In a preferred embodiment, these regions are linked as: N-transmembrane region of CD8α-MyD88 lacking the TIR domain-C. The CD8α portion of these fusion proteins may be from any mammalian CD8α, including mouse and human. The MyD88 portion of these fusion proteins may also be from any mammalian source, including mouse and human. The transmembrane region of human CD8α generally corresponds to amino acids 128-210 of human CD8α (amino acids 1-83 of SEQ ID NO:18). The region of human MyD88 lacking the TIR domain generally corresponds to amino acids 1-155 of human MyD88 (SEQ ID NO:24). A non-limiting example of this CD8α variant includes hCD8αTM-hMyD88 (SEQ ID NO:18).

Each of these CD8α variants may also include more than one of the MyD88 regions lacking the TIR domain linked in tandem, and these MyD88 regions can appear on the N-terminus, the C-terminus, or both the N- and C-termini of the CD8α portion of the fusion proteins.

CD8α-28-137-3

In a third aspect, the CD8α variants include CD8α fusion proteins comprising the extracellular and transmembrane regions of CD8α linked to the intracellular signaling domains of a traditional $3^{rd}$ generation CAR: human CD28, CD137 (4-1BB), CD3ξ. In a preferred embodiment, these elements are linked as: N-extracellular region of CD8α-transmembrane region of CD8α-CD28-CD137-CD3ξ-C. The CD8α portion of these fusion proteins may be from any mammalian CD8α, including mouse and human. The CD28, CD137 (4-1BB), and CD3ξ intracellular signaling domains may also be from any mammalian source, including mouse and human. The extracellular and transmembrane regions of mouse CD8α generally correspond to amino acids 1-217 of mouse CD8α (SEQ ID NO:16; mCD8αΔIC). The extracellular and transmembrane regions of human CD8α generally correspond to amino acids 1-203 of human CD8α (SEQ ID NO:12; hCD8αΔIC). Human CD28, CD137 (4-1BB), and CD3ξ generally correspond to amino acids 218-417 of SEQ ID NO:19, where CD28 generally corresponds to amino acids 218-256; CD137 (4-1BB) generally corresponds to amino acids 259-305; CD3ξ generally corresponds to amino acids 308-417. A non-limiting example of this CD8α variant includes mCD8α-28-137-3 (SEQ ID NO:19), also referred to herein in some instances as mCD8α-137-28-3.

Each of these CD8α variants may also include more than one of the CD28, CD137 (4-1BB), and CD3ξ intracellular signaling domains linked in tandem, and these intracellular signaling domains can appear on the N-terminus, the C-terminus, or both the N- and C-termini of the CD8α portion of the fusion proteins.

CD4-MyD88

The present invention also includes murine and human CD4 variants. The CD4 variants include CD4-MyD88 fusion proteins comprising extracellular and transmembrane regions of CD4 linked to a region of MyD88 lacking the TIR domain. In a preferred embodiment, these regions are linked as: N-extracellular region of CD4-transmembrane region of CD4-MyD88 lacking the TIR domain-C. The CD4 portion of these fusion proteins may be from any mammalian CD4, including mouse and human. The MyD88 portion of these fusion proteins may also be from any mammalian source, including mouse and human. The extracellular and transmembrane regions of mouse CD4 generally correspond to amino acids 1-417 of mouse CD4 (amino acids 1-417 of SEQ ID NO:21). The extracellular and transmembrane regions of human CD4 generally correspond to amino acids 1-418 of human CD4 (amino acids 1-418 of SEQ ID NO:20). The region of human MyD88 lacking the TIR domain generally corresponds to amino acids 1-155 of human MyD88 (SEQ ID NO:24). Non-limiting examples of these CD4 variants include mCD4-hMyD88 (SEQ ID NO:21) and hCD4-hMyD88 (SEQ ID NO:20).

The invention also includes CD4 variants comprising native, full-length CD4 linked to a region of MyD88 lacking the TIR domain. In a preferred embodiment, these regions are linked as: N-CD4-MyD88 lacking the TIR domain-C. The CD4 portion of these fusion proteins may be any mammalian CD4, including mouse and human. The MyD88 portion of these fusion proteins may also be from any mammalian source, including mouse and human. The region of human MyD88 lacking the TIR domain generally corresponds to amino acids 1-155 of human MyD88 (SEQ ID NO:24).

Each of these CD4 variants may also include more than one of the MyD88 regions lacking the TIR domain linked in tandem, and these MyD88 regions can appear on the N-terminus, the C-terminus, or both the N- and C-termini of the CD4 portion of the fusion proteins.

TCR-MyD88

The present invention also includes murine and human TCR variants. The TCR variants include TCR-MyD88 fusion proteins comprising TCRs linked to a region of MyD88 lacking the TIR domain. In a preferred embodiment, these elements are linked as: N-TCR-MyD88 lacking the TIR domain-C. The TCR portion of these fusion proteins may be from any mammalian TCR, including mouse and human. The MyD88 portion of these fusion proteins may also be from any mammalian source, including mouse and human. In one example, the TCR is the DMF5 TCR. It comprises amino acids 1-603 of SEQ ID NO:22. The region of human MyD88 lacking the TIR domain generally corresponds to amino acids 1-155 of human MyD88 (SEQ ID NO:24). Non-limiting examples of these TCR variants include hTCR-hMyD88 (SEQ ID NO:22).

Linkers and Spacers

As indicated herein, the variants of the invention include fusion proteins comprised of peptide domains and regions from molecules such as CD8α, CD4, MyD88, TCR CD28, CD137 (4-1BB), and CD3ξ. When these domains and regions are linked in the context of a fusion protein, a short linker or spacer may be desirable to enhance formation of a proper three-dimensional structure or shape. The variants of the invention may thus have short peptide linkers or spacers of up to 5, 6, 7, 8, 9, 10, 11, 12, 13, 14, 15, 16, 17, 18, 19, 20, 21, 22, 23, 24, 25 or more amino acids positioned between the functional peptide domains and regions of the fusions proteins.

Sequence Variants
Variations in Length

It will be apparent that the different peptide domains and regions that comprise the variants of the invention can have some amino acid variability without adversely affecting the activity of the variant. For example, the peptide domains and regions can vary somewhat in their length. Thus, while the mouse CD8α-hMyD88 fusion protein is said to comprise amino acids 1-217 of mouse CD8α (SEQ ID NO:15), the length of this portion of the fusion protein may be extended or reduced by a number of amino acids, e.g., to be amino acids 1-210 of SEQ ID NO:15, or amino acids 1-210 of SEQ ID NO:15, or amino acids 10-215 of SEQ ID NO:15, or amino acids 8-222 of SEQ ID NO:15, as only a few examples.

Thus the invention includes sequence variants wherein, for each of the fusion proteins of the invention, the length of the peptide domains and regions used in the fusion proteins can individually be increased or decreased on the amino terminus, carboxy terminus, or both ends, by up to 60, 55, 50, 45, 40, 35, 30, 25, 20, 19, 18, 17, 16, 15, 14, 13, 12, 11, 10, 9, 8, 7, 6, 5, 4, 3, 2, 1 or 0 amino acids based on the native sequence of the polypeptide from which the domain or region is obtained. These sequence variants, in which the peptide domains and regions differ in length from a specific variant defined herein, will have at least 50%, 55%, 60%, 65%, 70%, 75%, 80%, 85%, 90%, 95% or more of the activity of the specific variant upon which they are based. The cytoplasmic domains will generally have 20-1000 amino acids depending on the number of domains and the specific domains to be used. The transmembrane domain will generally have 20-60 amino acids. The extracellular domain will generally have 50-5000 amino acids depending on the number of domains and the specific domains to be used.

Variations in Sequence

It will also be apparent that the variants of the invention can have variability in their amino acid composition without adversely affecting the activity of the variant. For example, the variants can have amino acid additions (conservative and/or non-conservative), deletions and/or substitutions, and any combination thereof. Thus the invention also includes sequence variants having at least 70%, 71%, 72%, 73%, 74%, 75%, 76%, 77%, 78%, 79%, 80%, 81%, 82%, 83%, 85%, 85%, 86%, 87%, 88%, 89%, 90%, 91%, 92%, 93%, 94%, 95%, 96%, 97%, 98%, or 99% sequence identity with a specific variant defined herein, over the entire length of that specific variant. These sequence variants will have at least 50%, 55%, 60%, 65%, 70%, 75%, 80%, 85%, 90%, 95% or more of the activity of the specific variant upon which they are based.

As shown in Example 1 below, variations in the amino acid composition of the variants described herein can be expected to alter or change various attributes and characteristics of immune cells expressing the variants, including their responses when contacting antigen-presenting cells. For example, a K73A mutation in mouse CD8α resulted in a CD8α molecule with higher affinity than the native version of the protein. T cells expressing such "high affinity" CD8α (i.e., CD8α bearing the K73A mutation) showed a higher level of activation that T cells expressing other CD8α variants.

Polynucleotide Sequences

The invention also encompasses the polynucleotide sequences encoding each of the fusion proteins and sequence variants of the invention. Specific polynucleotide sequences encompassed within the scope of the invention include the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88). The skilled artisan will understand that due to the redundancy of the genetic code, there are a large number of different polynucleotide sequences that encode a single polypeptide. The invention includes each polynucleotide sequence encoding a fusion protein or sequence variant of the invention. Thus the invention includes polynucleotide sequences encoding mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and each of the sequence variants thereof encompassed within the scope of the invention.

Cells

The present invention also encompasses cells engineered to produce the variants (i.e., the fusion proteins and sequence variants) of the invention. The identity of such cells is only limited by the ability of the cell to produce the variant. In preferred aspects, the cell can both produce the variant and express it on the surface of the cell. The cells include mammalian cells, such as human or mouse cells, insect cells, and prokaryotic cells, such as bacterial cells.

The variants include fusion proteins mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In another aspect, the variants are encoded by a polynucleotide sequence selected from the polynucleotide sequences set forth in SEQ ID NO:6 (mCD8α-hMyD88), SEQ ID NO:3 (hCD8α-hMyD88), SEQ ID NO:7 (hCD8αTM-hMyD88), SEQ ID NO:8 (mCD8α-28-137-3), SEQ ID NO:10 (mCD4-hMyD88), SEQ ID NO:9 (hCD4-hMyD88) and SEQ ID NO:11 (hTCR-hMyD88), and sequence variants thereof.

In a particular aspect of the invention, these variant-expressing cells may be used in the methods of medical treatment, as discussed herein. Variant-expressing cells used in such methods may be derived from cells autologous, syngeneic or allogeneic to the individual being treated, with the selection dependent on the disease to be treated and the means available to do so. Suitable populations of cells that may be used in the methods include any immune cells with cytolytic activity, such as T cells. Exemplary sub-populations of T cells include, but are not limited to those expressing CD4 such as CD4$^+$ T cells, those expressing CD8 such as CD8⁺ T cells, natural killer T cells (NKT cells), natural killer cells (NK), neutrophils, macrophages, dendritic cells, mast cells, basophils, B cells and other peripheral blood mononuclear cells (PBMC) or other primary or established cell lines including the so-called universal donor cells. The cells may also be isolated from any source, including the blood, lymph node or spleen of a subject, or from a tumor explant of a subject or intratumoral T cells of a subject.

Cells may be engineered to express one or more than one of the variants of the invention. Thus, the invention encompasses populations of cells expressing at least one, two, three or more of the variants of the invention, as well as populations of cells expressing one or more of the variants of the invention.

Cells may be engineered to express the variants of the invention by means readily known to the skilled artisan. Generally, a polynucleotide vector is constructed that encodes the fusion protein or sequence variant and the vector is transfected into a population of cells, such as T cells. The cells are then grown under conditions promoting expression of the fusion protein or sequence variant by the cells. Successful transfection (or transduction which refers to viral-mediated gene integration) and cell-surface display of polypeptides is conducted via conventional means, some of which are disclosed in the Examples herein.

In one aspect, T cells may be engineered to produce the variants by first constructing a retroviral vector encoding a selected fusion protein or sequence variant. An exemplary retroviral vector includes, but is not limited to, the vector backbone pMSGV1-CD8-28BBZ, which is derived from pMSGV (murine stem cell virus-based splice-gag vector). However, other means of gene integration or protein expression, such as nucleofection or transient expression of DNA, RNA or proteins, are also suitable. DNA sequencing can be used to confirm proper construction of the vector before transfection of T cells. Retroviral transduction may be performed using known techniques, such as that of Johnson et al. (Blood 114, 535-546 (2009)). The surface expression of fusion proteins and sequence variants on transduced T cells may be determined, for example, by flow cytometry after staining cells with labeled antibodies.

Immune cells expressing the variants of the present invention have improved attributes in comparison to native immune cells that do not express the variants. For example, expression of the variants in T cells confers T cell resistance to MDSC-mediated suppression. Further, expressing the variants in certain immune cells enhances the ability of those cells to recognize low concentrations of antigens and/or recognize weakly immunogenic antigens. Therefore, the present invention includes methods of conferring resistance in T cells to MDSC-mediated suppression, comprising expressing at least one variant of the present invention in a T cell or population of T cells.

The present invention also includes methods of enhancing the ability of an immune cell to recognize low concentrations of a selected antigen comprising expressing at least one variant of the present invention in an immune cell or population of immune cells. The present invention further includes methods of enhancing the ability of an immune cell to recognize a weakly immunogenic antigen comprising expressing at least one variant of the present invention in an immune cell or population of immune cells. The immune cells include, but are not limited to, T cells (e.g., CD4⁺ and CD8⁺ T cells), natural killer T cells (NKT cells), natural killer cells (NK), neutrophils, macrophages, dendritic cells, mast cells, basophils, B cells and other peripheral blood mononuclear cells (PBMC) or other primary or established cell lines including the so-called universal donor cells.

Cell Administration

Populations of variant-expressing cells may be formulated for administered to a subject using techniques known to the skilled artisan. Formulations comprising variant-expressing cells may include pharmaceutically acceptable excipient(s). Excipients included in the formulations will have different purposes depending, for example, on the nature of the variant being expressed (e.g., CD8α-MyD88 or TCR-MyD88), the subpopulation of T cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising populations of variant-expressing T cells will typically have been prepared and cultured in the absence of any non-human components, such as animal serum (e.g., bovine serum albumin).

A formulation may include one population of variant-expressing cells, or more than one, such as two, three, four, five, six or more different populations of variant-expressing cells. The different populations of variant-expressing cells can vary based on the identity of the variant, the identity of the subpopulation of T cells, or a combination thereof.

The formulations comprising population(s) of variant-expressing cells may be administered to a subject using modes and techniques known to the skilled artisan. Exemplary modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of the formulations can be used to effect such administration.

The formulations comprising population(s) of variant-expressing cells that are administered to a subject comprise a number of variant-expressing cells that is effective for the treatment of the specific indication or disease. Thus, therapeutically-effective amounts of formulations comprising population(s) of variant-expressing cells are administered to subjects when the methods of the present invention are practiced. In general, formulations are administered that comprise between about $1 \times 10^3$ and about $1 \times 10^{10}$ variant-expressing cells. In most cases, the formulation will comprise between about $1 \times 10^3$ and about $1 \times 10^8$ variant-expressing cells, from about $5 \times 10^5$ to about $5 \times 10^8$ variant-expressing cells, or from about $1 \times 10^6$ to about $1 \times 10^7$ variant-expressing cells. However, the number of variant-expressing cells administered to a subject will vary between wide limits, depending upon the location, source, identity, extent and severity of the disease, the age and condition of the individual to be treated, etc. A physician will ultimately determine appropriate dosages to be used.

Methods

Treatment and Prevention of Cancer

CD8⁺ T cells recognize peptides presented on MHC I molecules. Because all nucleated cells including cancer cells express MHC I, virtually any type of cancer can be detected and destroyed by cytotoxic T cells. In some cases, tumor cells can reduce MHC I expression and evade T cell recognition. However, expressing CD8α-MyD88 in T cells offers the advantage of enhancing T cell responses even in the face of low antigen levels or weakly immunogenic antigens.

CD4+ T cells on the other hand recognize peptides presented in the context of an MHC II molecule. Like CD8, CD4 serves as a TCR co-receptor. It is therefore possible that expressing either CD8α-MyD88 or CD4-MyD88 (in either CD8+ T cells or CD4+ T cells, respectively) will augment their responses. Examples of CD4-MyD88 variants are provided herein. It is also possible that since CD8 localizes to the immunological synapse, the area where the TCRs and TCR signaling molecules localize to interact with the MHC on target cells, MyD88 brought to the immunological synapse by any means could also enhance TCR signals. For example, fusing the transmembrane domain of CD8 (or CD4 or any other TCR-signaling related molecule) to the MyD88 can be used to augment T cell responses through localization of MyD88.

The present invention thus encompasses methods of treating a subject having cancer, comprising administering to a subject having cancer a therapeutically-effective amount of a population of cells expressing at least one variant of the present invention. The invention also encompasses methods of treating a subject having cancer, comprising administering to a subject having cancer a therapeutically-effective amount of a formulation comprising at least one population of cells expressing at least one variant of the invention and an excipient.

The present invention also encompasses methods of preventing cancer in a subject, comprising administering to a subject at risk of developing cancer a therapeutically-effective amount of a population of cells expressing at least one variant of the present invention. The invention further encompasses methods of preventing cancer in a subject, comprising administering to a subject at risk of developing cancer a therapeutically-effective amount of a formulation comprising at least one population of cells expressing at least one variant of the invention and an excipient.

The term "cancer" is intended to be broadly interpreted and it encompasses all aspects of abnormal cell growth and/or cell division. Examples include: carcinoma, including but not limited to adenocarcinoma, squamous cell carcinoma, adenosquamous carcinoma, anaplastic carcinoma, large cell carcinoma, small cell carcinoma, and cancer of the skin, breast, prostate, bladder, vagina, cervix, uterus, liver, kidney, pancreas, spleen, lung, trachea, bronchi, colon, small intestine, stomach, esophagus, gall bladder; sarcoma, including but not limited to chondrosarcoma, Ewing's sarcoma, malignant hemangioendothelioma, malignant schwannoma, osteosarcoma, soft tissue sarcoma, and cancers of bone, cartilage, fat, muscle, vascular, and hematopoietic tissues; lymphoma and leukemia, including but not limited to mature B cell neoplasms, such as chronic lymphocytic leukemia/small lymphocytic lymphoma, B-cell prolymphocytic leukemia, lymphomas, and plasma cell neoplasms, mature T cell and natural killer (NK) cell neoplasms, such as T cell prolymphocytic leukemia, T cell large granular lymphocytic leukemia, aggressive NK cell leukemia, and adult T cell leukemia/lymphoma, Hodgkin lymphomas, and immunodeficiency-associated lymphoproliferative disorders; germ cell tumors, including but not limited to testicular and ovarian cancer; blastoma, including but not limited to hepatoblastoma, medulloblastoma, nephroblastoma, neuroblastoma, pancreatoblastoma, leuropulmonary blastoma and retinoblastoma. The term also encompasses benign tumors.

Treatment and Prevention of Infectious Disease

Infectious agents such as viruses and certain bacteria and fungi become internalized by the host cell or by immune cells called professional antigen-presenting cells. The cells process parts of the infectious agents and present them on the cell surface in the context of MHC I, which can then be recognized by T cells. Expressing CD8α-MyD88 in T cells offers the advantage of enhancing T cell responses to any antigen presented on MHC molecules regardless of the source of the antigen. This strategy can be used to augment the immune responses of immunosuppressed individuals, including but not limited to: elderly individuals, patients infected with human immunodeficiency virus (HIV), patients who have been treated with therapies that suppress T cell responses (i.e. steroid therapies, cancer chemotherapies, radiation therapies).

The present invention thus encompasses methods of treating a subject having an infectious disease, comprising administering to a subject having an infectious disease a therapeutically-effective amount of a population of cells expressing at least one variant of the present invention. The invention also encompasses methods of treating a subject having an infectious disease comprising administering to a subject having an infectious disease a therapeutically-effective amount of a formulation comprising at least one population of cells expressing at least one variant of the invention and an excipient.

In addition, the present invention encompasses methods of preventing an infectious disease in a subject, comprising administering to a subject at risk of developing an infectious disease a therapeutically-effective amount of a population of cells expressing at least one variant of the present invention. The invention further encompasses methods of preventing an infectious disease in a subject comprising administering to a subject at risk of developing an infectious disease a therapeutically-effective amount of a formulation comprising at least one population of cells expressing at least one variant of the invention and an excipient.

The identity of the infectious disease is limited only in that antigen-presenting cells have the ability to present antigens derived from the causative agent of the infectious disease on the cell surface in the context of MHC I. Infectious diseases caused by viruses, bacteria and fungi are encompassed within the scope of the invention.

Treatment and Prevention of Autoimmune Disease

The present invention encompasses methods of treating a subject having an autoimmune disorder by targeting for destruction autoreactive cells. Thus included in the invention are methods of treating a subject having an autoimmune disorder, comprising administering to a subject having an autoimmune disorder a therapeutically-effective amount of a population of cells expressing at least one variant of the present invention. The invention also encompasses methods of treating a subject having an autoimmune disorder, comprising administering to a subject having an autoimmune disorder a therapeutically-effective amount of a formulation comprising at least one population of cells expressing at least one variant of the invention and an excipient.

The present invention also encompasses methods for preventing an autoimmune disorder by targeting for destruction autoreactive cells. Thus included in the invention are methods of preventing an autoimmune disorder in a subject, comprising administering to a subject at risk for developing an autoimmune disorder a therapeutically-effective amount of a population of cells expressing at least one variant of the present invention. The invention also encompasses methods of preventing an autoimmune disorder in a subject, comprising administering to a subject at risk of developing an autoimmune disorder a therapeutically-effective amount of a formulation comprising at least one population of cells expressing at least one variant of the invention and an excipient.

The identity of the autoimmune disorder is not limited. However, non-limiting examples include lupus, arthritis, Type I diabetes, multiple sclerosis, Alopecia areata, Celiac disease.

Enhancing Antigen Recognition

The present invention encompasses methods of altering the activity of immune cells, such as T cells, through the engineering of the immune cells to express one or more of the variants of the present invention. For example, expression of the variants in immune cells can provide improvements in the ability of the immune cell to recognize an antigen (e.g., antigens present at a low concentration in a subject or weakly antigenic antigens), including recognition of an antigen in the context of MHC I presentation; activate an effector cell; be activated by an effector cell; remain associated with an antigen-presenting cell; avoid suppression by effector cells, among other examples.

Thus included in the invention are methods of conferring T cell resistance against MDSC-mediated suppression. These methods comprise expressing at least one variant of the present invention in a T cells. In specific aspects, the variants are selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof.

In a related aspect, the invention includes methods of enhancing immune cell recognition of an antigen. These methods comprise expressing at least one variant of the present invention in an immune cell. In specific aspects, the variants are selected from the group consisting of mCD8α-hMyD88 (SEQ ID NO:17), hCD8α-hMyD88 (SEQ ID NO:14), hCD8αTM-hMyD88 (SEQ ID NO:18), mCD8α-28-137-3 (SEQ ID NO:19), mCD4-hMyD88 (SEQ ID NO:21), hCD4-hMyD88 (SEQ ID NO:20) and hTCR-hMyD88 (SEQ ID NO:22), and sequence variants thereof. In certain aspects of this embodiment, the antigen is present at a low concentration in vitro or in vivo, or the antigen is a weakly antigenic antigen, or both.

The immune cells include, but are not limited to, $CD4^+$ T cells, $CD8^+$ T cells, natural killer T cells (NKT cells), natural killer cells (NK), neutrophils, macrophages, dendritic cells, mast cells, basophils, B cells and other peripheral blood mononuclear cells (PBMC), tumor infiltrating lymphocytes or other primary or established cell lines including the so-called universal donor cells.

As used herein, the terms "treat", "treating", and "treatment" have their ordinary and customary meanings, and include one or more of: blocking, ameliorating, or decreasing in severity and/or frequency a symptom of cancer or an infection in a subject, and/or inhibiting the growth, division, spread, or proliferation of cancer cells, bacterial cells or a virus, or progression of cancer (e.g., emergence of new tumors), a bacterial infection or a viral infection in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

As used herein, the terms "prevent", "preventing" and "prevention" have their ordinary and customary meanings, and include one or more of, stopping, averting, avoiding, alleviating or blocking development of cancer or an infection in a subject, and/or stopping, averting, avoiding, alleviating or blocking the growth, division, spread, or proliferation of cancer cells, bacterial cells or a virus, or progression of cancer (e.g., emergence of new tumors), a bacterial infection or a viral infection in a subject. Prevention means stopping by at least about 95% versus a subject to which the prevention has not been administered. Preferably, the stopping is about 100%, about 99%, about 98%, about 97%, about 96% or about 95%. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

Administration frequencies of the formulations comprising populations of variant-expressing cells will vary depending on factors that include the disease or condition being treated, the identity of the variant of the variant-expressing cells, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment will be based on the disease or condition being treated and will be best determined by the attending physician. However, continuation of treatment is contemplated to last for a number of days, weeks, or months.

The invention also provides a kit comprising one or more containers filled with one or more populations of variant-expressing cells. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

III. Examples

Example 1

Figure 2:
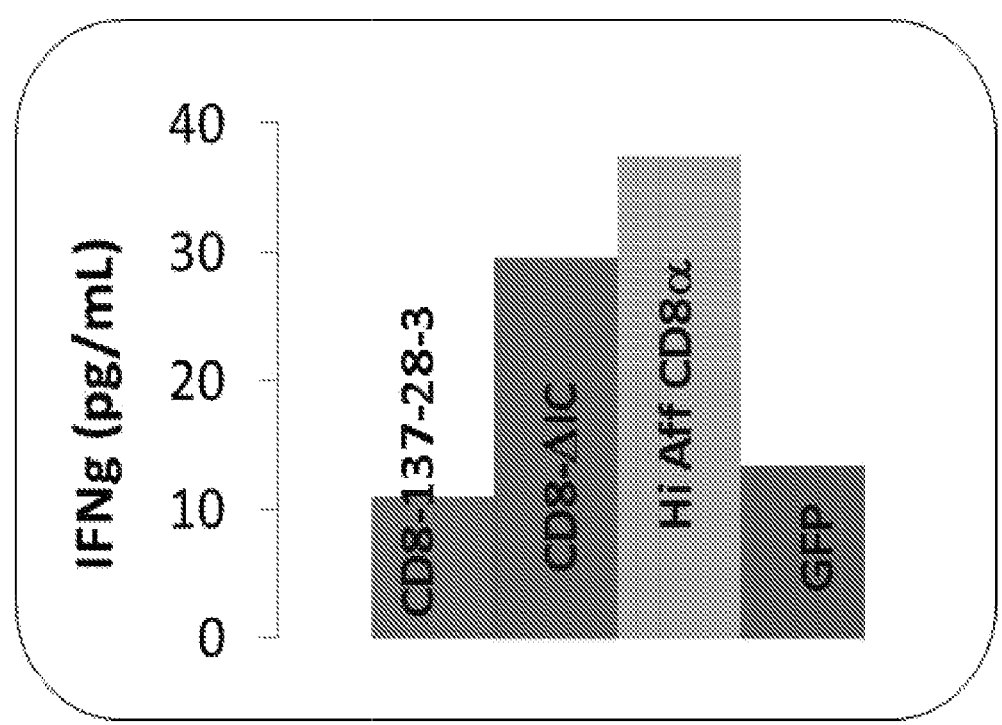
FIG. 2 is a graph showing IFN-γ production by T cells retrovirally transduced with different CD8α variants or a GFP vector control after co-culturing of the T cells with melanoma tumor cells for 24 hours.

To explore the possibility that altering CD8α affinity to the MEW could increase T cell responses, three mouse CD8α variants were prepared. The first variant was a mouse CD8α construct having a K73A mutation ("high affinity CD8α"; SEQ ID NO:23). The second variant was a mouse CD8α construct comprising the extracellular and transmembrane portion of mouse CD8α linked to the 4-1BB-CD28-CD3 intracellular activation domain (mCD8α-28-137-3; SEQ ID NO:19). The third variant was a mouse CD8α construct in which the intracellular domain was deleted (mCD8αΔIC; SEQ ID NO:16). Melanoma-specific $CD8^+$ T cells were engineered via retroviral transduction to express one of these three CD8α variants or a GFP vector control. Approximately 50-60% of $CD8^+$ T cells expressed the vector as indicated by GFP expression (data not shown). IFN-γ production (a measure of T cell activation) was examined after co-culturing T cells with melanoma tumor cells for 24 hours. Upon stimulation, T cells expressing high affinity CD8α (i.e., CD8α bearing the K73A mutation)

showed a higher level of activation that T cells expressing the other CD8α variants (FIG. 2).

```
mCD8α (SEQ ID NO: 23):
MASPLTRFLSLNLLLLGESIILGSGEAKPQAPELRIFPKKMDAELGQKVD

LVCEVLGSVSQGCSWLFQNSSSALPQPTFVVYMASSHNKITWDEKLNSSK

LFSAMRDTNNKYVLTLNKFSKENEGYYFCSVISNSVMYFSSVVPVLQKVN

STTTKPVLRTPSPVHPTGTSQPQRPEDCRPRGSVKGTGLDFACDIYIWAP

LAGICVALLLSLIITLICYHRSRKRVCKCPRPLVRQEGKPRPSEKIV
```

Example 2

Materials and Methods

Mice and Cell Lines.

C57BL6 mice were purchased from the Jackson Laboratory (Bar Harbor, Me., USA), housed in the University of Maryland, Baltimore, specific pathogen-free animal facility and used as recipients for adoptive immunotherapy. Experiments were reviewed and approved by the University of Maryland, Baltimore, Institutional Animal Care and Use Committee.

The mouse melanoma B16 cell line (ATCC, Manassas, Va.) was maintained in Dulbecco's modified Eagle's medium (DMEM) (GIBCO brand; Invitrogen, Carlsbad, Calif., USA) supplemented with 10% heat inactivated fetal bovine serum (Gemini Bio-Products, West Sacramento, Calif., USA), 2 mM L-glutamine (GIBCO brand; Invitrogen) and 1% penicillin-streptomycin (GIBCO brand; Invitrogen). The Phoenix Ecotropic or Amphtropic packaging cell lines were purchased from Orbigen (San Diego, Calif., USA) and maintained in D10 medium containing DMEM, 10% FBS, 1% sodium pyruvate, 2 mM L-glutamine and 1% penicillin-streptomycin.

Construction of CD8 and TCR Variants.

Figure 3:
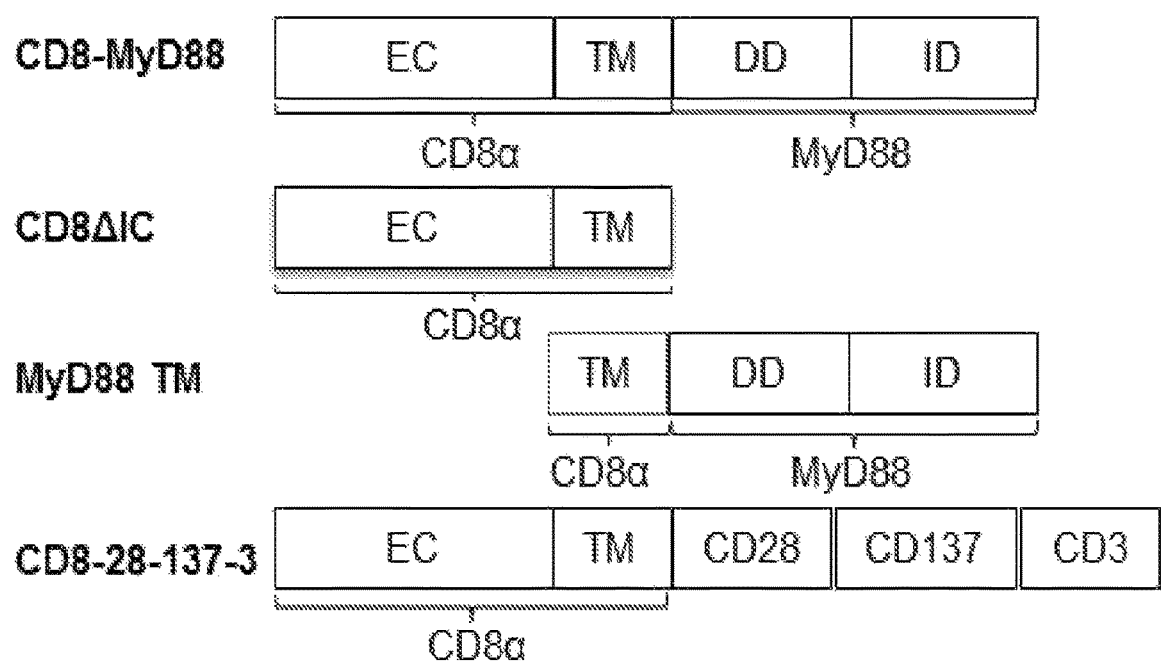
FIG. 3 is a schematic of the CD8α variants of the invention. EC, extracellular domain of CD8α; TM, transmembrane domain of CD8α; DD, death domain of MyD88; ID, intermediate domain of MyD88; CD28, intracellular domain of CD28; CD137, intracellular domain of CD137 (4-1BB); CD3, intracellular domain of CD3ξ.

FIG. 3 shows a schematic representation of the vector constructs, and the order of placement of components in-frame from the 5' to the 3' ends. The CD8α-MyD88 variants were designed by fusing the murine or human CD8α sequence to the human MyD88 death and intermediate domain sequences. The Toll-Interleukin receptor (TIR) domain of the MyD88 molecule was excluded to eliminating binding to endogenous receptors. The CD8α-28-137-3 variants were composed of extracellular murine or human CD8α linked to the intracellular signaling domains of a traditional 3$^{rd}$ generation CAR: CD28, CD137 (4-1BB), CD3ξ. This acts as a control to compare the level of T cell activation with the MyD88 signaling construct. The CD8ΔIC variants are comprised of extracellular and hinge domains of murine or human CD8α and do not contain any intracellular signaling moieties. The MyD88 TM variants are comprised of the death and intermediate domains of MyD88 fused to the transmembrane portion of murine or human CD8α molecules to control for overexpression of MyD88 at the membrane. Genes were and cloned into the pMIG-w vector, which contains a GFP reported downstream of an IRES sequence. The construct was transfected into HEK293 cells and analyzed for CD8α expression via flow cytometry.

T cell receptor (TCR) variants were also produced that comprise of DMF5, a human TCR specific for the MART-1$_{26-35}$ peptide from the MART-1 melanoma antigen presented by MHC I, fused to human MyD88 lacking the TIR domain.

Construction of Retroviral Vectors.

The retroviral vector backbone pMSGV1-CD8-28BBZ (Hughes M. S. et al., Transfer of a T-cell receptor (TCR) gene derived from a patient with a marked antitumor response conveys highly active T-cell effector functions. *Hum Gene Ther* 2005 April; 16(4):457-72) was a kind gift from Dr. Richard Morgan (National Cancer Institute) and is derived from pMSGV (murine stem cell virus-based splice-gag vector).

Mouse CD8α (Genbank NM_001081110.2), human CD8α (Genbank NM_001768.6) and human MyD88 (Genbank NM_001172567.1) were used in the production of retroviral vectors encoding the CD8α variants. The MyD88 nucleotide sequences used refer to a region lacking the Toll/IL-1 receptor (TIR) domain (NM_001172567.1, nucleotides #224-688). The extracellular and transmembrane region of human CD8α (NM_001768.6, nucleotides #890-1498) or mouse CD8α (NM_001081110.2, nucleotides #247-777) were also used.

For construction of the CD4-MyD88 variants, retroviral vectors encoding human (Genbank NM_000616) or mouse (Genbank NM_013488) CD4 linked to MyD88 lacking the TIR domain were prepared.

For construction of the TCR-MyD88 variant, human MyD88 (lacking the TIR domain) was cloned downstream of the human DMF5 TCRαβ chain (TCR alpha chain—Genbank Accession (3QEU_D) and GI (GI:339717586); TCR beta chain—Genbank Accession (3QEU_E) and GI:339717587; see also Johnson et al., *Journal of Immunology.* 2006; 177(9):6548-59)) in the retroviral vector. The DMF5 vector was provided by Dr. Laura Johnson (NCI, Bethesda, Md.; Johnson, L A et al. *Blood* 2009; 114:535-546; Johnson, L A et al. *J. Immunol.* 2006; 177:6548-6559).

The construct sequences were confirmed by DNA sequencing and are as follows:

```
Human CD8α full sequence (hCD8α):gi:225007534:ref:NM_001768.6
(SEQ ID NO: 1):
ATGGCCTTACCAGTGACCGCCTTGCTCCTGCCGCTGGCCTTGCTGCTCCACGCCGCCAG

GCCGAGCCAGTTCCGGGTGTCGCCGCTGGATCGGACCTGGAACCTGGGCGAGAC

AGTGGAGCTGAAGTGCCAGGTGCTGCTGTCCAACCCGACGTCGGGCTGCTCGTGGCT

CTTCCAGCCGCGCGGCGCCGCCGCCAGTCCCACCTTCCTCCTATACCTCTCCCAAAA

CAAGCCCAAGGCGGCCGAGGGGCTGGACACCCAGCGGTTCTCGGGCAAGAGGTTGG

GGGACACCTTCGTCCTCACCCTGAGCGACTTCCGCCGAGAGAACGAGGGCTACTATT

TCTGCTCGGCCCTGAGCAACTCCATCATGTACTTCAGCCACTTCGTGCCGGTCTTCCT

GCCAGCGAAGCCCACCACGACGCCAGCGCCGCGACCACCAACACCGGCGCCCACCA
```

-continued

TCGCGTCGCAGCCCCTGTCCCTGCGCCCAGAGGCGTGCCGGCCAGCGGCGGGGGC

GCAGTGCACACGAGGGGGCTGGACTTCGCCTGTGATATCTACATCTGGGCGCCCTTG

GCCGGGACTTGTGGGGTCCTTCTCCTGTCACTGGTTATCACCCTTTACTGCAACCACA

GGAACCGAAGACGTGTTTGCAAATGTCCCCGGCCTGTGGTCAAATCGGGAGACAAG

CCCAGCCTTTCGGCGAGATACGTC

Human CD8α without the intracellular signaling domain (hCD8αΔIC)
(SEQ ID NO: 2):
ATGGCCTTACCAGTGACCGCCTTGCTCCTGCCGCTGGCCTTGCTGCTCCACGCCGCC

AGGCCGAGCCAGTTCCGGGTGTCGCCGCTGGATCGGACCTGGAACCTGGGCGAGAC

AGTGGAGCTGAAGTGCCAGGTGCTGCTGTCCAACCCGACGTCGGGCTGCTCGTGGCT

CTTCCAGCCGCGCGGCGCCGCCGCCAGTCCCACCTTCCTCCTATACCTCTCCCAAAA

CAAGCCCAAGGCGGCCGAGGGGCTGGACACCCAGCGGTTCTCGGGCAAGAGGTTGG

GGGACACCTTCGTCCTCACCCTGAGCGACTTCCGCCGAGAGAACGAGGGCTACTATT

TCTGCTCGGCCCTGAGCAACTCCATCATGTACTTCAGCCACTTCGTGCCGGTCTTCCT

GCCAGCGAAGCCCACCACGACGCCAGCGCCGCGACCACCAACACCGGCGCCCACCA

TCGCGTCGCAGCCCCTGTCCCTGCGCCCAGAGGCGTGCCGGCCAGCGGCGGGGGC

GCCGGGACTTGTGGGGTCCTTCTCCTGTCACTGGTTATCACC

Human CD8α-MyD88ΔTIR where MyD88 lacks the TIR domain (hCD8α-hMyD88)
(SEQ ID NO: 3):
The underlined section denotes the MyD88 sequence.
ATGGCCTTACCAGTGACCGCCTTGCTCCTGCCGCTGGCCTTGCTGCTCCACGCCGCC

AGGCCGAGCCAGTTCCGGGTGTCGCCGCTGGATCGGACCTGGAACCTGGGCGAGAC

AGTGGAGCTGAAGTGCCAGGTGCTGCTGTCCAACCCGACGTCGGGCTGCTCGTGGCT

CTTCCAGCCGCGCGGCGCCGCCGCCAGTCCCACCTTCCTCCTATACCTCTCCCAAAA

CAAGCCCAAGGCGGCCGAGGGGCTGGACACCCAGCGGTTCTCGGGCAAGAGGTTGG

GGGACACCTTCGTCCTCACCCTGAGCGACTTCCGCCGAGAGAACGAGGGCTACTATT

TCTGCTCGGCCCTGAGCAACTCCATCATGTACTTCAGCCACTTCGTGCCGGTCTTCCT

GCCAGCGAAGCCCACCACGACGCCAGCGCCGCGACCACCAACACCGGCGCCCACCA

TCGCGTCGCAGCCCCTGTCCCTGCGCCCAGAGGCGTGCCGGCCAGCGGCGGGGGC

GCAGTGCACACGAGGGGGCTGGACTTCGCCTGTGATATCTACATCTGGGCGCCCTTG

GCCGGGACTTGTGGGGTCCTTCTCCTGTCACTGGTTATCACC<ins>ATGGCTGCAGGAGGT</ins>

<ins>CCCGGCGCGGGGTCTGCGGCCCCGGTCTCCTCCACATCCTCCCTTCCCCTGGCTGCTC</ins>

<ins>TCAACATGCGAGTGCGGCGCCGCCTGTCTCTGTTCTTGAACGTGCGGACACAGGTGG</ins>

<ins>CGGCCGACTGGACCGCGCTGGCGGAGGAGATGGACTTTGAGTACTTGGAGATCCGG</ins>

<ins>CAACTGGAGACACAAGCGGACCCACTGGCAGGCTGCTGGACGCCTGGCAGGGACG</ins>

<ins>CCCTGGCGCCTCTGTAGGCCGACTGCTCGAGCTGCTTACCAAGCTGGGCCGCGACGA</ins>

<ins>CGTGCTGCTGGAGCTGGGACCCAGCATTGAGGAGGATTGCCAAAAGTATATCTTGA</ins>

<ins>AGCAGCAGCAGGAGGAGGCTGAGAAGCCTTTACAGGTGGCCGCTGTAGACAGCAGT</ins>

<ins>GTCCCACGGACAGCAGAGCTGGCGGGCATCACCACACTTGATGACCCCCTGGGG</ins>

Mouse CD8α full sequence (mCD8α):gi:126722839:ref:001081110.2
(SEQ ID NO: 4):
ATGGCCTCACCGTTGACCCGCTTTCTGTCGCTGAACCTGCTGCTGCTGGGTGAGTCG

ATTATCCTGGGGAGTGGAGAAGCTAAGCCACAGGCACCCGAACTCCGAATCTTTCC

AAAGAAAATGGACGCCGAACTTGGTCAGAAGGTGGACCTGGTATGTGAAGTGTTGG

```
GGTCCGTTTCGCAAGGATGCTCTTGGCTCTTCCAGAACTCCAGCTCCAAACTCCCCC

AGCCCACCTTCGTTGTCTATATGGCTTCATCCCACAACAAGATAACGTGGGACGAGA

AGCTGAATTCGTCGAAACTGTTTTCTGCCATGAGGGACACGAATAATAAGTACGTTC

TCACCCTGAACAAGTTCAGCAAGGAAAACGAAGGCTACTATTTCTGCTCAGTCATCA

GCAACTCGGTGATGTACTTCAGTTCTGTCGTGCCAGTCCTTCAGAAAGTGAACTCTA

CTACTACCAAGCCAGTGCTGCGAACTCCCTCACCTGTGCACCCTACCGGGACATCTC

AGCCCCAGAGACCAGAAGATTGTCGGCCCCGTGGCTCAGTGAAGGGGACCGGATTG

GACTTCGCCTGTGATATTTACATCTGGGCACCCTTGGCCGGAATCTGCGTGGCCCTTC

TGCTGTCCTTGATCATCACTCTCATCTGCTACCACAGGAGCCGAAAGCGTGTTTGCA

AATGTCCCAGGCCGCTAGTCAGACAGGAAGGCAAGCCCAGACCTTCAGAGAAAATT

GTGTAA
```

Mouse CD8α without the intracellular signaling domain (mCD8αΔIC)
(SEQ ID NO: 5):
```
ATGGCCTCACCGTTGACCCGCTTTCTGTCGCTGAACCTGCTGCTGCTGGGTGAGTCG

ATTATCCTGGGGAGTGGAGAAGCTAAGCCACAGGCACCCGAACTCCGAATCTTTCC

AAAGAAAATGGACGCCGAACTTGGTCAGAAGGTGGACCTGGTATGTGAAGTGTTGG

GGTCCGTTTCGCAAGGATGCTCTTGGCTCTTCCAGAACTCCAGCTCCAAACTCCCCC

AGCCCACCTTCGTTGTCTATATGGCTTCATCCCACAACAAGATAACGTGGGACGAGA

AGCTGAATTCGTCGAAACTGTTTTCTGCCATGAGGGACACGAATAATAAGTACGTTC

TCACCCTGAACAAGTTCAGCAAGGAAAACGAAGGCTACTATTTCTGCTCAGTCATCA

GCAACTCGGTGATGTACTTCAGTTCTGTCGTGCCAGTCCTTCAGAAAGTGAACTCTA

CTACTACCAAGCCAGTGCTGCGAACTCCCTCACCTGTGCACCCTACCGGGACATCTC

AGCCCCAGAGACCAGAAGATTGTCGGCCCCGTGGCTCAGTGAAGGGGACCGGATTG

GACTTCGCCTGTGATATTTACATCTGGGCACCCTTGGCCGGAATCTGCGTGGCCCTTC

TGCTGTCCTTGATCATCACTCTCATC
```

Mouse CD8α-human MyD88ΔTIR where MyD88 lacks TIR domain (mCD8α-hMyD88)
(SEQ ID NO: 6):
The underlined section denotes the MyD88 sequence.
```
ATGGCCTCACCGTTGACCCGCTTTCTGTCGCTGAACCTGCTGCTGCTGGGTGAGTCG

ATTATCCTGGGGAGTGGAGAAGCTAAGCCACAGGCACCCGAACTCCGAATCTTTCC

AAAGAAAATGGACGCCGAACTTGGTCAGAAGGTGGACCTGGTATGTGAAGTGTTGG

GGTCCGTTTCGCAAGGATGCTCTTGGCTCTTCCAGAACTCCAGCTCCAAACTCCCCC

AGCCCACCTTCGTTGTCTATATGGCTTCATCCCACAACAAGATAACGTGGGACGAGA

AGCTGAATTCGTCGAAACTGTTTTCTGCCATGAGGGACACGAATAATAAGTACGTTC

TCACCCTGAACAAGTTCAGCAAGGAAAACGAAGGCTACTATTTCTGCTCAGTCATCA

GCAACTCGGTGATGTACTTCAGTTCTGTCGTGCCAGTCCTTCAGAAAGTGAACTCTA

CTACTACCAAGCCAGTGCTGCGAACTCCCTCACCTGTGCACCCTACCGGGACATCTC

AGCCCCAGAGACCAGAAGATTGTCGGCCCCGTGGCTCAGTGAAGGGGACCGGATTG

GACTTCGCCTGTGATATTTACATCTGGGCACCCTTGGCCGGAATCTGCGTGGCCCTTC

TGCTGTCCTTGATCATCACTCTCATCATGGCTGCAGGAGGTCCCGGCGCGGGGTCTG

CGGCCCCGGTCTCCTCCACATCCTCCCTTCCCCTGGCTGCTCTCAACATGCGAGTGCG

GCGCCGCCTGTCTCTGTTCTTGAACGTGCGGACACAGGTGGCGGCCGACTGGACCGC

GCTGGCGGAGGAGATGGACTTTGAGTACTTGGAGATCCGGCAACTGGAGACACAAG
```

CGGACCCCACTGGCAGGCTGCTGGACGCCTGGCAGGGACGCCCTGGCGCCTCTGTA

GGCCGACTGCTCGAGCTGCTTACCAAGCTGGGCCGCGACGACGTGCTGCTGGAGCT

GGGACCCAGCATTGAGGAGGATTGCCAAAAGTATATCTTGAAGCAGCAGCAGGAGG

AGGCTGAGAAGCCTTTACAGGTGGCCGCTGTAGACAGCAGTGTCCCACGGACAGCA

GAGCTGGCGGGCATCACCACACTTGATGACCCCCTGGGG

Human CD8α TM-MyD88 (hCD8αTM-hMyD88) (SEQ ID NO: 7):
This vector lacks the extracellular part of human CD8α but contains
the CD8α transmembrane hinge domain, followed by the human MyD88ΔTIR
intracellular signaling sequence (underlined).
TTCGTGCCGGTCTTCCTGCCAGCGAAGCCCACCACGACGCCAGCGCCGCGACCACCA

ACACCGGCGCCCACCATCGCGTCGCAGCCCCTGTCCCTGCGCCCAGAGGCGTGCCG

GCCAGCGGCGGGGGCGCAGTGCACACGAGGGGGCTGGACTTCGCCTGTGATATCT

ACATCTGGGCGCCCTTGGCCGGGACTTGTGGGGTCCTTCTCCTGTCACTGGTTATCAC

CCTTTACTGCAACCACAGGAACATGGCTGCAGGAGGTCCCGGCGCGGGGTCTGCGG

CCCCGGTCTCCTCCACATCCTCCCTTCCCCTGGCTGCTCTCAACATGCGAGTGCGGCG

CCGCCTGTCTCTGTTCTTGAACGTGCGGACACAGGTGGCGGCCGACTGGACCGCGCT

GGCGGAGGAGATGGACTTTGAGTACTTGGAGATCCGGCAACTGGAGACACAAGCGG

ACCCCACTGGCAGGCTGCTGGACGCCTGGCAGGGACGCCCTGGCGCCTCTGTAGGC

CGACTGCTCGAGCTGCTTACCAAGCTGGGCCGCGACGACGTGCTGCTGGAGCTGGG

ACCCAGCATTGAGGAGGATTGCCAAAAGTATATCTTGAAGCAGCAGCAGGAGGAGG

CTGAGAAGCCTTTACAGGTGGCCGCTGTAGACAGCAGTGTCCCACGGACAGCAGAG

CTGGCGGGCATCACCACACTTGATGACCCCCTGGGG

Mouse CD8α-human CD28-human 41BB-human CD3zeta (mCD8α-28-137-3; in some
instances this same construct is term mCD8α-137-28-3) (SEQ ID NO: 8):
This vector contains extracellular mouse CD8α and transmembrane hinge
domain followed by the human intracellular signaling sequences that
activate CD28, CD137 and the CD3 zeta chain. The CD28 is bold, the 41BB
is double underlined and the CD3zeta is underlined with dotted line.
Linkers are shown with wavy underlines.
ATGGCCTCACCGTTGACCCGCTTTCTGTCGCTGAACCTGCTGCTGCTGGGTGAGTCG

ATTATCCTGGGGAGTGGAGAAGCTAAGCCACAGGCACCCGAACTCCGAATCTTTCC

AAAGAAAATGGACGCCGAACTTGGTCAGAAGGTGGACCTGGTATGTGAAGTGTTGG

GGTCCGTTTCGCAAGGATGCTCTTGGCTCTTCCAGAACTCCAGCTCCAAACTCCCCC

AGCCCACCTTCGTTGTCTATATGGCTTCATCCCACAACAAGATAACGTGGGACGAGA

AGCTGAATTCGTCGAAACTGTTTTCTGCCATGAGGGACACGAATAATAAGTACGTTC

TCACCCTGAACAAGTTCAGCAAGGAAAACGAAGGCTACTATTTCTGCTCAGTCATCA

GCAACTCGGTGATGTACTTCAGTTCTGTCGTGCCAGTCCTTCAGAAAGTGAACTCTA

CTACTACCAAGCCAGTGCTGCGAACTCCCTCACCTGTGCACCCTACCGGGACATCTC

AGCCCCAGAGACCAGAAGATTGTCGGCCCCGTGGCTCAGTGAAGGGGACCGGATTG

GACTTCGCCTGTGATATTTACATCTGGGCACCCTTGGCCGGAATCTGCGTGGCCCTTC

TGCTGTCCTTGATCATCACTCTCATCAGGAGTAAGAGGAGCAGGCTCCTGCACAG

TGACTACATGAACATGACTCCCCGCCGCCCCGGGCCCACCCGCAAGCATTACC

AGCCCTATGCCCCACCACGCGACTTCGCAGCCTATCGCTCCCGTTTCTCTGTTGTT

AAACGGGGCAGAAAGAAGCTCCTGTATATATTCAAACAACCATTTATGAGACCAGT

ACAAACTACTCAAGAGGAAGATGGCTGTAGCTGCCGATTTCCAGAAGAAGAAGAAG

GAGGATGTGAACTGAGAGTGAAGTTCAGCAGGAGCGCAGACGCCCCCGCGTACCAG

CAGGGGCCAGAACCAGCTCTATAACGAGCTCAATCTAGGACGAAGAGAGGAGTACGA

TGTTTTGGACAAGAGACGTGGCCGGGACCCTGAGATGGGGGAAAGCCGAGAAGG

AAGAACCCTCAGGAAGGCCTGTACAATGAACTGCAGAAAGATAAGATGGCGGAGG

CCTACAGTGAGATTGGGATGAAAGGCGAGCGCCGGAGGGGCAAGGGCACGATGG

CCTTTACCAGGGTCTCAGTACAGCCACCAAGGACACCTACGACGCCCTTCACATGCA

GGCCCTGCCCCCTCGCTAA

Human CD4-MyD88ΔTIR where MyD88 lacks the TIR domain (hCD4-hMyD88) (SEQ ID NO: 9): This vector contains extracellular human CD4 (double underline) and transmembrane hinge domain (wavy underline) followed by human MyD88 lacking the TIR domain (single underline).

ATGAACCGGGGAGTCCCTTTTAGGCACTTGCTTCTGGTGCTGCAACTGGCGCTCCTC

CCAGCAGCCACTCAGGGAAAGAAAGTGGTGCTGGGCAAAAAAGGGGATACAGTGG

AACTGACCTGTACAGCTTCCCAGAAGAAGAGCATACAATTCCACTGGAAAAACTCC

AACTAGATAAAGATTCTGGGAAATCAGGGCTCCTTCTTAACTAAAGGTCCATCCAAG

CTGAATGATCGTGCTGACTCAAGAAGAAGCCTTTGGGACCAAGGAAACTTTCCCCTG

ATCATCAAGAATCTTAAGATAGAAGACTCAGATACTTACATCTGTGAAGTGGAGGA

CCAGAAGGAGGAGGTGCAATTGCTAGTGTTCGGATTGACTGCCAACTCTGACACCC

CCTCAGTGCAATGTAGGAGTCCAAGGGGTAAAAACATACAGGGGGGGAAGACCCTC

TCCGTGTCTCAGCTGGAGCTCCAGGATAGTGGCACCTGGACATGCACTGTCTTGCAG

AACCAGAAGAAGGTGGAGTTCAAAATAGACATCGTGGTGCTAGCTTTCCAGAAGGC

CTCCAGCATAGTCTATAAGAAAGAGGGGAACAGGTGGAGTTCTCCTTCCCACTCGC

CTTTACAGTTGAAAAGCTGACGGGCAGTGGCGAGCTGTGGTGGCAGGCGGAGAGGG

CTTCCTCCTCCAAGTCTTGGATCACCTTTGACCTGAAGAACAAGGAAGTGTCTGTAA

AACGGGTTACCCAGGACCCTAAGCTCCAGATGGGCAAGAAGCTCCCGCTCCACCTC

ACCCTGCCCCAGGCCTTGCCTCAGTATGCTGGCTCTGGAAACCTCACCCTGGCCCTT

GAAGCGAAAACAGGAAAGTTGCATCAGGAAGTGAACCTGGTGGTGATGAGAGCCA

CTCAGCTCCAGAAAAATTTGACCTGTGAGGTGTGGGGACCCACCTCCCCTAAGCTGA

TGCTGAGTTTGAAACTGGAGAACAAGGAGGCAAAGGTCTCGAAGCGGGAGAAGGC

GGTGTGGGTGCTGAACCCTGAGGCGGGGATGTGGCAGTGTCTGCTGAGTGACTCGG

GACAGGTCCTGCTGGAATCCAACATCAAGGTTCTGCCCACATGGTCCACCCCGGTGC

AGCCAATGGCCCTGATTGTGCTGGGGGGCGTCGCCGGCCTCCTGCTTTTCATTGGGC

TAGGCATCTTCTTCATGGCTGCAGGAGGTCCCGGCGCGGGGTCTGCGGCCCCGGTCT

CCTCCACATCCTCCCTTCCCCTGGCTGCTCTCAACATGCGAGTGCGGCGCCGCCTGTC

TCTGTTCTTGAACGTGCGGACACAGGTGGCGGCCGACTGGACCGCGCTGGCGGAGG

AGATGGACTTTGAGTACTTGGAGATCCGGCAACTGGAGACACAAGCGGACCCCACT

GGCAGGCTGCTGGACGCCTGGCAGGGACGCCCTGGCGCCTCTGTAGGCCGACTGCT

CGAGCTGCTTACCAAGCTGGGCCGCGACGACGTGCTGCTGGAGCTGGGACCCAGCA

TTGAGGAGGATTGCCAAAAGTATATCTTGAAGCAGCAGCAGGAGGAGGCTGAGAAG

CCTTTACAGGTGGCCGCTGTAGACAGCAGTGTCCCACGGACAGCAGAGCTGGCGGG

CATCACCACACTTGATGACCCCCTGGGGTGA

Mouse CD4-human MyD88ΔTIR where MyD88 lacks the TIR domain
(mCD4-hMyD88) (SEQ ID NO: 10):
This vector contains extracellular mouse CD4 (double underline)
and transmembrane hinge domain (wavy underline) followed by human
MyD88 lacking the TIR domain (single underline).

ATGTGCCGAGCCATCTCTCTTAGGCGCTTGCTGCTGCTGCTGCAGCTGTCACAA

CTCCTAGCTGTCACTCAAGGGAAGACGCTGGTGCTGGGGAAGGAAGGGGAATCAGC

AGAACTGCCCTGCGAGAGTTCCCAGAAGAAGATCACAGTCTTCACCTGGAAGTTCTC

TGACCAGAGGAAGATTCTGGGGCAGCATGGCAAAGGTGTATTAATTAGAGGAGGTT

CGCCTTCGCAGTTTGATCGTTTTGATTCCAAAAAAGGGGCATGGGAGAAAGGATCGT

TTCCTCTCATCATCAATAAACTTAAGATGGAAGACTCTCAGACTTATATCTGTGAGC

TGGAGAACAGGAAAGAGGAGGTGGAGTTGTGGGTGTTCAAAGTGACCTTCAGTCCG

GGTACCAGCCTGTTGCAAGGGCAGAGCCTGACCCTGACCTTGGATAGCAACTCTAA

GGTCTCTAACCCCTTGACAGAGTGCAAACACAAAAAGGGTAAAGTTGTCAGTGGTT

CCAAAGTTCTCTCCATGTCCAACCTAAGGGTTCAGGACAGCGACTTCTGGAACTGCA

CCGTGACCCTGGACCAGAAAAAGAACTGGTTCGGCATGACACTCTCAGTGCTGGGTT

TTCAGAGCACAGCTATCACGGCCTATAAGAGTGAGGGAGAGTCAGCGGAGTTCTCC

TTCCCACTCAACTTTGCAGAGGAAACGGGTGGGAGAGCTGATGTGGAAGGCAGA

GAAGGATTCTTTCTTCCAGCCCTGGATCTCCTTCTCCATAAAGAACAAAGAGGTGTC

CGTACAAAAGTCCACCAAAGACCTCAAGCTCCAGCTGAAGGAAACGCTCCCACTCA

CCCTCAAGATACCCCAGGTCTCGCTTCAGTTTGCTGGTTCTGGCAACCTGACTCTGA

CTCTGGACAAAGGGACACTGCATCAGGAAGTGAACCTGGTGGTGATGAAAGTGGCT

CAGCTCAACAATACTTTGACCTGTGAGGTGATGGGACCTACCTCTCCCAAGATGAGA

CTGACCCTGAAGCAGGAGAACCAGGAGGCCAGGGTCTCTGAGGAGCAGAAAGTAGT

TCAAGTGGTGGCCCCTGAGACAGGGCTGTGGCAGTGTCTACTGAGTGAAGGTGATA

AGGTCAAGATGGACTCCAGGATCCAGGTTTTATCCAGAGGGGTGAACCAGACA

GTGTTCCTGGCTTGCGTGCTGGGTGGCTCCTTCGGCTTTCTGGGTTTCCTTGGGCTCTGCA

TCCTCTGCATGGCTGCAGGAGGTCCCGGCGCGGGGTCTGCGGCCCCGGTCTCCTCCA

CATCCTCCCTTCCCCTGGCTGCTCTCAACATGCGAGTGCGGCGCCGCCTGTCTCTGTT

CTTGAACGTGCGGACACAGGTGGCGGCCGACTGGACCGCGCTGGCGGAGGAGATGG

ACTTTGAGTACTTGGAGATCCGGCAACTGGAGACACAAGCGGACCCCACTGGCAGG

CTGCTGGACGCCTGGCAGGGACGCCCTGGCGCCTCTGTAGGCCGACTGCTCGAGCTG

CTTACCAAGCTGGGCCGCGACGACGTGCTGCTGGAGCTGGGACCCAGCATTGAGGA

GGATTGCCAAAAGTATATCTTGAAGCAGCAGCAGGAGGAGGCTGAGAAGCCTTTAC

AGGTGGCCGCTGTAGACAGCAGTGTCCCACGGACAGCAGAGCTGGCGGGCATCACC

ACACTTGATGACCCCCTGGGGTGA

-continued

Human DMF5 TCR-MyD88 (hTCR-hMyD88) (SEQ ID NO: 11):
The DMF5 T cell receptor, which recognizes the 27-35 nonameric
and 26-35 decameric peptide epitopes from the MART-1 melanoma
antigen presented by MHC I, is fused to human MyD88 lacking
the TIR domain. DMF5 was kindly provided by Dr. Laura Johnson
at the National Cancer Institute and is the same sequence used
in clinical trials registered at www.ClinicalTrials.gov as
NCI-07-C-0174 and NCI-07-C-0175 (Johnson, LA et al. Blood 2009;
114:535-546; Johnson, LA et al. J. Immunol. 2006; 177:6548-6559).
TCRαβ sequence (single underline) is linked to the MyD88 sequence
(double underline).

CCGCCATGATGAAATCCTTGAGAGTTTTACTAGTGATCCTGTGGCTTCAGTTGAGCT

GGGTTTGGAGCCAACAGAAGGAGGTGGAGCAGAATTCTGGACCCCTCAGTGTTCCA

GAGGGAGCCATTGCCTCTCTCAACTGCACTTACAGTGACCGAGGTTCCCAGTCCTTC

TTCTGGTACAGACAATATTCTGGGAAAAGCCCTGAGTTGATAATGTTCATATACTCC

AATGGTGACAAAGAAGATGGAAGGTTTACAGCACAGCTCAATAAAGCCAGCCAGTA

TGTTTCTCTGCTCATCAGAGACTCCCAGCCCAGTGATTCAGCCACCTACCTCTGTGCC

GTGAACTTCGGAGGAGGAAAGCTTATCTTCGGACAGGGAACGGAGTTATCTGTGAA

ACCCAATATCCAGAACCCTGACCCTGCCGTGTACCAGCTGAGAGACTCTAAATCCAG

TGACAAGTCTGTCTGCCTATTCACCGATTTTGATTCTCAAACAAATGTGTCACAAAG

TAAGGATTCTGATGTGTATATCACAGACAAAACTGTGCTAGACATGAGGTCTATGGA

CTTCAAGAGCAACAGTGCTGTGGCCTGGAGCAACAAATCTGACTTTGCATGTGCAAA

CGCCTTCAACAACAGCATTATTCCAGAAGACACCTTCTTCCCCAGCCCAGAAAGTTC

CTGTGATGTCAAGCTGGTCGAGAAAAGCTTTGAAACAGATACGAACCTAAACTTTCA

AAACCTGTCAGTGATTGGGTTCCGAATCCTCCTCCTGAAGGTGGCCGGGTTTAATCT

GCTCATGACGCTGCGGCTGTGGTCCAGCAGAGCCAAAAGAGAGGGCAGAGGAAGTC

TTCTAACATGCGGTGACGTGGAGGAGAATCCCGGCCCTATGAGAATCAGGCTCCTGT

GCTGTGTGGCCTTTTCTCTCCTGTGGGCAGGTCCAGTGATTGCTGGGATCACCCAGG

CACCAACATCTCAGATCCTGGCAGCAGGACGGCGCATGACACTGAGATGTACCCAG

GATATGAGACATAATGCCATGTACTGGTATAGACAAGATCTAGGACTGGGGCTAAG

GCTCATCCATTATTCAAATACTGCAGGTACCACTGGCAAAGGAGAAGTCCCTGATGG

TTATAGTGTCTCCAGAGCAAACACAGATGATTTCCCCCTCACGTTGGCGTCTGCTGT

ACCCTCTCAGACATCTGTGTACTTCTGTGCCAGCAGCCTAAGTTTCGGCACTGAAGC

TTTCTTTGGACAAGGCACCAGACTCACAGTTGTAGAGGACCTGAACAAGGTGTTCCC

ACCCGAGGTCGCTGTGTTTGAGCCATCAGAAGCAGAGATCTCCCACACCCAAAAGG

CCACACTGGTGTGCCTGGCCACAGGCTTCTTCCCTGACCACGTGGAGCTGAGCTGGT

GGGTGAATGGGAAGGAGGTGCACAGTGGGGTCAGCACGGACCCGCAGCCCCTCAA

GGAGCAGCCCGCCCTCAATGACTCCAGATACTGCCTGAGCAGCCGCCTGAGGGTCT

CGGCCACCTTCTGGCAGAACCCCCGCAACCACTTCCGCTGTCAAGTCCAGTTCTACG

GGCTCTCGGAGAATGACGAGTGGACCCAGGATAGGGCCAAACCCGTCACCCAGATC

GTCAGCGCCGAGGCCTGGGGTAGAGCAGACTGTGGCTTTACCTCGGTGTCCTACCAG

CAAGGGGTCCTGTCTGCCACCATCCTCTATGAGATCCTGCTAGGGAAGGCCACCCTG

TATGCTGTGCTGGTCAGCGCCCTTGTGTTGATGGCCATGGTCAAGAGAAAGGATTC

GGATCCATGGCTGCAGGAGGTCCCGGCGCGGGTCTGCGGCCCCGGTCTCCTCCAC

ATCCTCCCTTCCCCTGGCTGCTCTCAACATGCGAGTGCGGCGCCGCCTGTCTCTGTTC

TTGAACGTGCGGACACAGGTGGCGGCCGACTGGACCGCGCTGGCGGAGGAGATGGA

-continued

CTTTGAGTACTTGGAGATCCGGCAACTGGAGACACAAGCGGACCCCACTGGCAGGC

TGCTGGACGCCTGGCAGGGACGCCCTGGCGCCTCTGTAGGCCGACTGCTCGAGCTGC

TTACCAAGCTGGGCCGCGACGACGTGCTGCTGGAGCTGGGACCCAGCATTGAGGAG

GATTGCCAAAAGTATATCTTGAAGCAGCAGCAGGAGGAGGCTGAGAAGCCTTTACA

GGTGGCCGCTGTAGACAGCAGTGTCCCACGGACAGCAGAGCTGGCGGGCATCACCA

CACTTGATGACCCCCTGGGG

Amino acid sequences:
hCD8α(SEQ ID NO: 12):
MALPVTALLLPLALLLHAARPSQFRVSPLDRTWNLGETVELKCQVLLSNPTSGCSWLFQ

PRGAAASPTFLLYLSQNKPKAAEGLDTQRFSGKRLGDTFVLTLSDFRRENEGYYFCSAL

SNSIMYFSHFVPVFLPAKPTTTPAPRPPTPAPTIASQPLSLRPEACRPAAGGAVHTRGLDF

ACDIYIWAPLAGTCGVLLLSLVITLYCNHRNRRRVCKCPRPVVKSGDKPSLSARYV hCD8αΔIC (SEQ ID NO: 13):
MALPVTALLLPLALLLHAARPSQFRVSPLDRTWNLGETVELKCQVLLSNPTSGCSWLFQ

PRGAAASPTFLLYLSQNKPKAAEGLDTQRFSGKRLGDTFVLTLSDFRRENEGYYFCSAL

SNSIMYFSHFVPVFLPAKPTTTPAPRPPTPAPTIASQPLSLRPEACRPAAGGAVHTRGLDF

ACDIYIWAPLAGTCGVLLLSLVIT hCD8α-hMyD88; MyD88 lacks the TIR domain (SEQ ID NO: 14):
MALPVTALLLPLALLLHAARPSQFRVSPLDRTWNLGETVELKCQVLLSNPTSGCSWLFQ

PRGAAASPTFLLYLSQNKPKAAEGLDTQRFSGKRLGDTFVLTLSDFRRENEGYYFCSAL

SNSIMYFSHFVPVFLPAKPTTTPAPRPPTPAPTIASQPLSLRPEACRPAAGGAVHTRGLDF

ACDIYIWAPLAGTCGVLLLSLVITMAAGGPGAGSAAPVSSTSSLPLAALNMRVRRRLSLF

LNVRTQVAADWTALAEEMDFEYLEIRQLETQADPTGRLLDAWQGRPGASVGRLLELLT

KLGRDDVLLELGPSIEEDCQKYILKQQQEEAEKPLQVAAVDSSVPRTAELAGITTLDDPL

G mCD8α (SEQ ID NO: 15):
MASPLTRFLSLNLLLLGESIILGSGEAKPQAPELRIFPKKMDAELGQKVDLVCEVLGSVS

QGCSWLFQNSSSKLPQPTFVVYMASSHNKITWDEKLNSSKLFSAMRDTNNKYVLTLNK

FSKENEGYYFCSVISNSVMYFSSVVPVLQKVNSTTTKPVLRTPSPVHPTGTSQPQRPEDC

RPRGSVKGTGLDFACDIYIWAPLAGICVALLLSLIITLICYHRSRKRVCKCPRPLVROEGK

PRPSEKIV mCD8αΔIC (SEQ ID NO: 16):
MASPLTRFLSLNLLLLGESIILGSGEAKPQAPELRIFPKKMDAELGQKVDLVCEVLGSVS

QGCSWLFQNSSSKLPQPTFVVYMASSHNKITWDEKLNSSKLFSAMRDTNNKYVLTLNK

FSKENEGYYFCSVISNSVMYFSSVVPVLQKVNSTTTKPVLRTPSPVHPTGTSQPQRPEDC

RPRGSVKGTGLDFACDIYIWAPLAGICVALLLSLIITLI mCD8α-hMyD88; MyD88 lacks the TIR domain (SEQ ID NO: 17):
The underlined section denotes the MyD88 sequence.
MASPLTRFLSLNLLLLGESIILGSGEAKPQAPELRIFPKKMDAELGQKVDLVCEVLGSVS

QGCSWLFQNSSSKLPQPTFVVYMASSHNKITWDEKLNSSKLFSAMRDTNNKYVLTLNK

FSKENEGYYFCSVISNSVMYFSSVVPVLQKVNSTTTKPVLRTPSPVHPTGTSQPQRPEDC

RPRGSVKGTGLDFACDIYIWAPLAGICVALLLSLIITLIMAAGGPGAGSAAPVSSTSSLPL

AALNMRVRRRLSLFLNVRTQVAADWTALAEEMDFEYLEIRQLETQADPTGRLLDAWQ

GRPGASVGRLLELLTKLGRDDVLLELGPSIEEDCQKYILKQQQEEAEKPLQVAAVDSSVP

RTAELAGITTLDDPLG hCD8αTM-hMyD88 (SEQ ID NO: 18):
CD8α transmembrane hinge domain, followed by the human MyD88ΔTIR
intracellular signaling sequence (underlined).
FVPVFLPAKPTTTPAPRPPTPAPTIASQPLSLRPEACRPAAGGAVHTRGLDFACDIYIWAP

LAGTCGVLLLSLVITLYCNHRNMAAGGPGAGSAAPVSSTSSLPLAALNMRVRRRLSLFL

NVRTQVAADWTALAEEMDFEYLEIRQLETQADPTGRLLDAWQGRPGASVGRLLELLTK

LGRDDVLLELGPSIEEDCQKYILKQQQEEAEKPLQVAAVDSSVPRTAELAGITTLDDPLG mCD8α-28-137-ζ (and mCD8α-137-28-ζ) (SEQ ID NO: 19):
Extracellular mouse CD8α and transmembrane hinge domain, followed
by the human intracellular signaling sequences that activate CD28
(bold), CD137 (double underlined) and the CD3 zeta chain (dotted
line). Linkers are shown with wavy underlines.
MASPLTRFLSLNLLLLGESIILGSGEAKPQAPELRIFPKKMDAELGQKVDLVCEVLGSVS

QGCSWLFQNSSSKLPQPTFVVYMASSHNKITWDEKLNSSKLFSAMRDTNNKYVLTLNK

FSKENEGYYFCSVISNSVMYFSSVVPVLQKVNSTTTKPVLRTPSPVHPTGTSQPQRPEDC

RPRGSVKGTGLDFACDIYIWAPLAGICVALLLSLIITLIRSKRSRLLHSDYMNMTPRRPG

PTRKHYQPYAPPRDFAAYRSRFSVVKRGRKKLLYIFKQPFMRPVQTTQEEDGCSCRFP

EEEEGGCELRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATKDTYDALH

MQALPPR hCD4-hMyD88 (SEQ ID NO: 20):
Human CD4 extracellular (double underline) and transmembrane
hinge domains (wavy underline) followed by human MyD88 lacking
the TIR domain (single underline).
MNRGVPFRHLLLVLQLALLPAATQGKKVVLGKKGDTVELTCTASQKKSIQFHWKNSNQ

IKILGNQGSFLTKGPSKLNDRADSRRSLWDQGNFPLIIKNLKIEDSDTYICEVEDQKEEVQ

LLVFGLTANSDTHLLQGQSLTLTLESPPGSSPSVQCRSPRGKNIQGGKTLSVSQLELQDS

GTWTCTVLQNQKKVEFKIDIVVLAFQKASSIVYKKEGEQVEFSFPLAFTVEKLTGSGEL

WWQAERASSSKSWITFDLKNKEVSVKRVTQDPKLQMGKKLPLHLTLPQALPQYAGSG

NLTLALEAKTGKLHQEVNLVVMRATQLQKNLTCEVWGPTSPKLMLSLKLENKEAKVS

KREKAVWVLNPEAGMWQCLLSDSGQVLLESNIKVLPTWSTPVQPMALIVLGGVAGLLL

FIGLGIFFMAAGGPGAGSAAPVSSTSSLPLAALNMRVRRRLSLFLNVRTQVAADWTALA

EEMDFEYLEIRQLETQADPTGRLLDAWQGRPGASVGRLLELLTKLGRDDVLLELGPSIEE

DCQKYILKQQQEEAEKPLQVAAVDSSVPRTAELAGITTLDDPLG mCD4-hMyD88 (SEQ ID NO: 21):
Mouse CD4 extracellular (double underline) and transmembrane
hinge domains (wavy underline) followed by human MyD88 lacking
the TIR domain (single underline).
MCRAISLRRLLLLLLQLSQLLAVTQGKTLVLGKEGESAELPCESS0KKITVFTWKFSDQR

KILGQHGKGVLIRGGSPSQFDRFDSKKGAWEKGSFPLIINKLKMEDSQTYICELENRKEE

VELWVFKVTFSPGTSLLQGQSLTLTLDSNSKVSNPLTECHHKKGKVVSGSKVLSMSNLR

VQDSDFWNCTVTLDQKKNWFGMTLSVLGFQSTAITAYKSEGESAEFSFPLNFAEENGW

GELMWKAEKDSFFQPWISFSIKNKEVSVQKSTKDLKLQLKETLPLTLKIPQVSLQFAGSG

NLTLTLDKGTLHQEVNLVVMKVAQLNNTLTCEVMGPTSPKMRLTLKQENQEARVSEE

-continued
QKVVQVVAPETGLWQCLLSEGDKVKMDSRIQVLSRGVNQTVFLACVLGGSFGFLGFLG

LCILCMAAGGPGAGSAAPVSSTSSLPLAALNMRVRRRLSLFLNVRTQVAADWTALAEE

MDFEYLEIRQLETQADPTGRLLDAWQGRPGASVGRLLELLTKLGRDDVLLELGPSIEED

CQKYILKQQQEEAEKPLQVAAVDSSVPRTAELAGITTLDDPLG hTCR-hMyD88 (SEQ ID NO: 22):
TCRαβ sequence (single underline) is linked to the MyD88 sequence
(double underline).
MMKSLRVLLVILWLQLSWVWSQQKEVEQNSGPLSVPEGAIASLNCTYSDRGSQSFFWY

RQYSGKSPELIMFIYSNGDKEDGRFTAQLNKASQYVSLLIRDSQPSDSATYLCAVNFGGG

KLIFGQGTELSVKPNIQNPDPAVYQLRDSKSSDKSVCLFTDFDSQTNVSQSKDSDVYITD

KTVLDMRSMDFKSNSAVAWSNKSDFACANAFNNSIIPEDTFFPSPESSCDVKLVEKSFET

DTNLNFQNLSVIGFRILLLKVAGFNLLMTLRLWSSRAKREGRGSLLTCGDVEENPGPMRI

RLLCCVAFSLLWAGPVIAGITQAPTSQILAAGRRMTLRCTQDMRHNAMYWYRQDLGLG

LRLIHYSNTAGTTGKGEVPDGYSVSRANTDDFPLTLASAVPSQTSVYFCASSLSFGTEAF

FGQGTRLTVVEDLNKVFPPEVAVFEPSEAEISHTQKATLVCLATGFFPDHVELSWWVNG

KEVHSGVSTDPQPLKEQPALNDSRYCLSSRLRVSATFWQNPRNHFRCQVQFYGLSENDE

WTQDRAKPVTQIVSAEAWGRADCGFTSVSYQQGVLSATILYEILLGKATLYAVLVSALV

LMAMVKRKDFGSMAAGGPGAGSAAPVSSTSSLPLAALNMRVRRRLSLFLNVRTQVAA

DWTALAEEMDFEYLEIRQLETQADPTGRLLDAWQGRPGASVGRLLELLTKLGRDDVLL

ELGPSIEEDCQKYILKQQQEEAEKPLQVAAVDSSVPRTAELAGITTLDDPLGGS

Human MyD88 (SEQ ID NO: 24):
MAAGGPGAGSAAPVSSTSSLPLAALNMRVRRRLSLFLNVRTQVAADWTALAEEMDFE

YLEIRQLETQADPTGRLLDAWQGRPGASVGRLLELLTKLGRDDVLLELGPSIEEDCQKYI

LKQQQEEAEKPLQVAAVDSSVPRTAELAGITTLDDPLGHMPERFDAFICYCPSDIQFVQE

MIRQLEQTNYRLKLCVSDRDVLPGTCVWSIASELIEKRCRRMVVVVSDDYLQSKECDFQ

TKFALSLSPGAHQKRLIPIKYKAMKKEFPSILRFITVCDYTNPCTKSWFWTRLAKALSLP

Transfection of HEK Cells.

That the mouse CD8α variant could be properly expressed in the cell membrane was confirmed using in human endothelial kidney cells (HEK; ATCC, Manassas, Va.). HEK cells were maintained in Dulbecco's modified Eagle's medium (DMEM) (GIBCO brand; Invitrogen, Carlsbad, Calif., USA) supplemented with 10% heat inactivated fetal bovine serum (Gemini Bio-Products, West Sacramento, Calif., USA), 2 mM L-glutamine (GIBCO brand; Invitrogen) and 1% penicillin-streptomycin (GIBCO brand; Invitrogen). The day before transfection, the cells were trypsinized and counted. $0.5 \times 10^5$ cells/ml were plated at a cell density of 50% confluency. Cells were transfected with 2.5 μg of DNA encoding mCD8α in 100 μl of Opti-MEM® I Reduced Serum Media without serum and 0.5 μl of Lipofectamine LTX (LIFE Technologies, Grand Island, N.Y.) according to the manufacturer's protocol. After a 30 minute incubation, 100 μl of the DNA-Lipofectamine LTX Reagent complexes were added directly to each well containing cells and mixed gently by rocking the plate back and forth. 48 hours after transfection the expression of CD8α was determined by flow cytometry.

Retroviral Transduction of T Cells.

Spleen and lymph node—derived mouse pmel T cells (Jackson Laboratory) were activated using plate bound anti-CD3 (5 ug/ml) and anti-CD28 Ab (2.5 ug/ml) (BD Biosciences, Franklin Lakes, N.J., USA) for two days while T cell receptors specific for the mouse $gp100_{25-33}$ antigen expression were activated by adding 1 ug/ml of $gp100_{25-33}$ peptide. Two days later cells were collected for retroviral transduction. For transduction, 24-well non-tissue culture treated plates (BD Biosciences, Franklin Lakes, N.J., USA) were coated with 0.5 ml per well of 10 μg/ml recombinant human fibronectin fragment (RetroNectin; Takara, Otsu, Shiga, Japan) overnight at 4° C. After incubation, wells were blocked with 1 ml of Hank's balanced salt solution (GIBCO brand; Invitrogen) plus 2.5% human AB serum for 30 min at RT, and washed with Hank's balanced salt solution plus 2.5% N-2-hydroxyethylpiperazine-N'-2-ethanesulfonic acid (HEPES) (GIBCO brand; Invitrogen).

Transductions were conducted as previously described (Johnson et al. *Blood* 114, 535-546 (2009)). Briefly, approximately 2.5 ml of retroviral supernatant were added to each coated well followed by centrifugation at 2000 g for 2 h at 32° C. 1.5 ml of viral supernatant was removed and $1 \times 10^6$ (0.5 ml) activated T cells were added to each well in the presence of 100 U/ml IL-2. Plates were centrifugated at 1000 g for 10 min, and then incubated overnight at 37° C. After transduction, cells were washed and maintained in the presence of IL-2 (100 U/ml) and used in experiments five days after transduction. The transduction efficiencies are determined by evaluating the percentage of T cells positive for green fluorescent protein (GFP+), as the MGSV vector used contains a gene that encodes GFP. The plasmid is referred to as pMIG and was purchased from Addgene (Cambridge, Mass.). The successful transduction of T cells was confirmed by the expression of GFP which is located downstream of the CD8, CD4 and TCR constructs.

For transduction of human T cells, peripheral blood mononuclear cells (PBMC) from healthy donors were purchased from Biological Specialty Corp (Colmar, Pa., USA), and isolated by Ficoll-Pague (GE Healthcare, Piscataway, N.J., USA) density gradient centrifugation. Isolated PBMC were cultured at $3 \times 10^6$ per well in 24-well tissue culture plates in AIM V medium (GIBCO brand; Invitrogen) supplemented with 5% human AB serum (Sigma-Aldrich), 1% MEM non-essential amino acids, 1% penicillin-streptomycin and 100 U/ml recombinant human IL-2 (BioLegend, San Diego, Calif., USA), and activated with 50 ng/ml OKT3 (eBioscience, San Diego, Calif., USA). Two days later, cells were collected for retroviral transduction.

For transduction, 24-well non-tissue culture treated plates (BD Biosciences, Franklin Lakes, N.J., USA) were coated with 0.5 ml per well of 10 µg/ml recombinant human fibronectin fragment (RetroNectin; Takara, Otsu, Shiga, Japan) overnight at 4° C. After incubation, wells were blocked with 1 ml of Hank's balanced salt solution (GIBCO brand; Invitrogen) plus 2.5% human AB serum for 30 min at RT, and washed with Hank's balanced salt solution plus 2.5% N-2-hydroxyethylpiperazine-N'-2-ethanesulfonic acid (HEPES) (GIBCO brand; Invitrogen).

Transductions were conducted as previously described (Johnson et al. *Blood* 114, 535-546 (2009)). Briefly, approximately 2.5 ml of retroviral supernatant were added to each coated well followed by centrifugation at 2000 g for 2 h at 32° C. 1.5 ml of viral supernatant was removed and $1 \times 10^6$ (0.5 ml) activated PBMC were added to each well in the presence of 100 U/ml IL-2. Plates were centrifuged at 1000 g for 10 min, and then incubated overnight at 37° C. After transduction, cells were washed and maintained in the presence of IL-2 (100 U/ml) and used in experiments five days after transduction. The surface expression of DMF5 on transduced human T cells was determined by flow cytometry after staining cells with CD8 and MART-1 MHC tetramers.

NF-κB Activation Assay.

TLR4-expressing HEK-Blue cells were cultured in DMEM 10% FBS 1% PenStrep 1×HEK-Blue Solution (InvivoGen). Cells were plated at $1 \times 10^6$ cells per well in a 6-well plate in antibiotic-free media and cultured at 37° C./5% $CO_2$ overnight. Cells were transfected with Lipofectamine 2000 (Invitrogen) with 4 µg DNA. 24 hours later, cells were collected and aliquoted at 50,000 cells per well in a 96-well plate in quadruplicate. 50 ug/mL of LPS (Invitrogen) was used as a positive control. Cell supernatant was collected after 24 hours and combined with QUANTI-Blue reagent (InvivoGen). Absorbance was measured at 620 nm after 3 hours. These cells were used to evaluate the ability of the different CD8 constructs to activate NF-kB and used as a surrogate for CD8 function.

T Cell Proliferation Assay, Cytokine and Chemokine Production Assay.

Three to five days after transduction, $1 \times 10^5$ T cells were cultured in 96-well round-bottom plates with B16 tumor cells or with mouse splenocytes pulsed with gp100$_{25-33}$ peptide. $1 \times 10^5$ effector T cells and $1 \times 10^5$ tumor cells were co-cultured in 200 µl of culture volume in 96-well round-bottom plates for 72 h. Sixteen hours before harvesting, 0.5 µCi of 3H-thymidine was added to each well prior to measuring thymidine uptake using a 1450 LSC & luminescence counter (PerkinElmer, Waltham, Mass., USA). Cytokine and chemokine production levels were measured from culture supernatants collected 48 hours after stimulation using a Cytokine/Chemokine kit (Millipore, Billerica, Mass., USA) according to manufacturer's instructions. For studies examining the costimulatory effects of MyD88 when fused to a tumor-reactive T cell receptor (TCR), human T cells transduced with the $1 \times 10^5$ effector T cells DMF5 or DMF5-MyD88 were co-cultured with $1 \times 10^5$ human Malm-3M melanoma tumor cells in 96-well round-bottom plates in 200 µl of culture volume in 96-well round-bottom plates for 72 h. Sixteen hours before harvesting, 0.5 µCi of 3H-thymidine was added to each well prior to measuring thymidine uptake using a 1450 LSC & luminescence counter (PerkinElmer, Waltham, Mass., USA).

Cytotoxicity Assay.

Cytotoxic activity against tumor target cells was measured using a standard $^{51}$Cr release assay. Target cells were labeled with 200 µCi of $^{51}$Cr for 2 h at 37° C., washed 3 times, and pulsed with anti-human antibodies for 1 h at 37° C. $1 \times 10^4$ labeled target cells were then co-cultured with decreasing numbers of effector T cells at the indicated effector to target (E:T) ratios in 200 µl of culture volume in 96-well round-bottom plates. Target cells incubated in media alone were used to determined spontaneous $^{51}$Cr release, and maximal release was determined by incubating labeled target cells in 10% Triton X-100. After 5 hours at 37° C., 50 µl of supernatant was collected and $^{51}$Cr radioactivity was measured in a 1450 LSC & luminescence counter. The mean percentage of specific lysis was calculated according to the following equation: % specific lysis=(test release−spontaneous release)/(maximal release−spontaneous release)×100. All tests were performed in triplicate wells and results are shown as mean±SD. In other experiments, a non-radioactive cytotoxicity kit was used (Promega, Madison, Wis.).

MDSC Suppression Assays.

Myeloid-derived suppressor cells (MDSC; as characterized be expression of CD11b+Gr1+) were collected from the blood of mice with established B16-GMCSF melanoma tumors. MDSCs were irradiated (10,000 rads; gamma-radiation source) and co-cultured with T cells engineered to express CD8α-MyD88 or a control vector (GFP) in 96-well round bottom plates. $1 \times 10^5$ T cells were cultured with $1 \times 10^5$ or $2.5 \times 10^5$ MDSCs for 48 hours. Sixteen hours before harvesting, 0.5 µCi of 3H-thymidine was added to each well prior to measuring thymidine uptake using a 1450 LSC & luminescence counter (PerkinElmer, Waltham, Mass., USA).

Results

Experiment 2A.

Figures 4A, 4B:
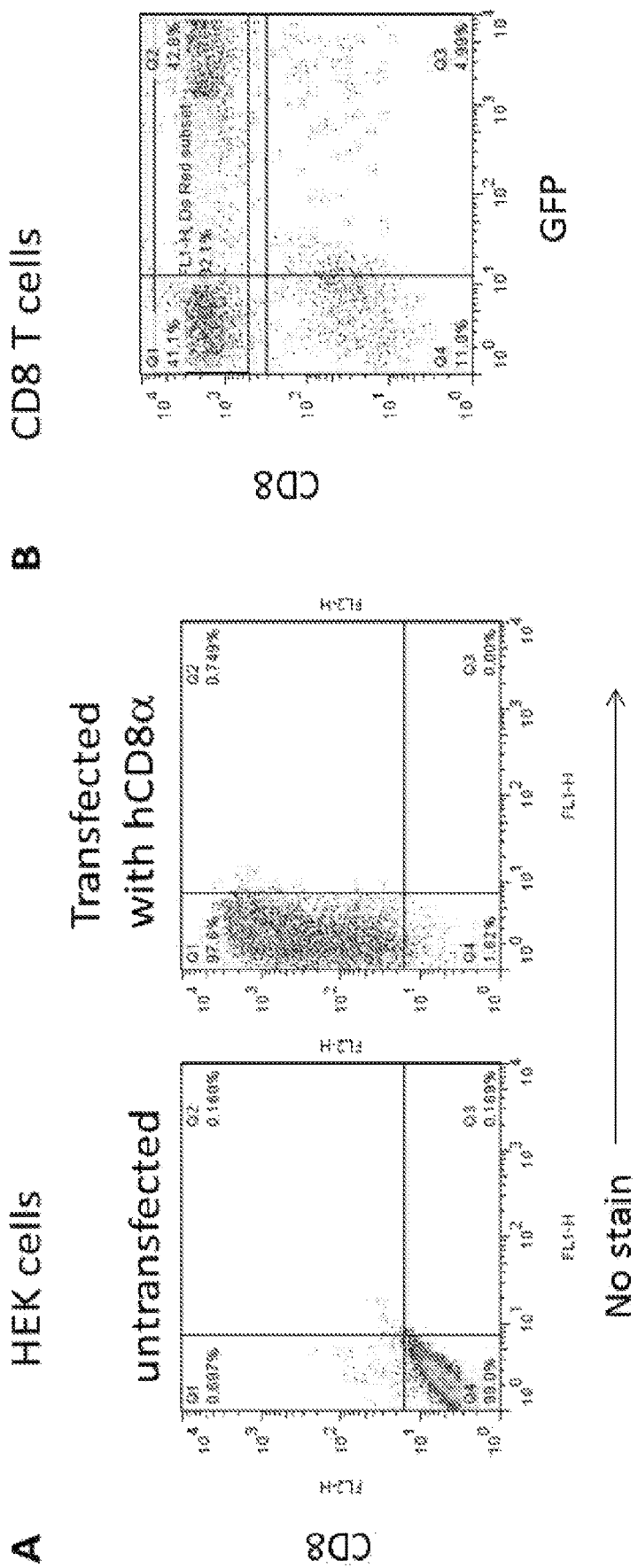
FIGS. 4A-4B. CD8α expression and transduction efficiency in HEK and CD8+ T cells.

CD8α expression was confirmed in CD8α-transfected HEK cells (which do not express endogenous CD8α). As shown in FIG. 4A, CD8α was detected on virtually 100% of HEK cells, indicating the successful expression and translocation of CD8α to the cell surface. The transduction efficiency in mouse CD8+ T cells was also confirmed by flow cytometry. The data in FIG. 4B demonstrates an average CD8+ T cell transduction efficiency of approximately 50% (of all CD8+ T cells).

Experiment 2B.

Figure 5:
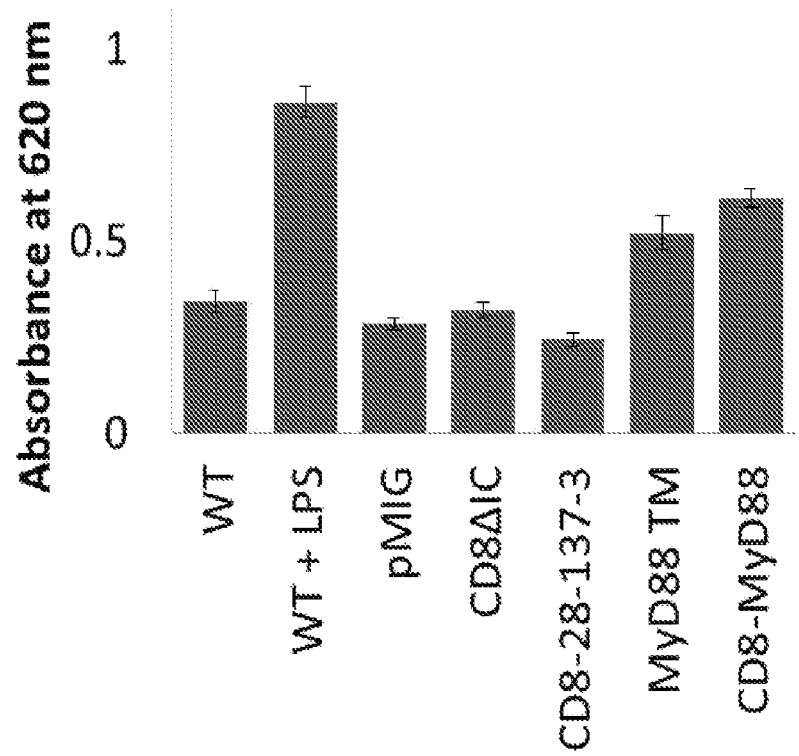
FIG. 5. MyD88 signaling activates NF-κB. HEK-Blue reporter cells were transiently transfected with the constructs. SEAP activity was determined as a readout for NF-κB activation at 48 hours, measured by change in absorbance at 620 nm. LPS serves as a positive control, pMIG is the empty vector control.

The ability of MyD88 to induce signaling in HEK-Blue cells was determined. As can be seen from FIG. 5, HEK-Blue cells expressing mCD8α fused to hMyD88 (lacking the TIR domain) (CD8-MyD88) or expressing MyD88 linked to the transmembrane hinge domain of mCD8α (MyD88TM)

exhibit higher levels of NK-κB activation in comparison to cells expressing an mCD8α variant having only the extracellular region and transmembrane hinge domain of mCD8α (CD8ΔIC) or the extracellular region and transmembrane hinge domain of CD8α linked to 28-137-3 (CD8-28-137-3). The levels of NK-κB activation by CD8ΔIC or CD8-28-137-3 were similar to cells engineered with control vectors (pMIG) or untransduced cells (WT).

Experiment 2B.

The ability of MyD88 to induce signaling in HEK-Blue cells was determined. As can be seen from FIG. 5, HEK-Blue cells expressing mCD8α fused to hMyD88 (lacking the TIR domain) (CD8-MyD88) or expressing MyD88 linked to the transmembrane hinge domain of mCD8α exhibit higher levels of NK-κB activation in comparison to cells expressing an mCD8α variant having only the transmembrane hinge domain of mCD8α (CD8ΔIC) or the CD8α linked to 28-137-3 (CD8-28-137-3). The levels of NK-κB activation by CD8ΔIC or CD8-28-137-3 were similar to cells engineered with control vectors (pMIG) or untransduced cells (WT).

Experiment 2C.

Figures 6A, 6B:
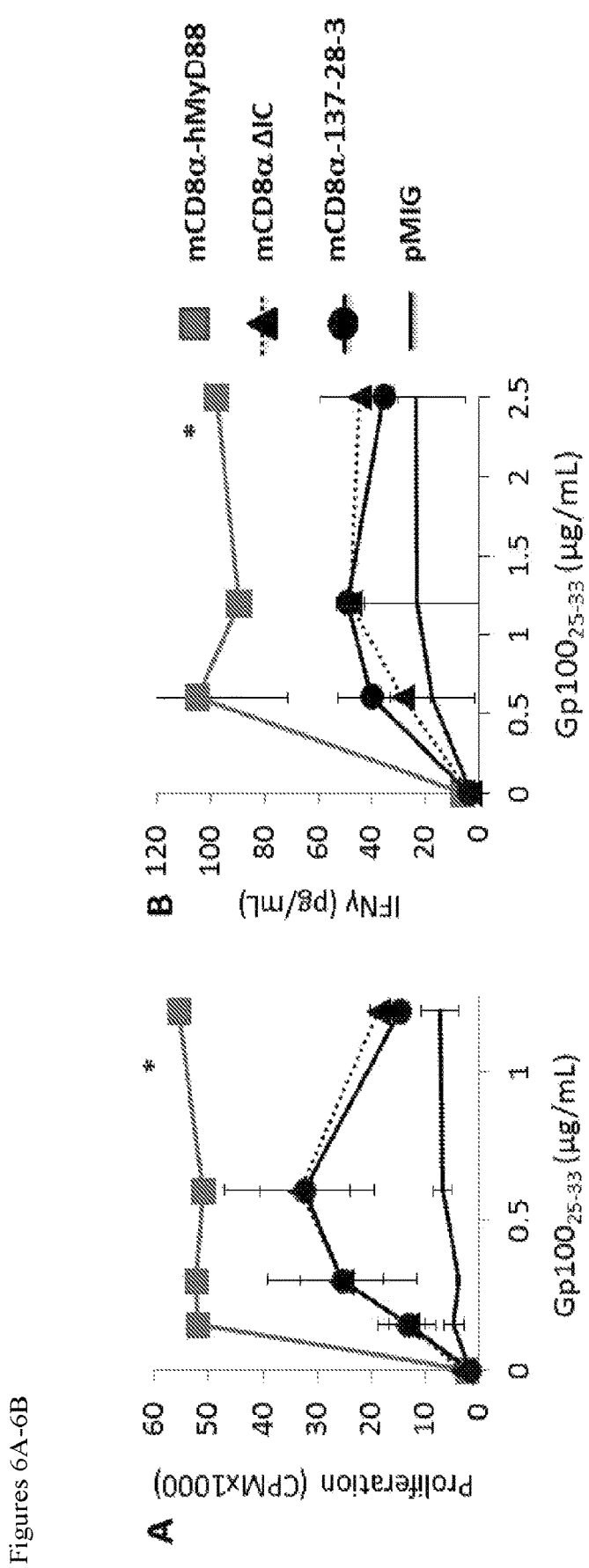
FIGS. 6A-6B. mCD8α-hMyD88 expression in mouse CD8 T cells augments T cell proliferation and IFN-γ production in response to stimulation with varying concentrations of tumor antigen. Proliferation was determined by $^3$H-thymidine incorporation and IFN-γ production by ELISA. The average (counts per minute) of triplicate wells (±SD) is shown after 48 hours of stimulation with peptide-pulsed splenocytes. *P<0.05 vs mCD8α-28-137-3; ANOVA.

The ability of each CD8α construct to alter TCR-mediated CD8+ T cell proliferation and cytokine production was examined. CD8+ T cells from TCR transgenic mice, specific for the gp100$_{25-33}$ antigen, were engineered to express mCD8α-hMyD88, mCD8αΔIC, mCD8α-28-137-3, or GFP control (pMIG). Forty-eight hours after transduction, T cells were stimulated with splenocytes pulsed with the varying concentrations of the gp100$_{25-33}$ peptide, representing a melanoma tumor antigen. T cells expressing mCD8α-hMyD88 exhibited greater proliferation (FIG. 6A) and IFN-gamma production (FIG. 6B), than did control cells at exceedingly lower concentrations of tumor antigen. Furthermore, it is important to note that at higher antigen concentrations (2.5 μg/ml), mCD8αΔIC—expressing T cells or mCD8α-28-137-3—expressing T cells exhibited reduced proliferation or a leveling off of IFN-gamma production while mCD8α-hMyD88 maintained a high proliferative capacity and IFN-gamma production. T cells engineered to express mCD8αΔIC, mCD8α-28-137-3, and GFP all demonstrated similar proliferation. The fact that mCD8α-MyD88 T cells did not proliferate or produce IFN-γ in the absence of antigen is very important as it indicates that the costimulatory effects of MyD88 occur in a TCR—and tumor antigen—specific manner.

Experiment 2D.

Figure 7:
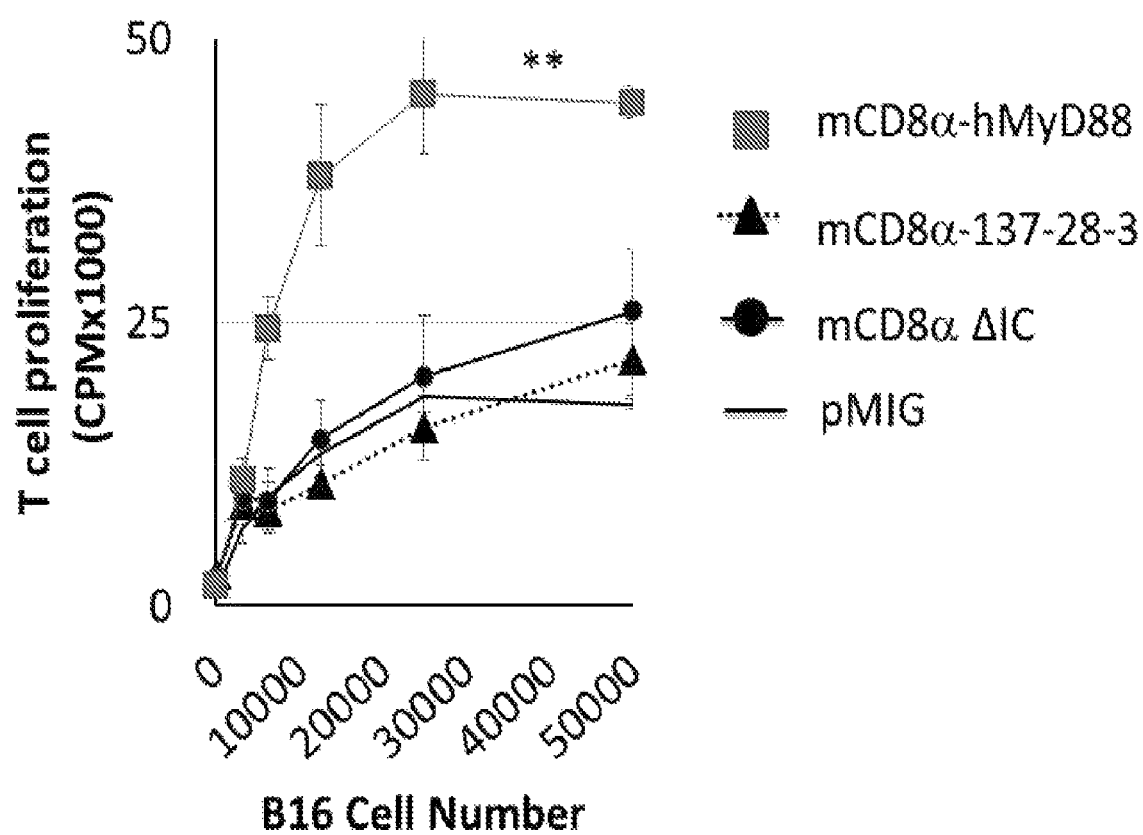
FIG. 7. mCD8α-hMyD88 expression in CD8+ T cells augments T cell proliferation in response to activation with titrating numbers of tumor cells. The average CPM (counts per minute) of triplicate wells (+SD) is shown after 72 hours of stimulation with the indicated number of B16 cells. **P<0.01 vs mCD8α-137-28-3; ANOVA.

To determine how the different CD8α constructs altered the capacity of CD8+ T cells to proliferate in response to stimulation with tumor cells, pmel T cells were engineered to express mCD8α-hMyD88, mCD8αΔIC, mCD8α-28-137-3 (mCD8α-137-28-3), or GFP control (pMIG) and co-cultured with varying numbers of mouse B16 melanoma cells. As shown in FIG. 7, mCD8α-hMyD88-transfected pmel T cells exhibited greater proliferation than did control cells when co-cultured with all but the lowest number of B16 cells. Proliferation occurred in a B16 cell number—dependent fashion indicating that the T cell response was in fact due the presence of tumor antigen. T cells engineered to express mCD8αΔIC, mCD8α-137-28-3 and GFP all demonstrated similar proliferative capacity.

Experiment 2E.

Figure 8:
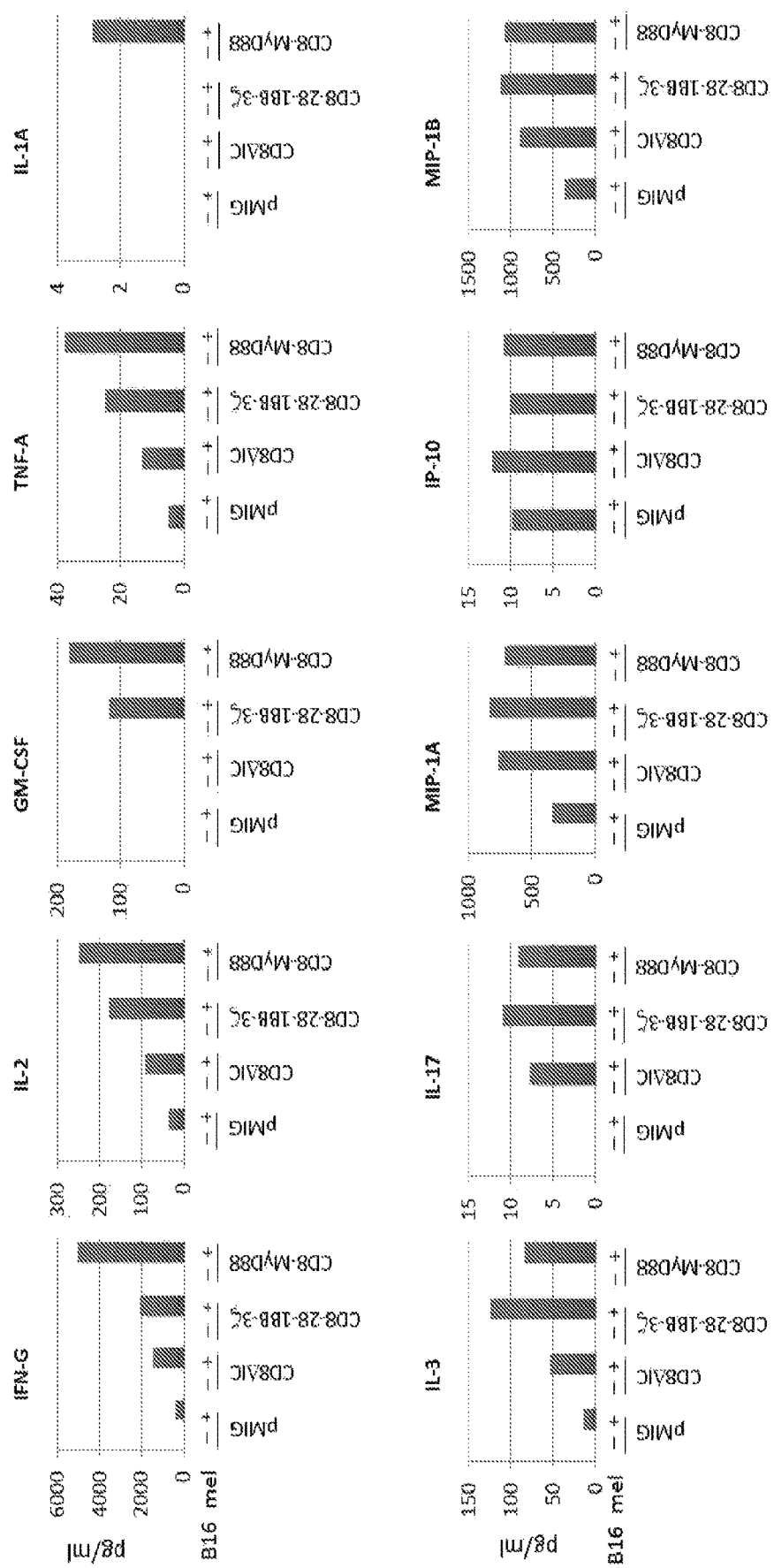
FIG. 8. MyD88 signaling in T cells alters cytokine secretion in response to tumor antigen on tumor cells. Transduced pmel T cells were co-cultured with irradiated B16-F1 tumor cells. Supernatant was collected at 24 and the levels of the various factors were evaluated using Milliplex Cytokine Array.
Figure 9:
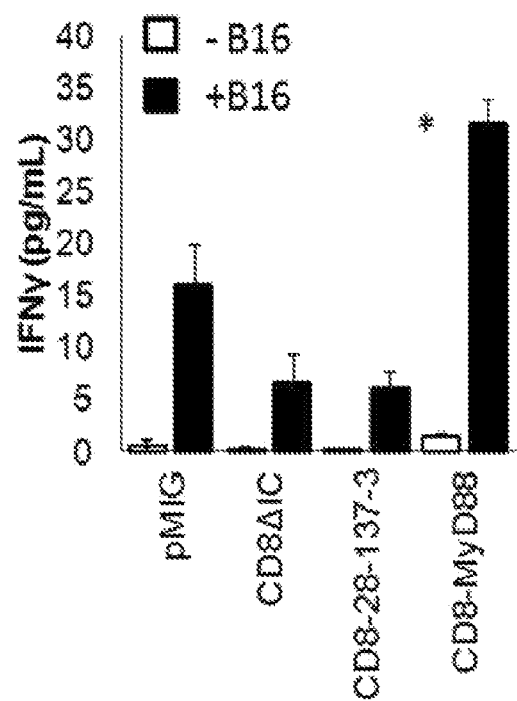
FIG. 9. MyD88 signaling in T cells increases cytokine secretion in response to tumor antigen on tumor cells. Transduced pmel T cells were co-cultured with irradiated B16-F1 tumor cells. Supernatant was collected at 24 hours and diluted 100-fold before conducting an ELISA. *P<0.05 vs mCD8α-28-137-3; ANOVA.

Mouse T cells were transduced with mCD8α-hMyD88, mCD8αΔIC, mCD8α-137-28-3 (CD8-28-1BB-3ξ), or GFP control (pMIG) as indicated in FIG. 8. T cells were co-cultured with B16 cells for 24 hours. The levels of the various factors shown in FIG. 8 were evaluated using a Milliplex Cytokine Array. mCD8α-hMyD88 T cells exhibited an increased production of IFNγ, IL-2, GM-CSF and TNFα as compared with T cells expressing the control vector (pMIG) and mCD8αΔIC (lacking intracellular signaling domains). Importantly, mCD8α-hMyD88 T cells demonstrated increased levels of these same cytokines over mCD8α-28-137-3. In contrast, mCD8α-28-137-3 showed increased levels of IL-3 as compared with mCD8α-hMyD88. These data highlight specific distinctions in the ability of MyD88 to activate T cells as compared with 28-137-3 signaling. mCD8α-hMyD88 was as effective at inducing the expression of IL-17, MIP-1A, IP-10 and MIP-1B as were mCD8αΔIC and mCD8α-28-137-3, suggesting that the elevated levels of other factors did not occur in a non-specific manner. Only mCD8α-hMyD88 induced IL-1α. It is worth noting that overexpressing CD8α also resulted in increased cytokine secretion relative to control T cells (transduced with pMIG). This highlights the potential to use CD8α overexpression as an alternate approach to further potentiate T cell responses; albeit in the absence of an activating intracellular signaling domain CD8α overexpression alone is considerably weaker than mCD8α-hMyD88. That mCD8α-hMyD88 T cells increased IFN-γ production was confirmed by ELISA in separate experiments, FIG. 9.

Experiment 2F.

Figure 10:
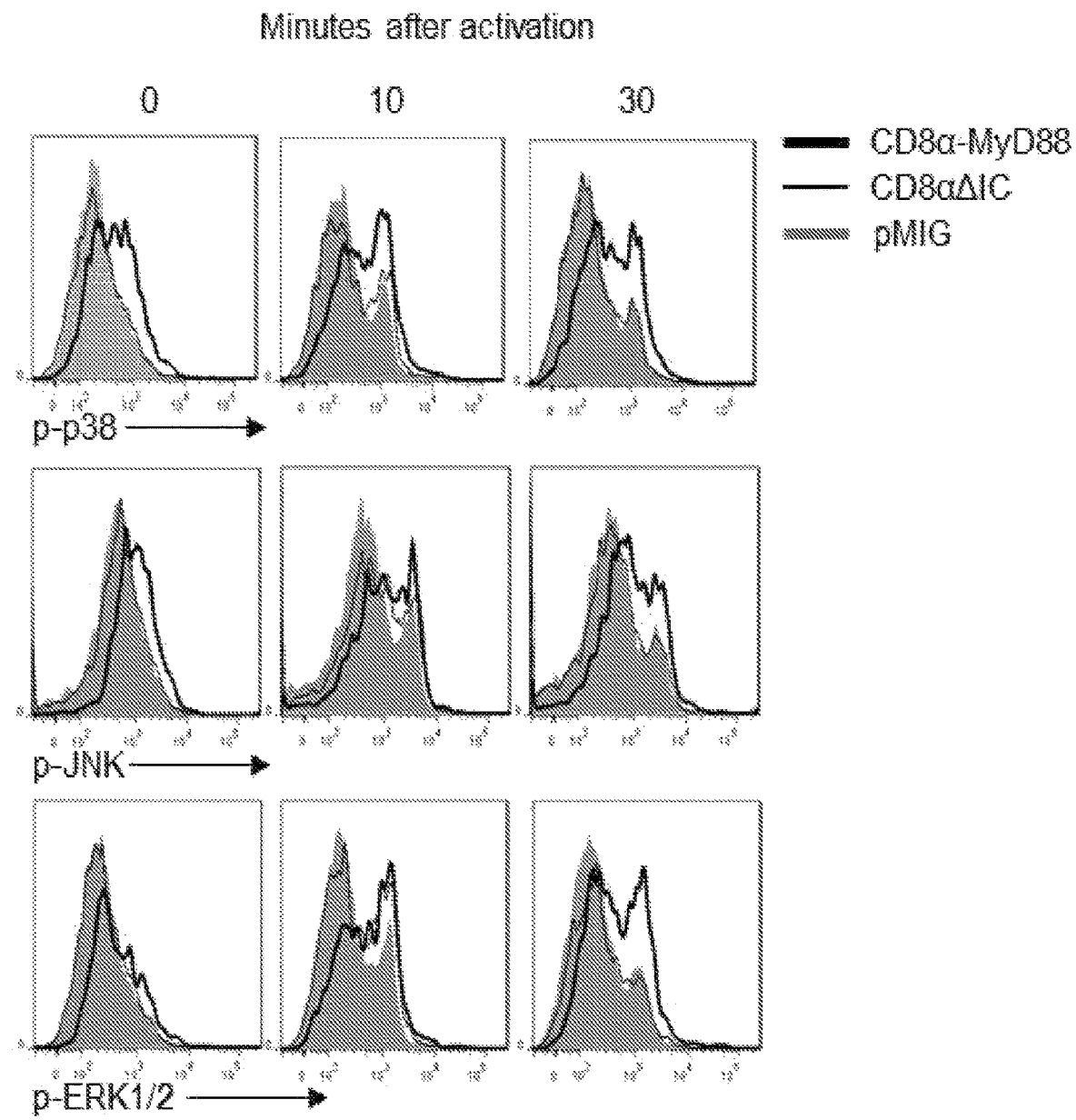
FIG. 10. CD8-MyD88 signaling. CD8+ pmel T cells were transduced with CD8α-MyD88, CD8αΔIC or pMIG control vector. T cells were stimulated in at a 1 to 1 ratio with B16 tumor cells for 10 and 30 minutes, then fixed in 4% PFA. The 0 time point indicates no B16 were added. Cells were permeabilizied and stained for the indicated phosphorylated proteins, p-p38, p-JNK, p-ERK1/2, which are activated in response to TCR signaling.

CD8-MyD88 signaling. CD8+ pmel T cells were transduced with CD8α-MyD88, CD8αΔIC or pMIG control vector. T cells were stimulated in at a 1 to 1 ratio with B16 tumor cells for 10 and 30 minutes, then fixed in 4% PFA. The 0 time point indicates no B16 were added. Cells were permeabilized and stained for the indicated phosphorylated proteins, p-p38, p-JNK, p-ERK½ which are activated in response to TCR signaling. As shown in FIG. 10, these results indicate that CD8α-MyD88 enhances signaling in part by increasing the expression levels of these proteins, sustaining the overall duration of signaling above control cells and by increasing the number of responding cells.

Experiment 2G.

Figure 11:
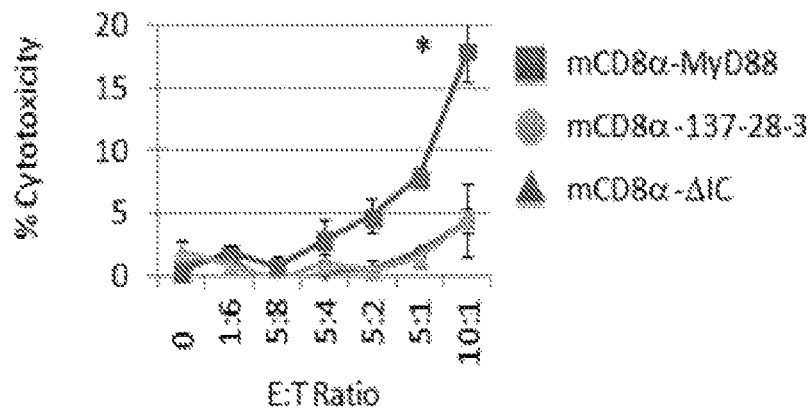
FIG. 11. mCD8α-hMyD88-transduced T cells exhibit enhanced cytotoxicity against B16 melanoma in vitro. Cytotoxicity was evaluated at the indicated effector (T cells) to target (B16 melanoma) ratios over the course of 4 hours. *P<0.05 vs mCD8α-28-137-3; ANOVA.

The ability of mCD8α-hMyD88 to augment T cell cytotoxicity was examined. mCD8α-hMyD88 expression significantly enhanced the killing of mouse melanoma cells as compared with T cells expressing mCD8αΔIC or mCD8α-28-137-3, FIG. 11.

Experiment 2H.

Figure 12:
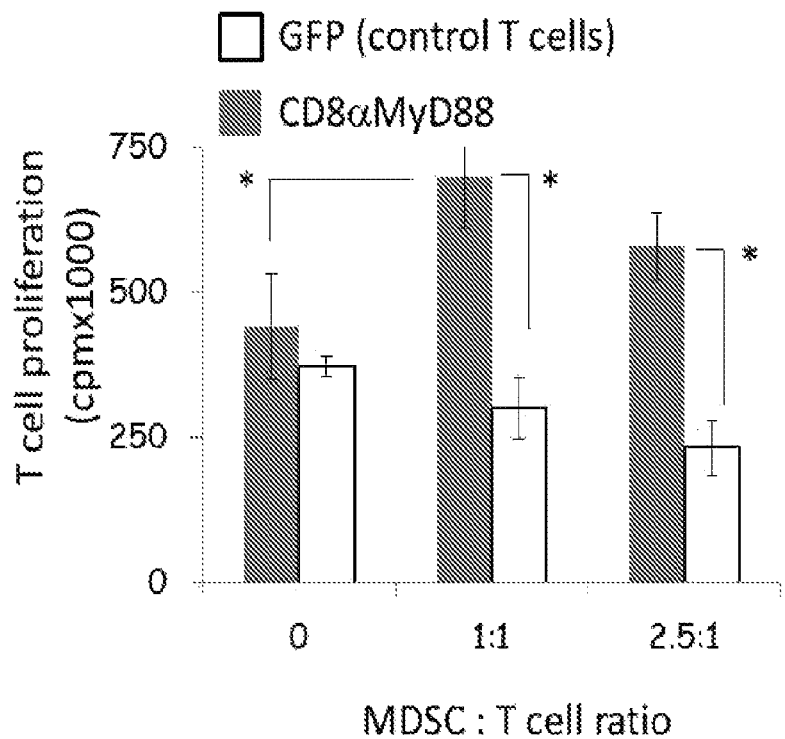
FIG. 12. CD8+ T cells expressing mCD8α-hMyD88 resist MDSC-mediated suppression and exhibit increased proliferation. CD8+ T cells engineered to express mCD8α-hMyD88 or control GFP were co-cultured with MDSCs at the indicated ratios. The average CPM (counts per minute) of triplicate wells (±SD) is shown after 72 hrs. *P<0.05; T-test.

It has been demonstrated that tumor reactive T cells engineered to secrete a ligand that activates toll-like receptor 5 (TLR5) enhanced the ability of T cells to destroy a melanoma tumor in mice (Geng et al., *Can Res.* 2015; 75:1959-1971). The increased antitumor activity was associated with a reduced number of myeloid derived suppressor cells (MDSC) in tumors and spleens. MDSCs derived from mice treated with TLR5 ligand-secreting T cells also demonstrated phenotypic changes including increased levels of major histocompatibility complex (MHC) I and MHC II as well as increased expression levels of the costimulatory molecule CD86 which could potentiate antitumor T cell activity. Furthermore, TLR engagement on T cells alters the cytokine and chemokine profile in vitro and in vivo and these changes were associated with reduced numbers of and phenotypic alterations in myeloid derived suppressor cells (MDSC). MDSCs are potent inhibitors of antitumor CD8 and CD4 T cell responses. TLR stimulation requires MyD88 signaling. Therefore, the ability of mCD8α-hMyD88 expression in CD8+ T cells to alter cellular responses to MDSC-mediated suppression was evaluated. As shown in FIG. 12, MDSCs suppressed the proliferation of GFP control T cells in an MDSC number-dependent fashion. At a ratio of 1 T cell to 2.5 MDSCs, T cells were suppressed nearly 40%. In sharp contrast, CD8+ T cells expressing CD8α-hMyD88 were not only resistant to MDSC-mediated suppression, such T cells demonstrated a significant increase in proliferation at the ratios of T cell to MDSC examined as compared with mCD8α-hMyD88 T cells in the absence of MDSCs. Therefore, in addition to augmenting responses to weak tumor antigens and antigens expressed at low density, mCD8α-hMyD88 expression offers the advantage of further potentiating T cell responses by overcoming MDSC-mediated suppression.

Experiment 2I.

Figure 13A:
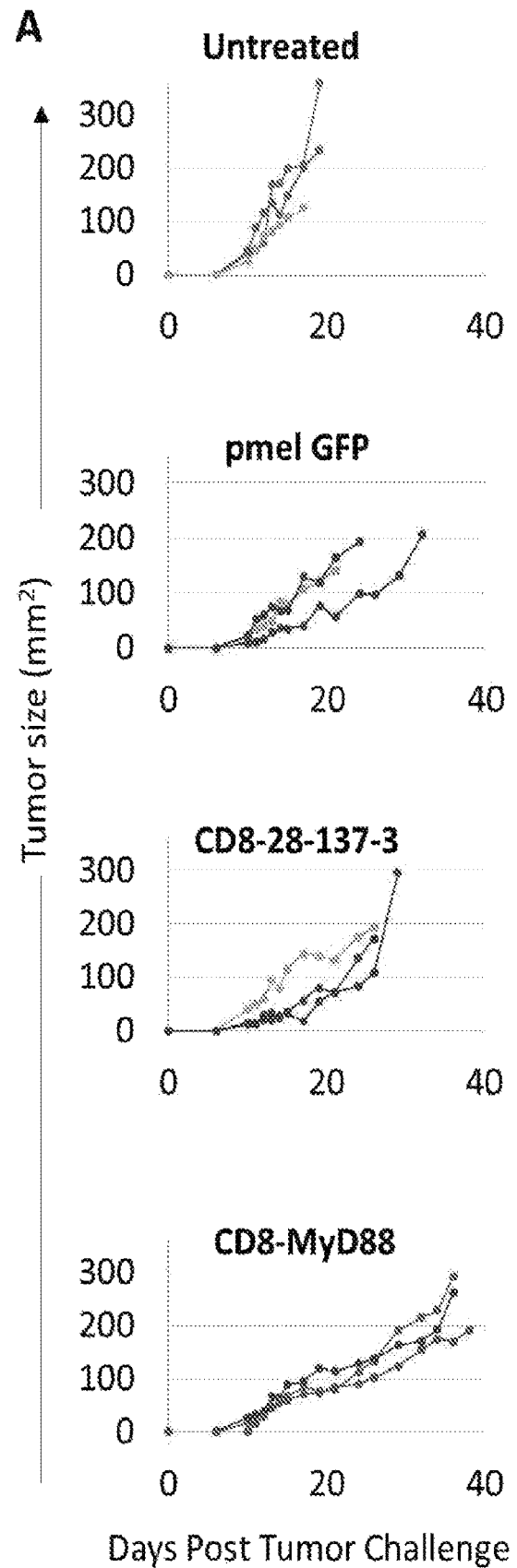
FIGS. 13A-13B. Tumor-bearing mice treated with mCD8α-hMyD88 T cells exhibit enhanced antitumor responses and prolonged survival.
Figure 13B:
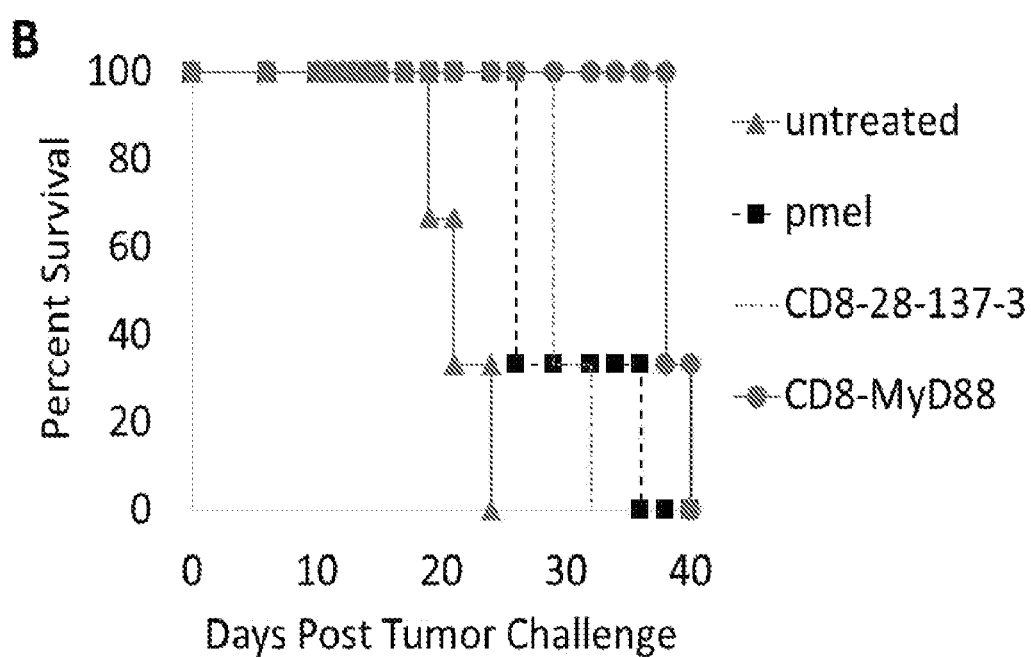

The antitumor activity of pmel CD8+ T cells engineered to express GFP (which serves as a transduction control), CD28-CD137-CD3zeta, or MyD88 was tested in mice with established B16 melanoma tumors. When tumors reached a size of approximately 30 mm$^2$, mice were intravenously injected with ~2.5×10$^6$ T cells and tumor growth was measured over the course of several weeks. Mice treated with mCD8α-hMyD88 T cells exhibited delayed tumor growth kinetics (FIG. 13A) and prolonged mouse survival (FIG. 13B) as compared with mice treated with control GFP or mCD8α-28-137-3 T cells. No significant differences were detected between mice treated with GFP and mCD8α-28-137-3 T cells.

Experiment 2J.

Figures 14A, 14B:
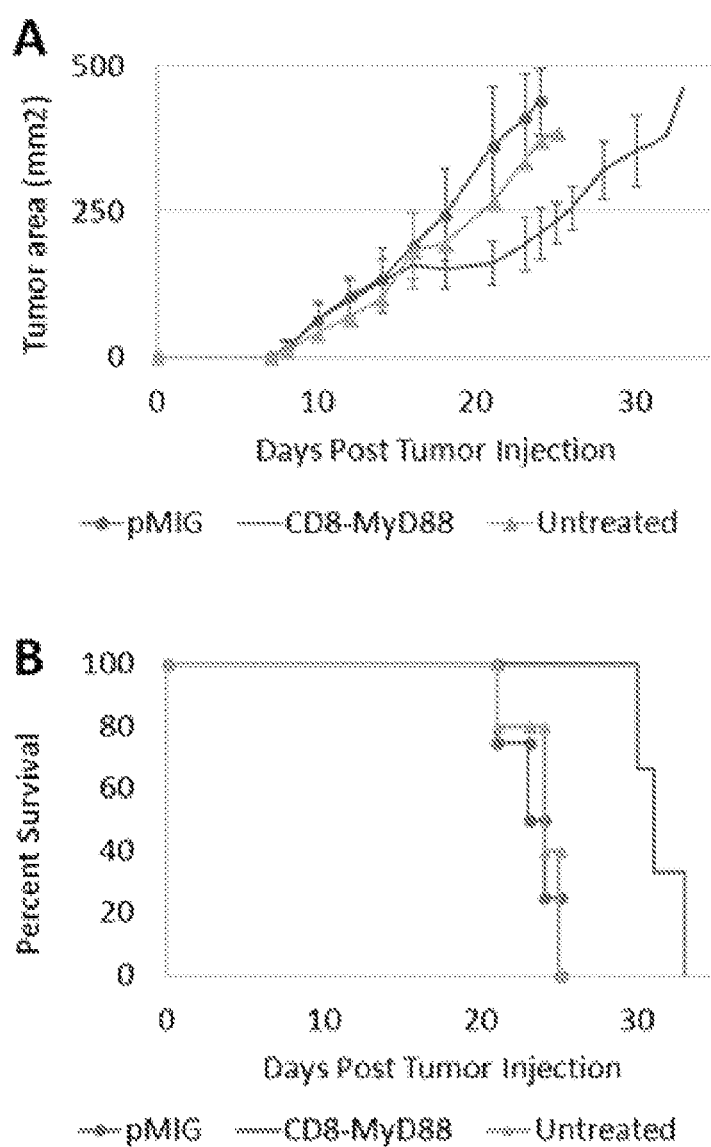
FIGS. 14A-14B. mCD8α-hMyD88 expression in tumor reactive T cells enhances antitumor responses and prolongs mouse survival in the absence of any support therapy. Mice treated with mCD8α-hMyD88 T cells exhibited significantly enhanced antitumor responses (FIG. 14A) beginning on day 23 (one-way ANOVA; p<0.01) and overall prolonged survival (FIG. 14B; Wilcoxon, p<0.05) as compared with mice untreated mice or mice treated with control pMIG pmel T cells.

A further in vivo experiment confirmed that mCD8α-hMyD88 expression in tumor reactive T cells enhances antitumor responses and prolongs mouse survival in the absence of any support therapy. C57BL6 mice were injected s.c. with B16 melanoma tumor cells in the rear flank. Eight days after tumor cell injection, mice received by tail i.v. injection ~10$^6$ pmel T cells engineered to express mCD8α-hMyD88 or control pMIG vector or mice remained untreated. No support therapy (i.e., IL-2, immune adjuvants or checkpoint blockade Ab) was provided. Mice treated with mCD8α-hMyD88 T cells exhibited significantly enhanced antitumor responses (FIG. 14A) beginning on day 23 (one-way ANOVA; p<0.01) and overall prolonged survival (FIG. 14B; Wilcoxon, p<0.05) as compared with mice untreated mice or mice treated with control pMIG pmel T cells. Untreated mice had a median survival of 24 d; pMIG T cell—treated mice: 23.5 d; mCD8α-hMyD88—treated mice: 31 d. The error bars represent the standard deviation from the mean of eight mice.

Experiment 2K.

Figure 15:
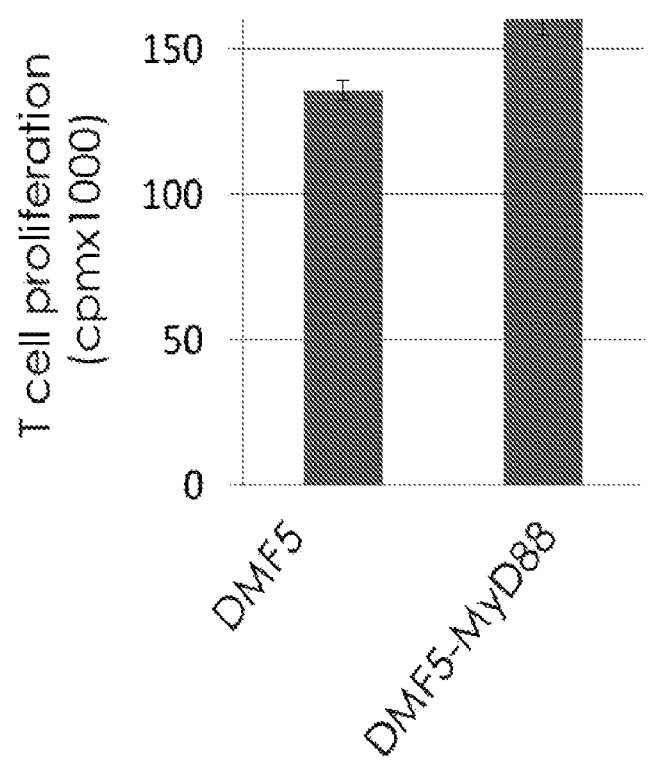
FIG. 15. T cells expressing MyD88-linked to a tumor-reactive TCR showed enhanced T cell proliferation.

The ability for MyD88 signaling to enhance TCR-induced proliferation when linked directly to the TCR was examined. DMF5, a TCR specific for the MART-1$_{26-35}$ peptide from the MART-1 melanoma antigen presented by MHC I, was fused to MyD88 lacking the TIR domain. The DMF5 TCR was kindly provided by Dr. Laura Johnson at the National Cancer Institute and is the same sequence used in clinical trials registered at www.ClinicalTrials.gov as NCI-07-C-0174 and NCI-07-C-0175 (Johnson, L A et al. *Blood* 2009; 114:535-546; Johnson, L A et al. *J. Immunol.* 2006; 177:6548-6559). Transduction efficiencies were similar between DMF5 and DMF5-MyD88. As shown in FIG. 15, linking MyD88 to TCR enhanced T cell proliferation, suggesting that recruiting MyD88 to the TCR signaling complex through different means including, but not restricted to, CD8α or TCR can enhance T cell responses.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety.

---

What is claimed is:

1. A fusion protein comprising an amino-terminal domain linked to a region of MyD88 lacking the TIR domain,
   wherein the amino-terminal domain is selected from the group consisting of:
   (a) extracellular and transmembrane regions of CD8α,
   (b) a transmembrane region of CD8α,
   (c) extracellular and transmembrane regions of CD4, and
   (d) a T cell receptor; and
   wherein the region of MyD88 lacking the TIR domain corresponds to amino acids 1-155 of human MyD88 (SEQ ID NO:24) plus or minus up to 10 amino acids from either end or from both ends.

2. The fusion protein of claim 1, wherein (a) the extracellular and transmembrane regions of CD8α correspond to amino acids 1-217 of mouse CD8α (SEQ ID NO:16) or amino acids 1-203 of human CD8α (SEQ ID NO:12) and (b) the region of MyD88 lacking the TIR domain corresponds to amino acids 1-155 of human MyD88 (SEQ ID NO:24).

3. The fusion protein of claim 1, wherein the fusion protein comprises mCD8α-hMyD88 as set forth in SEQ ID NO:17 or hCD8α-hMyD88 as set forth in SEQ ID NO:14.

4. The fusion protein of claim 1, wherein the transmembrane region of CD8α corresponds to amino acids 1-83 of SEQ ID NO:18 and the region of MyD88 lacking the TIR domain corresponds to amino acids 1-155 of human MyD88 (SEQ ID NO:24).

5. The fusion protein of claim 1, wherein the fusion protein comprises hCD8αTM-hMyD88 as set forth in SEQ ID NO:18.

6. The fusion protein of claim 1, wherein (a) the extracellular and transmembrane regions of CD4 correspond to amino acids 1-417 of mouse CD4 (amino acids 1-417 of SEQ ID NO:21) or human CD4 (amino acids 1-418 of SEQ ID NO:20) and (b) the region of MyD88 lacking the TIR domain corresponds to amino acids 1-155 of human MyD88 (SEQ ID NO:24).

7. The fusion protein of claim 1, wherein the fusion protein comprises mCD4-hMyD88 as set forth in SEQ ID NO:21 or hCD4-hMyD88 as set forth in SEQ ID NO:20.

8. The fusion protein of claim 1, wherein the TCR is the DMFS TCR having the amino acid sequence of residues 1-603 of SEQ ID NO:22 and the region of MyD88 lacking the TIR domain corresponds to amino acids 1-155 of human MyD88 (SEQ ID NO:24).

9. The fusion protein of claim 1, wherein the fusion protein comprises hTCR-hMyD88 as set forth in SEQ ID NO:22.

10. An isolated population of cells expressing at least one fusion protein of claim 1.

11. The isolated population of cells of claim 10, wherein the isolated population of cells expresses at least one fusion protein selected from the group consisting of mCD8α-hMyD88 (SEQ ID NO:17), hCD8α-hMyD88 (SEQ ID NO:14), hCD8αTM-hMyD88 (SEQ ID NO:18), mCD4-hMyD88 (SEQ ID NO:21), hCD4-hMyD88 (SEQ ID NO:20) and hTCR-hMyD88 (SEQ ID NO:22).

12. A method of treating a subject having cancer or an infectious disease, comprising administering to a subject having cancer or an infectious disease a therapeutically-effective amount of at least one population of cells as defined in claim 10.

13. A method of treating a subject having cancer or an infectious disease, comprising administering to a subject having cancer or an infectious disease a therapeutically-effective amount of at least one population of cells as defined in claim 11.

14. A method of conferring T cell resistance against myeloid derived suppressor cells (MDSC)-mediated suppression, comprising expressing at least one fusion protein of claim 1 in a T cell.

15. The method of claim 14, wherein the fusion protein is selected from the group consisting of mCD8α-hMyD88 (SEQ ID NO:17), hCD8α-hMyD88 (SEQ ID NO:14), hCD8αTM-hMyD88 (SEQ ID NO:18), mCD4-hMyD88 (SEQ ID NO:21), hCD4-hMyD88 (SEQ ID NO:20) and hTCR-hMyD88 (SEQ ID NO:22).

16. A method of enhancing immune cell recognition of an antigen, comprising expressing at least one fusion protein of claim 1 in an immune cell.

17. The method of claim 16, wherein the fusion protein is selected from the group consisting of mCD8α-hMyD88 (SEQ ID NO:17), hCD8α-hMyD88 (SEQ ID NO:14), hCD8αTM-hMyD88 (SEQ ID NO:18), mCD4-hMyD88 (SEQ ID NO:21), hCD4-hMyD88 (SEQ ID NO:20) and hTCR-hMyD88 (SEQ ID NO:22).

18. The method of claim 16, wherein the antigen is present at a low concentration in vitro or in vivo.

19. The method of claim 16, wherein the antigen is a weakly antigenic antigen.

* * * * *

SEQUENCE LISTING

<160> NUMBER OF SEQ ID NOS: 24

<210> SEQ ID NO 1
<211> LENGTH: 705
<212> TYPE: DNA
<213> ORGANISM: Homo sapiens

<400> SEQUENCE: 1

```
atggccttac cagtgaccgc cttgctcctg ccgctggcct tgctgctcca cgccgccagg      60
ccgagccagt tccgggtgtc gccgctggat cggacctgga acctgggcga cagtggag       120 ctgaagtgcc aggtgctgct gtccaacccg acgtcgggct gctcgtggct cttccagccg     180
cgcggcgccg ccgccagtcc caccttcctc ctatacctct cccaaaacaa gcccaaggcg     240
gccgaggggc tggacaccca gcggttctcg ggcaagaggt tgggggacac cttcgtcctc     300
accctgagcg acttccgccg agagaacgag ggctactatt tctgctcggc cctgagcaac     360
tccatcatgt acttcagcca cttcgtgccg gtcttcctgc agcgaagcc caccacgacg     420 ccagcgccgc gaccaccaac accggcgccc accatcgcgt cgcagcccct gtccctcgc      480 ccagaggcgt gccggccagc ggcgggggc gcagtgcaca cgaggggct ggacttcgcc       540 tgtgatatct acatctgggc gcccttggcc gggacttgtg gggtccttct cctgtcactg     600
gttatcaccc tttactgcaa ccacaggaac cgaagacgtg tttgcaaatg tcccggcct      660
```

```
gtggtcaaat cgggagacaa gcccagcctt tcggcgagat acgtc            705
```

<210> SEQ ID NO 2
<211> LENGTH: 609
<212> TYPE: DNA
<213> ORGANISM: Artificial Sequence
<220> FEATURE:
<223> OTHER INFORMATION: Human CD8a without intracellular signaling
      domain

<400> SEQUENCE: 2

```
atggcctta c cagtgaccgc cttgctcctg ccgctggcct tgctgctcca cgccgccagg   60
ccgagccagt tccgggtgtc gccgctggat cggacctgga acctgggcga cagtggag   120
ctgaagtgcc aggtgctgct gtccaacccg acgtcgggct gctcgtggct cttccagccg   180
cgcggcgccg ccgccagtcc caccttcctc ctatacctct cccaaaacaa gcccaaggcg   240
gccgaggggc tggacaccca gcggttctcg gcaagaggt tggggacac cttcgtcctc   300
accctgagcg acttccgccg agagaacgag ggctactatt tctgctcggc cctgagcaac   360
tccatcatgt acttcagcca cttcgtgccg gtcttcctgc agcgaagcc caccacgacg   420
ccagcgccgc gaccaccaac accggcgccc accatcgcgt cgcagcccct gtccctgcgc   480
ccagaggcgt gccggccagc ggcgggggc gcagtgcaca cgagggggct ggacttcgcc   540
tgtgatatct acatctgggc gcccttggcc gggacttgtg gggtccttct cctgtcactg   600
gttatcacc                                                          609
```

<210> SEQ ID NO 3
<211> LENGTH: 1074
<212> TYPE: DNA
<213> ORGANISM: Artificial Sequence
<220> FEATURE:
<223> OTHER INFORMATION: Human CD8a-MyD88 where MyD88 lacks the TIR
      domain

<400> SEQUENCE: 3

```
atggcctta c cagtgaccgc cttgctcctg ccgctggcct tgctgctcca cgccgccagg   60
ccgagccagt tccgggtgtc gccgctggat cggacctgga acctgggcga cagtggag   120
ctgaagtgcc aggtgctgct gtccaacccg acgtcgggct gctcgtggct cttccagccg   180
cgcggcgccg ccgccagtcc caccttcctc ctatacctct cccaaaacaa gcccaaggcg   240
gccgaggggc tggacaccca gcggttctcg gcaagaggt tggggacac cttcgtcctc   300
accctgagcg acttccgccg agagaacgag ggctactatt tctgctcggc cctgagcaac   360
tccatcatgt acttcagcca cttcgtgccg gtcttcctgc agcgaagcc caccacgacg   420
ccagcgccgc gaccaccaac accggcgccc accatcgcgt cgcagcccct gtccctgcgc   480
ccagaggcgt gccggccagc ggcgggggc gcagtgcaca cgagggggct ggacttcgcc   540
tgtgatatct acatctgggc gcccttggcc gggacttgtg gggtccttct cctgtcactg   600
gttatcacca tggctgcagg aggtcccggc gcggggtctg cggccccggt ctcctccaca   660
tcctcccttc ccctggctgc tctcaacatg cgagtgcggc gccgcctgtc tctgttcttg   720
aacgtgcgga cacaggtggc ggccgactgg accgcgctgg cggaggagat ggactttgag   780
tacttggaga tccggcaact ggagacacaa gcggacccca ctggcaggct gctggacgcc   840
tggcagggac gccctggcgc ctctgtaggc cgactgctcg agctgcttac caagctgggc   900
cgcgacgacg tgctgctgga gctgggaccc agcattgagg aggattgcca aaagtatatc   960
```
ttgaagcagc agcaggagga ggctgagaag cctttacagg tggccgctgt agacagcagt 1020
gtcccacgga cagcagagct ggcgggcatc accacacttg atgaccccct gggg 1074

<210> SEQ ID NO 4
<211> LENGTH: 744
<212> TYPE: DNA
<213> ORGANISM: Mus musculus

<400> SEQUENCE: 4
atggcctcac cgttgacccg ctttctgtcg ctgaacctgc tgctgctggg tgagtcgatt 60
atcctgggga gtggagaagc taagccacag gcacccgaac tccgaatctt tccaaagaaa 120
atggacgccg aacttggtca gaaggtggac ctggtatgtg aagtgttggg gtccgtttcg 180
caaggatgct cttggctctt ccagaactcc agctccaaac tcccccagcc caccttcgtt 240
gtctatatgg cttcatccca caacaagata acgtgggacg agaagctgaa ttcgtcgaaa 300 ctgtttctg ccatgaggga cacgaataat aagtacgttc tcaccctgaa caagttcagc 360
aaggaaaacg aaggctacta tttctgctca gtcatcagca actcggtgat gtacttcagt 420
tctgtcgtgc cagtccttca gaaagtgaac tctactacta ccaagccagt gctgcgaact 480
ccctcacctg tgcaccctac cgggacatct cagcccaga gaccagaaga ttgtcggccc 540
cgtggctcag tgaaggggac cggattggac ttcgcctgtg atatttacat ctgggcaccc 600
ttggccggaa tctgcgtggc ccttctgctg tccttgatca tcactctcat ctgctaccac 660
aggagccgaa agcgtgtttg caaatgtccc aggccgctag tcagacagga aggcaagccc 720
agaccttcag agaaaattgt gtaa 744

<210> SEQ ID NO 5
<211> LENGTH: 651
<212> TYPE: DNA
<213> ORGANISM: Artificial Sequence
<220> FEATURE:
<223> OTHER INFORMATION: Mouse CD8a without the intracellular signaling
      domain

<400> SEQUENCE: 5
atggcctcac cgttgacccg ctttctgtcg ctgaacctgc tgctgctggg tgagtcgatt 60
atcctgggga gtggagaagc taagccacag gcacccgaac tccgaatctt tccaaagaaa 120
atggacgccg aacttggtca gaaggtggac ctggtatgtg aagtgttggg gtccgtttcg 180
caaggatgct cttggctctt ccagaactcc agctccaaac tcccccagcc caccttcgtt 240
gtctatatgg cttcatccca caacaagata acgtgggacg agaagctgaa ttcgtcgaaa 300 ctgtttctg ccatgaggga cacgaataat aagtacgttc tcaccctgaa caagttcagc 360
aaggaaaacg aaggctacta tttctgctca gtcatcagca actcggtgat gtacttcagt 420
tctgtcgtgc cagtccttca gaaagtgaac tctactacta ccaagccagt gctgcgaact 480
ccctcacctg tgcaccctac cgggacatct cagcccaga gaccagaaga ttgtcggccc 540
cgtggctcag tgaaggggac cggattggac ttcgcctgtg atatttacat ctgggcaccc 600
ttggccggaa tctgcgtggc ccttctgctg tccttgatca tcactctcat c 651

<210> SEQ ID NO 6
<211> LENGTH: 1116
<212> TYPE: DNA
<213> ORGANISM: Artificial Sequence
<220> FEATURE:
<223> OTHER INFORMATION: Mouse CD8a-human MyD88 where MyD88 lacks TIR
      domain

<400> SEQUENCE: 6

```
atggcctcac cgttgacccg ctttctgtcg ctgaacctgc tgctgctggg tgagtcgatt      60
atcctgggga gtggagaagc taagccacag gcacccgaac tccgaatctt tccaaagaaa     120
atggacgccg aacttggtca gaaggtggac ctggtatgtg aagtgttggg gtccgtttcg     180
caaggatgct cttggctctt ccagaactcc agctccaaac tcccccagcc caccttcgtt     240
gtctatatgg cttcatccca caacaagata acgtgggacg agaagctgaa ttcgtcgaaa     300
ctgttttctg ccatgaggga cacgaataat aagtacgttc tcaccctgaa caagttcagc     360
aaggaaaacg aaggctacta tttctgctca gtcatcagca actcggtgat gtacttcagt     420
tctgtcgtgc cagtccttca gaaagtgaac tctactacta ccaagccagt gctgcgaact     480
ccctcacctg tgcaccctac cggacatct cagccccaga gaccagaaga ttgtcggccc     540
cgtggctcag tgaaggggac cggattggac ttcgcctgtg atatttacat ctgggcaccc     600
ttggccggaa tctgcgtggc ccttctgctg tccttgatca tcactctcat catggctgca     660
ggaggtcccg cgcggggtc tgcggccccg gtctcctcca catcctccct tcccctggct     720
gctctcaaca tgcgagtgcg cgccgcctg tctctgttct gaacgtgcgg acacaggtg      780
gcggccgact ggaccgcgct ggcggaggag atggactttg agtacttgga gatccggcaa     840
ctggagacac aagcggaccc cactggcagg ctgctggacg cctggcaggg acgccctggc     900
gcctctgtag gccgactgct cgagctgctt accaagctgg gccgcgacga cgtgctgctg     960
gagctgggac ccagcattga ggaggattgc caaaagtata tcttgaagca gcagcaggag    1020
gaggctgaga agcctttaca ggtggccgct gtagacagca gtgtcccacg gacagcagag    1080
ctggcgggca tcaccacact tgatgacccc ctgggg                              1116
```

<210> SEQ ID NO 7
<211> LENGTH: 715
<212> TYPE: DNA
<213> ORGANISM: Artificial Sequence
<220> FEATURE:
<223> OTHER INFORMATION: Human CD8a TM-MyD88

<400> SEQUENCE: 7

```
attcgtgccg gtcttcctgc cagcgaagcc caccacgacg ccagcgccgc gaccaccaac      60
accggcgccc accatcgcgt cgcagcccct gtccctgcgc ccagaggcgt gccggccagc     120
ggcgggggc gcagtgcaca cgaggggct ggacttcgcc tgtgatatct acatctgggc      180
gcccttggcc gggacttgtg gggtccttct cctgtcactg gttatcaccc tttactgcaa     240
ccacaggaac atggctgcag gaggtcccgg cgcggggtct gcggccccgg tctcctccac     300
atcctccctt cccctggctg ctctcaacat gcgagtgcgg cgccgcctgt ctctgttctt     360
gaacgtgcgg acacaggtgg cggccgactg gaccgcgctg cggaggaga tggactttga     420
gtacttggag atccggcaac tggagacaca agcggacccc actggcaggc tgctggacgc     480
ctggcaggga cgccctggcg cctctgtagg ccgactgctc gagctgctta ccaagctggg     540
ccgcgacgac gtgctgctgg agctgggacc cagcattgag gaggattgcc aaaagtatat     600
cttgaagcag cagcaggagg aggctgagaa gcctttacag gtggccgctg tagacagcag     660
tgtcccacgg acagcagagc tggcgggcat caccacactt gatgacccc tgggg           715
```

<210> SEQ ID NO 8
<211> LENGTH: 1254
<212> TYPE: DNA

<213> ORGANISM: Artificial Sequence
<220> FEATURE:
<223> OTHER INFORMATION: Mouse CD8a-human CD28-human 41BB-human CD3zeta

<400> SEQUENCE: 8

```
atggcctcac cgttgacccg ctttctgtcg ctgaacctgc tgctgctggg tgagtcgatt       60
atcctgggga gtggagaagc taagccacag gcacccgaac tccgaatctt ccaaagaaa      120
atggacgccg aacttggtca gaaggtggac ctggtatgtg aagtgttggg gtccgtttcg      180
caaggatgct cttggctctt ccagaactcc agctccaaac tcccccagcc caccttcgtt      240
gtctatatgg cttcatccca caacaagata acgtgggacg agaagctgaa ttcgtcgaaa      300
ctgttttctg ccatgaggga cacgaataat aagtacgttc tcaccctgaa caagttcagc      360
aaggaaaacg aaggctacta tttctgctca gtcatcagca actcggtgat gtacttcagt      420
tctgtcgtgc cagtccttca gaaagtgaac tctactacta ccaagccagt gctgcgaact      480
ccctcacctg tgcaccctac cgggacatct cagccccaga gaccagaaga ttgtcggccc      540
cgtggctcag tgaaggggac cggattgac ttcgcctgtg atatttacat ctgggcaccc      600
ttggccggaa tctgcgtggc ccttctgctg tccttgatca tcactctcat caggagtaag      660
aggagcaggc tcctgcacag tgactacatg aacatgactc ccgccgccc cgggcccacc      720
cgcaagcatt accagcccta tgccccacca cgcgacttcg cagcctatcg ctcccgtttc      780
tctgttgtta acggggcag aaagaagctc ctgtatatat tcaaacaacc atttatgaga      840
ccagtacaaa ctactcaaga ggaagatggc tgtagctgcc gatttccaga agaagaagaa      900
ggaggatgtg aactgagagt gaagttcagc aggagcgcag acgcccccgc gtaccagcag      960
ggccagaacc agctctataa cgagctcaat ctaggacgaa gagaggagta cgatgttttg     1020
gacaagagac gtggccggga ccctgagatg ggggaaagc cgagaaggaa gaaccctcag     1080
gaaggcctgt acaatgaact gcagaaagat aagatggcgg aggcctacag tgagattggg     1140
atgaaaggcg agcgccggag gggcaagggg cacgatggcc tttaccaggg tctcagtaca     1200
gccaccaagg acacctacga cgcccttcac atgcaggccc tgccccctcg ctaa          1254
```

<210> SEQ ID NO 9
<211> LENGTH: 1722
<212> TYPE: DNA
<213> ORGANISM: Artificial Sequence
<220> FEATURE:
<223> OTHER INFORMATION: Human CD4-MyD88 where MyD88 lacks the TIR domain

<400> SEQUENCE: 9

```
atgaaccggg gagtcccttt taggcacttg cttctggtgc tgcaactggc gctcctccca       60
gcagccactc agggaaagaa agtggtgctg ggcaaaaaag gggatacagt ggaactgacc      120
tgtacagctt cccagaagaa gagcatacaa ttccactgga aaaactccaa ccagataaag      180
attctgggaa atcaggctc cttcttaact aaaggtccat ccaagctgaa tgatcgcgct      240
gactcaagaa gaagcctttg gaccaagga actttcccc tgatcatcaa gaatcttaag      300
atagaagact cagatactta catctgtgaa gtggaggacc agaaggagga ggtgcaattg      360
ctagtgttcg gattgactgc caactctgac acccacctgc ttcaggggca gagcctgacc      420
ctgaccttgg agagccccc tggtagtagc cctcagtgc aatgtaggag tccaagggt      480
aaaaacatac aggggggaa gaccctctcc gtgtctcagc tggagctcca ggatagtggc      540
acctggacat gcactgtctt gcagaaccag aagaaggtgg agttcaaaat agacatcgtg      600
```

```
gtgctagctt tccagaaggc ctccagcata gtctataaga aagaggggga acaggtggag      660
ttctccttcc cactcgcctt tacagttgaa aagctgacgg gcagtggcga gctgtggtgg      720
caggcggaga gggcttcctc ctccaagtct tggatcacct ttgacctgaa gaacaaggaa      780
gtgtctgtaa acgggttac ccaggaccct aagctccaga tgggcaagaa gctcccgctc       840
cacctcaccc tgcccaggc cttgcctcag tatgctggct ctggaaacct caccctggcc       900
cttgaagcga aaacaggaaa gttgcatcag gaagtgaacc tggtggtgat gagagccact      960
cagctccaga aaatttgac ctgtgaggtg tggggaccca cctcccctaa gctgatgctg       1020
agtttgaaac tggagaacaa ggaggcaaag gtctcgaagc gggagaaggc ggtgtgggtg      1080
ctgaaccctg aggcggggat gtggcagtgt ctgctgagtg actcgggaca ggtcctgctg      1140
gaatccaaca tcaaggttct gcccacatgg tccaccccgg tgcagccaat ggccctgatt      1200
gtgctggggg gcgtcgccgg cctcctgctt ttcattgggc taggcatctt cttcatggct      1260
gcaggaggtc ccggcgcggg gtctgcggcc ccggtctcct ccacatcctc ccttcccctg      1320
gctgctctca acatgcgagt gcggcgccgc ctgtctctgt tcttgaacgt gcggacacag      1380
gtggcggccg actggaccgc gctggcggag gagatggact ttgagtactt ggagatccgg      1440
caactggaga cacaagcgga ccccactggc aggctgctgg acgcctggca gggacgccct      1500
ggcgcctctg taggccgact gctcgagctg cttaccaagc tgggccgcga cgacgtgctg      1560
ctggagctgg gacccagcat tgaggaggat tgccaaaagt atatcttgaa gcagcagcag      1620
gaggaggctg agaagccttt acaggtggcc gctgtagaca gcagtgtccc acggacagca      1680
gagctggcgg gcatcaccac acttgatgac cccctgggt ga                          1722

<210> SEQ ID NO 10
<211> LENGTH: 1719
<212> TYPE: DNA
<213> ORGANISM: Artificial Sequence
<220> FEATURE:
<223> OTHER INFORMATION: Mouse CD4-human MyD88 where MyD88 lacks the TIR
      domain

<400> SEQUENCE: 10
atgtgccgag ccatctctct taggcgcttg ctgctgctgc tgctgcagct gtcacaactc      60
ctagctgtca ctcaagggaa gacgctggtg ctggggaagg aagggaatc agcagaactg       120 ccctgcgaga gttcccagaa gaagatcaca gtcttcacct ggaagttctc tgaccagagg     180
aagattctgg ggcagcatgg caaaggtgta ttaattagag gaggttcgcc ttcgcagttt      240
gatcgttttg attccaaaaa aggggcatgg gagaaaggat cgtttcctct catcatcaat     300
aaacttaaga tggaagactc tcagacttat atctgtgagc tggagaacag gaaagaggag     360
gtggagttgt gggtgttcaa agtgaccttc agtccgggta ccagcctgtt gcaagggcag     420
agcctgaccc tgaccttgga tagcaactct aaggtctcta ccccttgac agagtgcaaa      480 cacaaaaagg gtaaagttgt cagtggttcc aaagttctct ccatgtccaa cctaaggggtt    540 caggacagcg acttctggaa ctgcaccgtg acccctggacc agaaaagaa ctggttcggc     600 atgacactct cagtgctggg ttttcagagc acagctatca cggcctataa gagtgaggga    660
gagtcagcga agttctcctt cccactcaac tttgcagagg aaaacgggtg gggagagctg     720
atgtggaagg cagagaagga ttcttcttc cagccctgga tctccttctc cataaagaac      780
aaagaggtgt ccgtacaaaa gtccaccaaa gacctcaagc tccagctgaa ggaaacgctc     840
ccactcaccc tcaagatacc ccaggtctcg cttcagtttg ctggttctgg caacctgact   900
```

| | |
|---|---|
| ctgactctgg acaaagggac actgcatcag gaagtgaacc tggtggtgat gaaagtggct | 960 |
| cagctcaaca atactttgac ctgtgaggtg atgggaccta cctctcccaa gatgagactg | 1020 |
| accctgaagc aggagaacca ggaggccagg gtctctgagg agcagaaagt agttcaagtg | 1080 |
| gtggcccctg agacagggct gtggcagtgt ctactgagtg aaggtgataa ggtcaagatg | 1140 |
| gactccagga tccaggtttt atccagaggg gtgaaccaga cagtgttcct ggcttgcgtg | 1200 |
| ctgggtggct ccttcggctt tctgggtttc cttgggctct gcatcctctg catggctgca | 1260 |
| ggaggtcccg cgcggggtc tgcggccccg gtctcctcca catcctccct tcccctggct | 1320 |
| gctctcaaca tgcgagtgcg cgccgcctg tctctgttct tgaacgtgcg gacacaggtg | 1380 |
| gcggccgact ggaccgcgct ggcggaggag atggactttg agtacttgga gatccggcaa | 1440 |
| ctggagacac aagcggaccc cactggcagg ctgctggacg cctggcaggg acgcctggc | 1500 |
| gcctctgtag gccgactgct cgagctgctt accaagctgg gccgcgacga cgtgctgctg | 1560 |
| gagctgggac ccagcattga ggaggattgc caaaagtata tcttgaagca gcagcaggag | 1620 |
| gaggctgaga agcctttaca ggtggccgct gtagacagca gtgtcccacg gacagcagag | 1680 |
| ctggcgggca tcaccacact tgatgacccc ctggggtga | 1719 |

<210> SEQ ID NO 11
<211> LENGTH: 2285
<212> TYPE: DNA
<213> ORGANISM: Artificial Sequence
<220> FEATURE:
<223> OTHER INFORMATION: Human DMF5 TCR-MyD88 where MyD88 lacks the TIR
      domain

<400> SEQUENCE: 11

| | |
|---|---|
| ccgccatgat gaaatccttg agagttttac tagtgatcct gtggcttcag ttgagctggg | 60 |
| tttggagcca acagaaggag gtggagcaga attctggacc cctcagtgtt ccagagggag | 120 |
| ccattgcctc tctcaactgc acttacagtg accgaggttc ccagtccttc ttctggtaca | 180 |
| gacaatattc tgggaaaagc cctgagttga ataatgttcat atactccaat ggtgacaaag | 240 |
| aagatggaag gtttacagca cagctcaata agccagcca gtatgtttct ctgctcatca | 300 |
| gagactccca gcccagtgat tcagccacct acctctgtgc cgtgaacttc ggaggaggaa | 360 |
| agcttatctt cggacaggga acggagttat ctgtgaaacc caatatccag aaccctgacc | 420 |
| ctgccgtgta ccagctgaga gactctaaat ccagtgacaa gtctgtctgc ctattcaccg | 480 |
| attttgattc tcaaacaaat gtgtcacaaa gtaaggattc tgatgtgtat atcacagaca | 540 |
| aaactgtgct agacatgagg tctatggact tcaagagcaa cagtgctgtg gcctggagca | 600 |
| acaaatctga ctttgcatgt gcaaacgcct tcaacaacag cattattcca gaagacacct | 660 |
| tcttccccag cccagaaagt tcctgtgatg tcaagctggt cgagaaaagc tttgaaacag | 720 |
| atacgaacct aaactttcaa aacctgtcag tgattgggtt ccgaatcctc ctcctgaagg | 780 |
| tggccgggtt taatctgctc atgacgctgc ggctgtggtc cagcagagcc aaaagagagg | 840 |
| gcagaggaag tcttctaaca tgcggtgacg tggaggagaa tcccggccct atgagaatca | 900 |
| ggctcctgtg ctgtgtggcc ttttctctcc tgtgggcagg tccagtgatt gctgggatca | 960 |
| cccaggcacc aacatctcag atcctggcag caggacggcg catgacactg agatgtaccc | 1020 |
| aggatatgag acataatgcc atgtactggt atagacaaga tctaggactg gggctaaggc | 1080 |
| tcatccatta ttcaaatact gcaggtacca ctggcaaagg agaagtccct gatggttata | 1140 |
| gtgtctccag agcaaacaca gatgatttcc ccctcacgtt ggcgtctgct gtaccctctc | 1200 |

```
agacatctgt gtacttctgt gccagcagcc taagtttcgg cactgaagct ttctttggac    1260
aaggcaccag actcacagtt gtagaggacc tgaacaaggt gttcccaccc gaggtcgctg    1320
tgtttgagcc atcagaagca gagatctccc acacccaaaa ggccacactg gtgtgcctgg    1380
ccacaggctt cttccctgac cacgtggagc tgagctggtg ggtgaatggg aaggaggtgc    1440
acagtggggt cagcacggac ccgcagcccc tcaaggagca gcccgccctc aatgactcca    1500
gatactgcct gagcagccgc ctgagggtct cggccacctt ctggcagaac ccccgcaacc    1560
acttccgctg tcaagtccag ttctacgggc tctcggagaa tgacgagtgg acccaggata    1620
gggccaaacc cgtcacccag atcgtcagcg ccgaggcctg gggtagagca gactgtggct    1680
ttacctcggt gtcctaccag caaggggtcc tgtctgccac catcctctat gagatcctgc    1740
tagggaaggc caccctgtat gctgtgctgg tcagcgccct tgtgttgatg ccatggtca    1800
agagaaagga tttcggatcc atggctgcag gaggtcccgg cgcggggtct gcggccccgg    1860
tctcctccac atcctccctt cccctggctg ctctcaacat gcgagtgcgg cgccgcctgt    1920
ctctgttctt gaacgtgcgg acacaggtgg cggccgactg gaccgcgctg gcggaggaga    1980
tggactttga gtacttggag atccggcaac tggagacaca gcggacccc actggcaggc    2040
tgctggacgc ctggcaggga cgccctggcg cctctgtagg ccgactgctc gagctgctta    2100
ccaagctggg ccgcgacgac gtgctgctgg agctgggacc cagcattgag gaggattgcc    2160
aaaagtatat cttgaagcag cagcaggagg aggctgagaa gcctttacag gtggccgctg    2220
tagacagcag tgtcccacgg acagcagagc tggcgggcat caccacactt gatgaccccc    2280
tgggg                                                                2285
```

```
<210> SEQ ID NO 12
<211> LENGTH: 235
<212> TYPE: PRT
<213> ORGANISM: Homo sapiens

<400> SEQUENCE: 12

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175
```

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 13
<211> LENGTH: 203
<212> TYPE: PRT
<213> ORGANISM: Artificial Sequence
<220> FEATURE:
<223> OTHER INFORMATION: Human CD8a without the intracellular signaling
      domain

<400> SEQUENCE: 13

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
            85                  90                  95

Thr Phe Val Leu Thr Leu Ser Asp Phe Arg Arg Glu Asn Glu Gly Tyr
        100                 105                 110

Tyr Phe Cys Ser Ala Leu Ser Asn Ser Ile Met Tyr Phe Ser His Phe
    115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
            165                 170                 175

Leu Asp Phe Ala Cys Asp Ile Tyr Ile Trp Ala Pro Leu Ala Gly Thr
        180                 185                 190

Cys Gly Val Leu Leu Leu Ser Leu Val Ile Thr
    195                 200

<210> SEQ ID NO 14
<211> LENGTH: 358
<212> TYPE: PRT
<213> ORGANISM: Artificial Sequence
<220> FEATURE:
<223> OTHER INFORMATION: Human CD8a-MyD88 where MyD88 lacks the TIR
      domain

<400> SEQUENCE: 14

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
             35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Met Ala Ala Gly Gly
        195                 200                 205

Pro Gly Ala Gly Ser Ala Ala Pro Val Ser Ser Thr Ser Ser Leu Pro
210                 215                 220

Leu Ala Ala Leu Asn Met Arg Val Arg Arg Leu Ser Leu Phe Leu
225                 230                 235                 240

Asn Val Arg Thr Gln Val Ala Ala Asp Trp Thr Ala Leu Ala Glu Glu
                245                 250                 255

Met Asp Phe Glu Tyr Leu Glu Ile Arg Gln Leu Glu Thr Gln Ala Asp
            260                 265                 270

Pro Thr Gly Arg Leu Leu Asp Ala Trp Gln Gly Arg Pro Gly Ala Ser
        275                 280                 285

Val Gly Arg Leu Leu Glu Leu Leu Thr Lys Leu Gly Arg Asp Asp Val
290                 295                 300

Leu Leu Glu Leu Gly Pro Ser Ile Glu Glu Asp Cys Gln Lys Tyr Ile
305                 310                 315                 320

Leu Lys Gln Gln Gln Glu Glu Ala Glu Lys Pro Leu Gln Val Ala Ala
                325                 330                 335

Val Asp Ser Ser Val Pro Arg Thr Ala Glu Leu Ala Gly Ile Thr Thr
            340                 345                 350

Leu Asp Asp Pro Leu Gly
        355

<210> SEQ ID NO 15
<211> LENGTH: 247
<212> TYPE: PRT
<213> ORGANISM: Mus musculus

<400> SEQUENCE: 15

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
                20                  25                  30

Glu Leu Arg Ile Phe Pro Lys Lys Met Asp Ala Glu Leu Gly Gln Lys
            35                  40                  45

```
Val Asp Leu Val Cys Glu Val Leu Gly Ser Val Ser Gln Gly Cys Ser
 50                  55                  60

Trp Leu Phe Gln Asn Ser Ser Lys Leu Pro Gln Pro Thr Phe Val
 65                  70                  75                  80

Val Tyr Met Ala Ser Ser His Asn Lys Ile Thr Trp Asp Glu Lys Leu
                 85                  90                  95

Asn Ser Ser Lys Leu Phe Ser Ala Met Arg Asp Thr Asn Asn Lys Tyr
                100                 105                 110

Val Leu Thr Leu Asn Lys Phe Ser Lys Glu Asn Glu Gly Tyr Tyr Phe
            115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
                180                 185                 190

Cys Asp Ile Tyr Ile Trp Ala Pro Leu Ala Gly Ile Cys Val Ala Leu
                195                 200                 205

Leu Leu Ser Leu Ile Ile Thr Leu Ile Cys Tyr His Arg Ser Arg Lys
            210                 215                 220

Arg Val Cys Lys Cys Pro Arg Pro Leu Val Arg Gln Glu Gly Lys Pro
225                 230                 235                 240

Arg Pro Ser Glu Lys Ile Val
                245

<210> SEQ ID NO 16
<211> LENGTH: 217
<212> TYPE: PRT
<213> ORGANISM: Artificial Sequence
<220> FEATURE:
<223> OTHER INFORMATION: Mouse CD8a without the intracellular signaling
      domain

<400> SEQUENCE: 16

Met Ala Ser Pro Leu Thr Arg Phe Leu Ser Leu Asn Leu Leu Leu Leu
 1               5                  10                  15

Gly Glu Ser Ile Ile Leu Gly Ser Gly Glu Ala Lys Pro Gln Ala Pro
                 20                  25                  30

Glu Leu Arg Ile Phe Pro Lys Lys Met Asp Ala Glu Leu Gly Gln Lys
             35                  40                  45

Val Asp Leu Val Cys Glu Val Leu Gly Ser Val Ser Gln Gly Cys Ser
 50                  55                  60

Trp Leu Phe Gln Asn Ser Ser Lys Leu Pro Gln Pro Thr Phe Val
 65                  70                  75                  80

Val Tyr Met Ala Ser Ser His Asn Lys Ile Thr Trp Asp Glu Lys Leu
                 85                  90                  95

Asn Ser Ser Lys Leu Phe Ser Ala Met Arg Asp Thr Asn Asn Lys Tyr
                100                 105                 110

Val Leu Thr Leu Asn Lys Phe Ser Lys Glu Asn Glu Gly Tyr Tyr Phe
            115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
```

```
                        145                 150                 155                 160
Pro Ser Pro Val His Pro Thr Gly Thr Ser Gln Pro Gln Arg Pro Glu
                    165                 170                 175

Asp Cys Arg Pro Arg Gly Ser Val Lys Gly Thr Gly Leu Asp Phe Ala
                180                 185                 190

Cys Asp Ile Tyr Ile Trp Ala Pro Leu Ala Gly Ile Cys Val Ala Leu
            195                 200                 205

Leu Leu Ser Leu Ile Ile Thr Leu Ile
        210                 215

<210> SEQ ID NO 17
<211> LENGTH: 372
<212> TYPE: PRT
<213> ORGANISM: Artificial Sequence
<220> FEATURE:
<223> OTHER INFORMATION: Mouse CD8a-human MyD88 where MyD88 lacks TIR
      domain

<400> SEQUENCE: 17

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
    50                  55                  60

Trp Leu Phe Gln Asn Ser Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Met Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
    130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Leu
        195                 200                 205

Leu Leu Ser Leu Ile Ile Thr Leu Ile Met Ala Ala Gly Gly Pro Gly
    210                 215                 220

Ala Gly Ser Ala Ala Pro Val Ser Ser Thr Ser Ser Leu Pro Leu Ala
225                 230                 235                 240

Ala Leu Asn Met Arg Val Arg Arg Arg Leu Ser Leu Phe Leu Asn Val
                245                 250                 255

Arg Thr Gln Val Ala Ala Asp Trp Thr Ala Leu Ala Glu Glu Met Asp
            260                 265                 270

Phe Glu Tyr Leu Glu Ile Arg Gln Leu Glu Thr Gln Ala Asp Pro Thr
        275                 280                 285
```

Gly Arg Leu Leu Asp Ala Trp Gln Gly Arg Pro Gly Ala Ser Val Gly
            290                 295                 300

Arg Leu Leu Glu Leu Leu Thr Lys Leu Gly Arg Asp Asp Val Leu Leu
305                 310                 315                 320

Glu Leu Gly Pro Ser Ile Glu Glu Asp Cys Gln Lys Tyr Ile Leu Lys
                325                 330                 335

Gln Gln Gln Glu Glu Ala Glu Lys Pro Leu Gln Val Ala Ala Val Asp
            340                 345                 350

Ser Ser Val Pro Arg Thr Ala Glu Leu Ala Gly Ile Thr Thr Leu Asp
                355                 360                 365

Asp Pro Leu Gly
            370

<210> SEQ ID NO 18
<211> LENGTH: 238
<212> TYPE: PRT
<213> ORGANISM: Artificial Sequence
<220> FEATURE:
<223> OTHER INFORMATION: Human CD8a TM-MyD88

<400> SEQUENCE: 18

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Met Ala Ala Gly Gly Pro Gly Ala Gly Ser Ala Ala Pro
                85                  90                  95

Val Ser Ser Thr Ser Ser Leu Pro Leu Ala Ala Leu Asn Met Arg Val
            100                 105                 110

Arg Arg Arg Leu Ser Leu Phe Leu Asn Val Arg Thr Gln Val Ala Ala
        115                 120                 125

Asp Trp Thr Ala Leu Ala Glu Glu Met Asp Phe Glu Tyr Leu Glu Ile
    130                 135                 140

Arg Gln Leu Glu Thr Gln Ala Asp Pro Thr Gly Arg Leu Leu Asp Ala
145                 150                 155                 160

Trp Gln Gly Arg Pro Gly Ala Ser Val Gly Arg Leu Leu Glu Leu Leu
                165                 170                 175

Thr Lys Leu Gly Arg Asp Asp Val Leu Leu Glu Leu Gly Pro Ser Ile
            180                 185                 190

Glu Glu Asp Cys Gln Lys Tyr Ile Leu Lys Gln Gln Gln Glu Glu Ala
        195                 200                 205

Glu Lys Pro Leu Gln Val Ala Ala Val Asp Ser Ser Val Pro Arg Thr
    210                 215                 220

Ala Glu Leu Ala Gly Ile Thr Thr Leu Asp Asp Pro Leu Gly
225                 230                 235

<210> SEQ ID NO 19
<211> LENGTH: 417
<212> TYPE: PRT
<213> ORGANISM: Artificial Sequence
<220> FEATURE:

<223> OTHER INFORMATION: Mouse CD8a-human CD28-human 41BB-human CD3zeta

<400> SEQUENCE: 19

```
Met Ala Ser Pro Leu Thr Arg Phe Leu Ser Leu Asn Leu Leu Leu Leu
  1               5                  10                  15

Gly Glu Ser Ile Ile Leu Gly Ser Gly Glu Ala Lys Pro Gln Ala Pro
             20                  25                  30

Glu Leu Arg Ile Phe Pro Lys Lys Met Asp Ala Glu Leu Gly Gln Lys
         35                  40                  45

Val Asp Leu Val Cys Glu Val Leu Gly Ser Val Ser Gln Gly Cys Ser
 50                  55                  60

Trp Leu Phe Gln Asn Ser Ser Lys Leu Pro Gln Pro Thr Phe Val
 65                  70                  75                  80

Val Tyr Met Ala Ser Ser His Asn Lys Ile Thr Trp Asp Glu Lys Leu
                 85                  90                  95

Asn Ser Ser Lys Leu Phe Ser Ala Met Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Leu
        195                 200                 205

Leu Leu Ser Leu Ile Ile Thr Leu Ile Arg Ser Lys Arg Ser Arg Leu
210                 215                 220

Leu His Ser Asp Tyr Met Asn Met Thr Pro Arg Arg Pro Gly Pro Thr
225                 230                 235                 240

Arg Lys His Tyr Gln Pro Tyr Ala Pro Pro Arg Asp Phe Ala Ala Tyr
                245                 250                 255

Arg Ser Arg Phe Ser Val Val Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
290                 295                 300

Leu Arg Val Lys Phe Ser Arg Ser Ala Asp Ala Pro Ala Tyr Gln Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
370                 375                 380

Arg Arg Arg Gly Lys Gly His Asp Gly Leu Tyr Gln Gly Leu Ser Thr
385                 390                 395                 400
```

Ala Thr Lys Asp Thr Tyr Asp Ala Leu His Met Gln Ala Leu Pro Pro
                    405                 410                 415

Arg

<210> SEQ ID NO 20
<211> LENGTH: 575
<212> TYPE: PRT
<213> ORGANISM: Artificial Sequence
<220> FEATURE:
<223> OTHER INFORMATION: Human CD4-MyD88 where MyD88 lacks the TIR
      domain

<400> SEQUENCE: 20

Met Glu Thr Asn Arg Gly Val Pro Phe Arg His Leu Leu Leu Val Leu
1               5                   10                  15

Gln Leu Ala Leu Leu Pro Ala Ala Thr Gln Gly Lys Lys Val Val Leu
            20                  25                  30

Gly Lys Lys Gly Asp Thr Val Glu Leu Thr Cys Thr Ala Ser Gln Lys
        35                  40                  45

Lys Ser Ile Gln Phe His Trp Lys Asn Ser Asn Gln Ile Lys Ile Leu
50                  55                  60

Gly Asn Gln Gly Ser Phe Leu Thr Lys Gly Pro Ser Lys Leu Asn Asp
65                  70                  75                  80

Arg Ala Asp Ser Arg Arg Ser Leu Trp Asp Gln Gly Asn Phe Pro Leu
                85                  90                  95

Ile Ile Lys Asn Leu Lys Ile Glu Asp Ser Asp Thr Tyr Ile Cys Glu
            100                 105                 110

Val Glu Asp Gln Lys Glu Glu Val Gln Leu Leu Val Phe Gly Leu Thr
        115                 120                 125

Ala Asn Ser Asp Thr His Leu Leu Gln Gly Gln Ser Leu Thr Leu Thr
130                 135                 140

Leu Glu Ser Pro Pro Gly Ser Ser Pro Ser Val Gln Cys Arg Ser Pro
145                 150                 155                 160

Arg Gly Lys Asn Ile Gln Gly Gly Lys Thr Leu Ser Val Ser Gln Leu
                165                 170                 175

Glu Leu Gln Asp Ser Gly Thr Trp Thr Cys Thr Val Leu Gln Asn Gln
            180                 185                 190

Lys Lys Val Glu Phe Lys Ile Asp Ile Val Val Leu Ala Phe Gln Lys
        195                 200                 205

Ala Ser Ser Ile Val Tyr Lys Lys Glu Gly Glu Gln Val Glu Phe Ser
210                 215                 220

Phe Pro Leu Ala Phe Thr Val Glu Lys Leu Thr Gly Ser Gly Glu Leu
225                 230                 235                 240

Trp Trp Gln Ala Glu Arg Ala Ser Ser Lys Ser Trp Ile Thr Phe
                245                 250                 255

Asp Leu Lys Asn Lys Glu Val Ser Val Lys Arg Val Thr Gln Asp Pro
            260                 265                 270

Lys Leu Gln Met Gly Lys Lys Leu Pro Leu His Leu Thr Leu Pro Gln
        275                 280                 285

Ala Leu Pro Gln Tyr Ala Gly Ser Gly Asn Leu Thr Leu Ala Leu Glu
290                 295                 300

Ala Lys Thr Gly Lys Leu His Gln Glu Val Asn Leu Val Val Met Arg
305                 310                 315                 320

Ala Thr Gln Leu Gln Lys Asn Leu Thr Cys Glu Val Trp Gly Pro Thr
                325                 330                 335

-continued

```
Ser Pro Lys Leu Met Leu Ser Leu Lys Leu Glu Asn Lys Glu Ala Lys
                340                 345                 350

Val Ser Lys Arg Glu Lys Ala Val Trp Val Leu Asn Pro Glu Ala Gly
            355                 360                 365

Met Trp Gln Cys Leu Leu Ser Asp Ser Gly Gln Val Leu Leu Glu Ser
        370                 375                 380

Asn Ile Lys Val Leu Pro Thr Trp Ser Thr Pro Val Gln Pro Met Ala
385                 390                 395                 400

Leu Ile Val Leu Gly Gly Val Ala Gly Leu Leu Phe Ile Gly Leu
                405                 410                 415

Gly Ile Phe Phe Met Ala Ala Gly Gly Pro Gly Ala Gly Ser Ala Ala
            420                 425                 430

Pro Val Ser Ser Thr Ser Ser Leu Pro Leu Ala Ala Leu Asn Met Arg
        435                 440                 445

Val Arg Arg Arg Leu Ser Leu Phe Leu Asn Val Arg Thr Gln Val Ala
450                 455                 460

Ala Asp Trp Thr Ala Leu Ala Glu Glu Met Asp Phe Glu Tyr Leu Glu
465                 470                 475                 480

Ile Arg Gln Leu Glu Thr Gln Ala Asp Pro Thr Gly Arg Leu Leu Asp
                485                 490                 495

Ala Trp Gln Gly Arg Pro Gly Ala Ser Val Gly Arg Leu Leu Glu Leu
            500                 505                 510

Leu Thr Lys Leu Gly Arg Asp Asp Val Leu Leu Glu Leu Gly Pro Ser
        515                 520                 525

Ile Glu Glu Asp Cys Gln Lys Tyr Ile Leu Lys Gln Gln Gln Glu Glu
    530                 535                 540

Ala Glu Lys Pro Leu Gln Val Ala Ala Val Asp Ser Ser Val Pro Arg
545                 550                 555                 560

Thr Ala Glu Leu Ala Gly Ile Thr Thr Leu Asp Asp Pro Leu Gly
                565                 570                 575

<210> SEQ ID NO 21
<211> LENGTH: 576
<212> TYPE: PRT
<213> ORGANISM: Artificial Sequence
<220> FEATURE:
<223> OTHER INFORMATION: Mouse CD4-human MyD88 where MyD88 lacks the TIR
      domain

<400> SEQUENCE: 21

Met Glu Thr Cys Arg Ala Ile Ser Leu Arg Arg Leu Leu Leu Leu
1               5                   10                  15

Leu Gln Leu Ser Gln Leu Leu Ala Val Thr Gln Gly Lys Thr Leu Val
                20                  25                  30

Leu Gly Lys Glu Gly Glu Ser Ala Glu Leu Pro Cys Glu Ser Ser Gln
            35                  40                  45

Lys Lys Ile Thr Val Phe Thr Trp Lys Phe Ser Asp Gln Arg Lys Ile
        50                  55                  60

Leu Gly Gln His Gly Lys Gly Val Leu Ile Arg Gly Gly Ser Pro Ser
65                  70                  75                  80

Gln Phe Asp Arg Phe Asp Ser Lys Lys Gly Ala Trp Glu Lys Gly Ser
                85                  90                  95

Phe Pro Leu Ile Ile Asn Lys Leu Lys Met Glu Thr Glu Asp Ser Gln
            100                 105                 110

Thr Tyr Ile Cys Glu Leu Glu Asn Arg Lys Glu Glu Val Glu Leu Trp
        115                 120                 125
```

```
Val Phe Lys Val Thr Phe Ser Pro Gly Thr Ser Leu Leu Gln Gly Gln
    130                 135                 140

Ser Leu Thr Leu Thr Leu Asp Ser Asn Ser Lys Val Ser Asn Pro Leu
145                 150                 155                 160

Thr Glu Cys Lys His Lys Lys Gly Lys Val Val Ser Gly Ser Lys Val
                165                 170                 175

Leu Ser Met Ser Asn Leu Arg Val Gln Asp Ser Asp Phe Trp Asn Cys
            180                 185                 190

Thr Val Thr Leu Asp Gln Lys Lys Asn Trp Phe Gly Met Thr Leu Ser
        195                 200                 205

Val Leu Gly Phe Gln Ser Thr Ala Ile Thr Ala Tyr Lys Ser Glu Gly
    210                 215                 220

Glu Ser Ala Glu Phe Ser Phe Pro Leu Asn Phe Ala Glu Glu Asn Gly
225                 230                 235                 240

Trp Gly Glu Leu Met Trp Lys Ala Glu Lys Asp Ser Phe Phe Gln Pro
                245                 250                 255

Trp Ile Ser Phe Ser Ile Lys Asn Lys Glu Val Ser Val Gln Lys Ser
            260                 265                 270

Thr Lys Asp Leu Lys Leu Gln Leu Lys Glu Thr Leu Pro Leu Thr Leu
        275                 280                 285

Lys Ile Pro Gln Val Ser Leu Gln Phe Ala Gly Ser Gly Asn Leu Thr
    290                 295                 300

Leu Thr Leu Asp Lys Gly Thr Leu His Gln Glu Val Asn Leu Val Val
305                 310                 315                 320

Met Lys Val Ala Gln Leu Asn Asn Thr Leu Thr Cys Glu Val Met Gly
                325                 330                 335

Pro Thr Ser Pro Lys Met Arg Leu Thr Leu Lys Gln Glu Asn Gln Glu
            340                 345                 350

Ala Arg Val Ser Glu Glu Gln Lys Val Val Gln Val Val Ala Pro Glu
        355                 360                 365

Thr Gly Leu Trp Gln Cys Leu Leu Ser Glu Gly Asp Lys Val Lys Met
    370                 375                 380

Asp Ser Arg Ile Gln Val Leu Ser Arg Gly Val Asn Gln Thr Val Phe
385                 390                 395                 400

Leu Ala Cys Val Leu Gly Gly Ser Phe Gly Phe Leu Gly Phe Leu Gly
                405                 410                 415

Leu Cys Ile Leu Cys Met Ala Ala Gly Gly Pro Gly Ala Gly Ser Ala
            420                 425                 430

Ala Pro Val Ser Ser Thr Ser Ser Leu Pro Leu Ala Ala Leu Asn Met
        435                 440                 445

Arg Val Arg Arg Arg Leu Ser Leu Phe Leu Asn Val Arg Thr Gln Val
    450                 455                 460

Ala Ala Asp Trp Thr Ala Leu Ala Glu Glu Met Asp Phe Glu Tyr Leu
465                 470                 475                 480

Glu Ile Arg Gln Leu Glu Thr Gln Ala Asp Pro Thr Gly Arg Leu Leu
                485                 490                 495

Asp Ala Trp Gln Gly Arg Pro Gly Ala Ser Val Gly Arg Leu Leu Glu
            500                 505                 510

Leu Leu Thr Lys Leu Gly Arg Asp Asp Val Leu Leu Glu Leu Gly Pro
        515                 520                 525

Ser Ile Glu Glu Asp Cys Gln Lys Tyr Ile Leu Lys Gln Gln Gln Glu
530                 535                 540
```

```
Glu Ala Glu Lys Pro Leu Gln Val Ala Val Asp Ser Ser Val Pro
545                 550                 555                 560

Arg Thr Ala Glu Leu Ala Gly Ile Thr Thr Leu Asp Asp Pro Leu Gly
                565                 570                 575

<210> SEQ ID NO 22
<211> LENGTH: 780
<212> TYPE: PRT
<213> ORGANISM: Artificial Sequence
<220> FEATURE:
<223> OTHER INFORMATION: Human DMF5 TCR-MyD88 where MyD88 lacks the TIR
      domain

<400> SEQUENCE: 22

Met Glu Thr Met Glu Thr Lys Ser Leu Arg Val Leu Val Ile Leu
1               5                   10                  15

Trp Leu Gln Leu Ser Trp Val Trp Ser Gln Gln Lys Glu Val Glu Gln
                20                  25                  30

Asn Ser Gly Pro Leu Ser Val Pro Glu Gly Ala Ile Ala Ser Leu Asn
            35                  40                  45

Cys Thr Tyr Ser Asp Arg Gly Ser Gln Ser Phe Phe Trp Tyr Arg Gln
        50                  55                  60

Tyr Ser Gly Lys Ser Pro Glu Leu Ile Met Glu Thr Phe Ile Tyr Ser
65                  70                  75                  80

Asn Gly Asp Lys Glu Asp Gly Arg Phe Thr Ala Gln Leu Asn Lys Ala
                85                  90                  95

Ser Gln Tyr Val Ser Leu Leu Ile Arg Asp Ser Gln Pro Ser Asp Ser
            100                 105                 110

Ala Thr Tyr Leu Cys Ala Val Asn Phe Gly Gly Gly Lys Leu Ile Phe
        115                 120                 125

Gly Gln Gly Thr Glu Leu Ser Val Lys Pro Asn Ile Gln Asn Pro Asp
    130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Glu Thr
            180                 185                 190

Arg Ser Met Glu Thr Asp Phe Lys Ser Asn Ser Ala Val Ala Trp Ser
        195                 200                 205

Asn Lys Ser Asp Phe Ala Cys Ala Asn Ala Phe Asn Asn Ser Ile Ile
    210                 215                 220

Pro Glu Asp Thr Phe Phe Pro Ser Pro Glu Ser Ser Cys Asp Val Lys
225                 230                 235                 240

Leu Val Glu Lys Ser Phe Glu Thr Asp Thr Asn Leu Asn Phe Gln Asn
                245                 250                 255

Leu Ser Val Ile Gly Phe Arg Ile Leu Leu Leu Lys Val Ala Gly Phe
            260                 265                 270

Asn Leu Leu Met Glu Thr Thr Leu Arg Leu Trp Ser Ser Arg Ala Lys
        275                 280                 285

Arg Glu Gly Arg Gly Ser Leu Leu Thr Cys Gly Asp Val Glu Glu Asn
    290                 295                 300

Pro Gly Pro Met Glu Thr Arg Ile Arg Leu Leu Cys Cys Val Ala Phe
305                 310                 315                 320

Ser Leu Leu Trp Ala Gly Pro Val Ile Ala Gly Ile Thr Gln Ala Pro
                325                 330                 335
```

```
Thr Ser Gln Ile Leu Ala Ala Gly Arg Arg Met Glu Thr Thr Leu Arg
            340                 345                 350

Cys Thr Gln Asp Met Glu Thr Arg His Asn Ala Met Tyr Trp Tyr Arg
            355                 360                 365

Gln Asp Leu Gly Leu Gly Leu Arg Leu Ile His Tyr Ser Asn Thr Ala
            370                 375                 380

Gly Thr Thr Gly Lys Gly Glu Val Pro Asp Gly Tyr Ser Val Ser Arg
385                 390                 395                 400

Ala Asn Thr Asp Asp Phe Pro Leu Thr Leu Ala Ser Ala Val Pro Ser
                405                 410                 415

Gln Thr Ser Val Tyr Phe Cys Ala Ser Ser Leu Ser Phe Gly Thr Glu
            420                 425                 430

Ala Phe Phe Gly Gln Gly Thr Arg Leu Thr Val Val Glu Asp Leu Asn
            435                 440                 445

Lys Val Phe Pro Pro Glu Val Ala Val Phe Glu Pro Ser Glu Ala Glu
            450                 455                 460

Ile Ser His Thr Gln Lys Ala Thr Leu Val Cys Leu Ala Thr Gly Phe
465                 470                 475                 480

Phe Pro Asp His Val Glu Leu Ser Trp Trp Val Asn Gly Lys Glu Val
                485                 490                 495

His Ser Gly Val Ser Thr Asp Pro Gln Pro Leu Lys Glu Gln Pro Ala
            500                 505                 510

Leu Asn Asp Ser Arg Tyr Cys Leu Ser Ser Arg Leu Arg Val Ser Ala
            515                 520                 525

Thr Phe Trp Gln Asn Pro Arg Asn His Phe Arg Cys Gln Val Gln Phe
            530                 535                 540

Tyr Gly Leu Ser Glu Asn Asp Glu Trp Thr Gln Asp Arg Ala Lys Pro
545                 550                 555                 560

Val Thr Gln Ile Val Ser Ala Glu Ala Trp Gly Arg Ala Asp Cys Gly
                565                 570                 575

Phe Thr Ser Val Ser Tyr Gln Gln Gly Val Leu Ser Ala Thr Ile Leu
            580                 585                 590

Tyr Glu Ile Leu Leu Gly Lys Ala Thr Leu Tyr Ala Val Leu Val Ser
            595                 600                 605

Ala Leu Val Leu Met Ala Met Val Lys Arg Lys Asp Phe Gly Ser Met
            610                 615                 620

Ala Ala Gly Gly Pro Gly Ala Gly Ser Ala Ala Pro Val Ser Ser Thr
625                 630                 635                 640

Ser Ser Leu Pro Leu Ala Ala Leu Asn Met Arg Val Arg Arg Arg Leu
                645                 650                 655

Ser Leu Phe Leu Asn Val Arg Thr Gln Val Ala Ala Asp Trp Thr Ala
            660                 665                 670

Leu Ala Glu Glu Met Asp Phe Glu Tyr Leu Glu Ile Arg Gln Leu Glu
            675                 680                 685

Thr Gln Ala Asp Pro Thr Gly Arg Leu Leu Asp Ala Trp Gln Gly Arg
            690                 695                 700

Pro Gly Ala Ser Val Gly Arg Leu Leu Glu Leu Leu Thr Lys Leu Gly
705                 710                 715                 720

Arg Asp Asp Val Leu Leu Glu Leu Gly Pro Ser Ile Glu Glu Asp Cys
                725                 730                 735

Gln Lys Tyr Ile Leu Lys Gln Gln Gln Glu Glu Ala Glu Lys Pro Leu
            740                 745                 750
```

```
Gln Val Ala Val Asp Ser Val Pro Arg Thr Ala Glu Leu Ala
        755                 760                 765
Gly Ile Thr Thr Leu Asp Asp Pro Leu Gly Gly Ser
    770                 775                 780

<210> SEQ ID NO 23
<211> LENGTH: 247
<212> TYPE: PRT
<213> ORGANISM: Artificial Sequence
<220> FEATURE:
<223> OTHER INFORMATION: Mouse CD8a protein with K73A mutation

<400> SEQUENCE: 23

Met Ala Ser Pro Leu Thr Arg Phe Leu Ser Leu Asn Leu Leu Leu Leu
  1               5                  10                  15
Gly Glu Ser Ile Ile Leu Gly Ser Gly Glu Ala Lys Pro Gln Ala Pro
                 20                  25                  30
Glu Leu Arg Ile Phe Pro Lys Lys Met Asp Ala Glu Leu Gly Gln Lys
             35                  40                  45
Val Asp Leu Val Cys Glu Val Leu Gly Ser Val Ser Gln Gly Cys Ser
         50                  55                  60
Trp Leu Phe Gln Asn Ser Ser Ser Ala Leu Pro Gln Pro Thr Phe Val
 65                  70                  75                  80
Val Tyr Met Ala Ser Ser His Asn Lys Ile Thr Trp Asp Glu Lys Leu
                 85                  90                  95
Asn Ser Ser Lys Leu Phe Ser Ala Met Arg Asp Thr Asn Asn Lys Tyr
            100                 105                 110
Val Leu Thr Leu Asn Lys Phe Ser Lys Glu Asn Glu Gly Tyr Tyr Phe
        115                 120                 125
Cys Ser Val Ile Ser Asn Ser Val Met Tyr Phe Ser Ser Val Val Pro
    130                 135                 140
Val Leu Gln Lys Val Asn Ser Thr Thr Thr Lys Pro Val Leu Arg Thr
145                 150                 155                 160
Pro Ser Pro Val His Pro Thr Gly Thr Ser Gln Pro Gln Arg Pro Glu
                165                 170                 175
Asp Cys Arg Pro Arg Gly Ser Val Lys Gly Thr Gly Leu Asp Phe Ala
            180                 185                 190
Cys Asp Ile Tyr Ile Trp Ala Pro Leu Ala Gly Ile Cys Val Ala Leu
        195                 200                 205
Leu Leu Ser Leu Ile Ile Thr Leu Ile Cys Tyr His Arg Ser Arg Lys
    210                 215                 220
Arg Val Cys Lys Cys Pro Arg Pro Leu Val Arg Gln Glu Gly Lys Pro
225                 230                 235                 240
Arg Pro Ser Glu Lys Ile Val
                245

<210> SEQ ID NO 24
<211> LENGTH: 296
<212> TYPE: PRT
<213> ORGANISM: Homo sapiens

<400> SEQUENCE: 24

Met Ala Ala Gly Gly Pro Gly Ala Gly Ser Ala Ala Pro Val Ser Ser
  1               5                  10                  15
Thr Ser Ser Leu Pro Leu Ala Ala Leu Asn Met Arg Val Arg Arg Arg
                 20                  25                  30
Leu Ser Leu Phe Leu Asn Val Arg Thr Gln Val Ala Ala Asp Trp Thr
```

-continued

```
                35                     40                     45
Ala Leu Ala Glu Glu Met Asp Phe Glu Tyr Leu Glu Ile Arg Gln Leu
         50                     55                     60
Glu Thr Gln Ala Asp Pro Thr Gly Arg Leu Leu Asp Ala Trp Gln Gly
 65                     70                     75                     80
Arg Pro Gly Ala Ser Val Gly Arg Leu Leu Glu Leu Leu Thr Lys Leu
                 85                     90                     95
Gly Arg Asp Asp Val Leu Leu Glu Leu Gly Pro Ser Ile Glu Glu Asp
                100                    105                    110
Cys Gln Lys Tyr Ile Leu Lys Gln Gln Gln Glu Glu Ala Glu Lys Pro
                115                    120                    125
Leu Gln Val Ala Ala Val Asp Ser Ser Val Pro Arg Thr Ala Glu Leu
        130                    135                    140
Ala Gly Ile Thr Thr Leu Asp Asp Pro Leu Gly His Met Pro Glu Arg
145                    150                    155                    160
Phe Asp Ala Phe Ile Cys Tyr Cys Pro Ser Asp Ile Gln Phe Val Gln
                165                    170                    175
Glu Met Ile Arg Gln Leu Glu Gln Thr Asn Tyr Arg Leu Lys Leu Cys
                180                    185                    190
Val Ser Asp Arg Asp Val Leu Pro Gly Thr Cys Val Trp Ser Ile Ala
        195                    200                    205
Ser Glu Leu Ile Glu Lys Arg Cys Arg Arg Met Val Val Val Val Ser
    210                    215                    220
Asp Asp Tyr Leu Gln Ser Lys Glu Cys Asp Phe Gln Thr Lys Phe Ala
225                    230                    235                    240
Leu Ser Leu Ser Pro Gly Ala His Gln Lys Arg Leu Ile Pro Ile Lys
                245                    250                    255
Tyr Lys Ala Met Lys Lys Glu Phe Pro Ser Ile Leu Arg Phe Ile Thr
                260                    265                    270
Val Cys Asp Tyr Thr Asn Pro Cys Thr Lys Ser Trp Phe Trp Thr Arg
        275                    280                    285
Leu Ala Lys Ala Leu Ser Leu Pro
    290                    295
```